(12) United States Patent
Hamilton et al.

(10) Patent No.: US 11,371,000 B2
(45) Date of Patent: Jun. 28, 2022

(54) DEVICES, SYSTEMS AND METHODS FOR INHIBITING INVASION AND METASTASES OF CANCER

(71) Applicant: EMULATE, INC., Boston, MA (US)

(72) Inventors: Geraldine A Hamilton, Boston, MA (US); Norman Wen, West Roxbury, MA (US); Catherine Karalis, Brookline, MA (US); Antonio Varone, West Roxbury, MA (US); Daniel Levner, Brookline, MA (US); Riccardo Barrile, Boston, MA (US)

(73) Assignee: EMULATE, INC., Boston, MA (US)

( * ) Notice: Subject to any disclaimer, the term of this patent is extended or adjusted under 35 U.S.C. 154(b) by 437 days.

(21) Appl. No.: 15/474,214

(22) Filed: Mar. 30, 2017

(65) Prior Publication Data

US 2017/0285003 A1    Oct. 5, 2017

Related U.S. Application Data

(60) Provisional application No. 62/315,401, filed on Mar. 30, 2016.

(51) Int. Cl.
| | |
|---|---|
| *G01N 33/50* | (2006.01) |
| *C12M 3/06* | (2006.01) |
| *C12M 1/12* | (2006.01) |
| *C12N 5/09* | (2010.01) |

(52) U.S. Cl.
CPC ............ *C12M 23/16* (2013.01); *C12M 25/02* (2013.01); *C12N 5/0693* (2013.01); *G01N 33/5011* (2013.01); *G01N 33/5017* (2013.01)

(58) Field of Classification Search
CPC combination set(s) only.
See application file for complete search history.

(56) References Cited

U.S. PATENT DOCUMENTS

| | | | |
|---|---|---|---|
| 8,647,861 B2 | 2/2014 | Ingber et al. | 435/289.1 |
| 8,940,701 B2 | 1/2015 | Liv | 514/19.3 |
| 2011/0250585 A1* | 10/2011 | Ingber | C12M 25/02 435/5 |
| 2013/0236972 A1 | 9/2013 | Noh et al. | 435/401 |

(Continued)

FOREIGN PATENT DOCUMENTS

| | | |
|---|---|---|
| AU | 2015204375 A1 | 6/2015 |
| WO | WO/2010/009307 | 1/2010 |

(Continued)

OTHER PUBLICATIONS

Hirt et al. "In vitro" 3D models of tumor-immune system interaction. Advanced Drug Delivery Reviews. 2014;79-80:145-154.*

(Continued)

*Primary Examiner* — Kara D Johnson
(74) *Attorney, Agent, or Firm* — Medlen & Carroll, LLP

(57) ABSTRACT

The invention generally relates to a microfluidic platforms or "chips" for testing and understanding cancer, and, more specifically, for understanding the factors that contribute to cancer invading tissues and causing metastases. Tumor cells are grown on microfluidic devices with other non-cancerous tissues under conditions that simulate tumor invasion. The interaction with immune cells can be tested to inhibit this activity by linking a cancer chip to a lymph chip.

7 Claims, 21 Drawing Sheets

(56) References Cited

U.S. PATENT DOCUMENTS

| | | | | |
|---|---|---|---|---|
| 2014/0038279 A1 | 2/2014 | Ingber et al. | ............... | 435/297.2 |
| 2014/0057311 A1* | 2/2014 | Kamm | ............... | B01L 3/502753 |
| | | | | 435/29 |
| 2016/0313306 A1 | 10/2016 | Ingber et al. | ................. | 435/401 |

FOREIGN PATENT DOCUMENTS

| | | |
|---|---|---|
| WO | WO/2012/118799 | 9/2012 |
| WO | WO/2013/086486 | 6/2013 |
| WO | WO/2013/086502 | 6/2013 |
| WO | WO/2015/138032 | 9/2015 |
| WO | WO/2015/138034 | 9/2015 |

OTHER PUBLICATIONS

Mattei et al., A multidisciplinary study using in vivo tumor models and microfluidic cell-on-chip approach to explore the cross-talk between cancer and immune cells. Journal of Immunology, vol. 11, No. 4 (2011) pp. 337-346. (Year: 2011).*

Katt et al., In vitro tumor models: Advantages, disadvantages, variables, and selecting the right platform. Frontiers in Bioengineering and Biotechnology, vol. 4, No. 12 (Feb. 2016) pp. 1-14. (Year: 2016).*

Barker, N. et al. (2010) "Lgr5$^{+ve}$ Stem Cells Drive Self-Renewal in the Stomach and Build Long-Lived Gastric Units In Vitro," *Cell Stem Cell* 6(1), 25-36.

Bhat, R. et al. (2014) "Of plasticity and specificity: dialectics of the micro- and macro-environment and the organ phenotype," *Wiley Interdisciplinary reviews. Membrane Transport and Signaling* 3(2), 147-163.

Chen, Daniel S. et al. (2013) "Oncology Meets Immunology: The Cancer-Immunity Cycle," *Immunity* 39(1), 1-10.

El Rayes, T. et al. (2015) "Lung inflammation promotes metastasis through neutrophil protease-mediated degradation of Tsp-1," *Proceedings of the National Academy of Sciences of the United States of America* 112(52), 16000-16005.

Hanahan, D. et al. (2011) "Hallmarks of Cancer: The Next Generation," *Cell* 144(5), 646-674.

Huh, D. et al. (2010) "Reconstituting Organ-Level Lung Functions on a Chip," *Science* 328(5986), 1662.

Jain, R. K. (2014) "Antiangiogenesis Strategies Revisited: From Starving Tumors to Alleviating Hypoxia," *Cancer Cell* 26(5), 605-622.

Jung, P. et al. (2011) "Isolation and in vitro expansion of human colonic stem cells," *Nature Medicine* 17(10), 1225-1227.

Martin, T. A. et al. (2013) *Cancer Invasion and Metastasis: Molecular and Cellular Perspective*, Landes Bioscience, Austin (TX).

Sato, T. et al. (2013) "Growing Self-Organizing Mini-Guts from a Single Intestinal Stem Cell: Mechanism and Applications," *Science* 340(6137), 1190.

Sato, T. et al. (2009) "Single Lgr5 stem cells build crypt-villus structures in vitro without a mesenchymal niche," *Nature* 459(1244), 262-265.

Veiseh, O. et al. (2011) "Cancer Cell Invasion: Treatment and Monitoring Opportunities in Nanomedicine," *Advanced Drug Delivery Reviews* 63(8), 582-596.

Vidi, P.-A. et al. (2013) "Three-Dimensional Culture of Human Breast Epithelial Cells: The How and the Why," *Methods in molecular biology (Clifton, N.J.)* 945, 193-219.

Wu, W. et al. (2011) "Omnidirectional Printing of 3D Microvascular Networks," *Advanced Materials* 23(24), H178-H183.

Wu, W. et al. (2010) "Directwrite assembly of biomimetic microvascular networks for efficient fluid transport," *Soft Matter* 6, 739-742.

\* cited by examiner

Source: Douglas Hanahan, Robert A. Weinberg, Cancer Cell 2011

B

A

DEVICES, SYSTEMS AND METHODS FOR INHIBITING INVASION AND METASTASES OF CANCER

FIELD OF THE INVENTION

The invention generally relates to a microfluidic platforms or "chips" for testing and understanding cancer, and, more specifically, for understanding the factors that contribute to cancer invading tissues and causing metastases. Tumor cells are grown on microfluidic devices with other non-cancerous tissues under conditions that simulate tumor invasion. The interaction with immune cells can be tested to inhibit this activity by linking a cancer chip to a lymph chip.

BACKGROUND

Success treating particular cancers is also hampered by the fact that the cancer is well-advanced by the time it is diagnosed. Metastatic tumors in the lungs are cancers that developed at other places in the body (or other parts of the lungs) and spread through the bloodstream or lymphatic system to the lungs. It is different than lung cancer that starts in the lungs. Melanoma is but one of many cancers that can metastasize to the lungs. A cure is unlikely in most cases of cancers that have spread to the lungs. But the outlook depends on the underlying cancer. Some cancers, such as lymphoma, are very treatable and even curable. In general, it is rare for someone to live more than 5 years with metastatic cancer to the lungs.

In sheer numbers, colon cancer is even a bigger killer. With 655,000 deaths worldwide per year, it is the third most common form of cancer and the second leading cause of cancer-related death in the Western world. When detected late, surgery may be of no use. For example, 20% of patients present with metastatic (stage 1 V) colorectal cancer at the time of diagnosis, and only 25% of this group will have isolated liver metastasis that is potentially resectable. Radiation is not routinely used since it can cause radiation enteritis. Chemotherapy is often used post-surgery as adjunct therapy. However, the use of chemotherapeutics is complicated by the fact that colon cancer is often found in the elderly, who do not respond well to aggressive chemotherapy.

Breast cancer is the most common malignancy and the second leading cause of cancer death in women. In over 60% of localized breast cancer cases, histologic evidence of tumor spread to surrounding tissue is found. Patients diagnosed with invasive ductal carcinoma, the most common breast cancer, have a lower 10-year survival rate. About 30% of newly diagnosed breast cancer patients have positive lymph nodes and much poorer outcomes.

What is needed are better compounds and methods for treating cancer, including advanced cancer and metastatic disease.

SUMMARY OF THE INVENTION

The invention generally relates to a microfluidic platforms or "chips" for testing and understanding cancer, and, more specifically, for understanding the factors that contribute to cancer invading tissues and causing metastases. Tumor cells are grown on microfluidic devices with other non-cancerous tissues under conditions that simulate or support tumor invasion. The interaction with immune cells can be tested to inhibit this activity by linking a cancer chip to another chip, e.g. a lymph chip, a bone marrow chip, a liver chip, etc. The interaction with circulating immune cells recruited to the tumor site will be enabled to allow testing of immunomodulatory agents. The interaction with circulating immune cells can be tested to confirm immune surveillance (or the lack thereof) and provide a platform for testing of immunotherapeutics. Indeed, these microfluidic platforms can increase our understanding of tumor growth and all the other aspects of cancer, including but not limited to, the factors that contribute to cancer related angiogenesis, the role of ECM on this process, resistance to immune surveillance, and expansion to other organs underlying the development of metastatic disease.

Tumor cells are grown on microfluidic devices with other non-cancerous tissues under conditions that simulate tumor invasion. In one embodiment, tumor cells from a biopsy are assessed for their metastatic potential by seeding them on one or more layers of living cells (e.g. epithelial cells) in a microfluidic device and determining whether they invade said one or more layers. The interaction with immune cells can be tested to inhibit this activity by, among other things, linking a cancer chip to a lymph chip. In one embodiment, the lymph chip is populated by cells from a lymph node.

In one embodiment, the present invention contemplates a microfluidic device comprising: a body having a microchannel (optionally located centrally) therein; and an at least partially porous membrane positioned within the microchannel (and optionally along a plane), the membrane configured to separate the microchannel to form a first microchannel and a second microchannel, the membrane comprising a top surface and a bottom surface, said a) top surface comprises a first layer comprising living stromal cells, a second layer positioned on top of said first layer and comprising living epithelial cells (or the epithelial cells can be placed directly on the membrane with no stromal layer), and living tumor cells in contact with said epithelial cells (or in close proximity), said b) bottom surface comprising living endothelial cells. In one embodiment, said membrane is coated with at least one attachment molecule that supports adhesion of a plurality of living cells. In one embodiment said first and second microchannels comprise fluid (e.g. culture media, blood, lymph, serum, plasma, etc.). In one embodiment, said tumor cells are from a biopsy. In one embodiment, said tumor cells are human tumor cells. In one embodiment, said tumor cells are also in contact with at least one type of immune cell (or in close proximity). In one embodiment, said tumor cells are in contact with lymphocytes (or in close proximity). In one embodiment, said tumor cells are in contact with T cells (or in close proximity). In one embodiment, said T cells are primed T cells (e.g. T cells that have been exposed to antigen, or one or more cytokines, or to cancer cells, or otherwise activated). In one embodiment, said tumor cells are in contact with activated dendritic cells (or in close proximity).

In yet another embodiment, the present invention contemplates a system comprising first and second microfluidic devices in fluidic communication, said a) first microfluidic device comprising a body having a microchannel (optionally located centrally) therein; and an at least partially porous membrane positioned within the microchannel (and optionally along a plane), the membrane configured to separate the microchannel to Ruin a first microchannel and a second microchannel, the membrane comprising a top surface and a bottom surface, said i) top surface comprises a first layer comprising living stromal cells, a second layer positioned on top of said first layer and comprising living epithelial cells, and living tumor cells in contact with said epithelial cells (or in close proximity), said ii) bottom surface comprising living endothelial cells; said b) second microfluidic device comprising immune cells. In one embodiment, said membrane is coated with at least one attachment molecule that supports adhesion of a plurality of living cells. In one embodiment, said first and second microchannels of said first microfluidic device comprise fluid. In one embodiment, said tumor cells are from a biopsy. In one embodiment, said tumor cells are human tumor cells. In one embodiment, said tumor cells are also in contact with at least one type of immune cell (or in close proximity). In one embodiment, said tumor cells are in contact with lymphocytes (or in close proximity). In one embodiment, said tumor cells are in contact with T cells (or in close proximity). In one embodiment, said T cells are primed T cells. In one embodiment, said tumor cells are in contact with activated dendritic cells (or in close proximity).

In yet another embodiment, the present invention contemplates a system comprising first, second and third microfluidic devices in fluidic communication, said a) first microfluidic device comprising a body having a microchannel (optionally located centrally) therein; and an at least partially porous membrane positioned within the microchannel (and optionally along a plane), the membrane configured to separate the microchannel to form a first microchannel and a second microchannel, the membrane comprising a top surface and a bottom surface, said i) top surface comprises a first layer comprising living stromal cells, a second layer positioned on top of said first layer and comprising living epithelial cells, and living tumor cells in contact with said epithelial cells (or in close proximity), said ii) bottom surface comprising living endothelial cells; said b) second microfluidic device comprising immune cells; and said c) third microfluidic device comprising an Organ-on-Chip, (for example, a microfluidic device comprising cells of an organ selected from the group consisting of cells of liver, kidney, lung, colon, intestine, brain, pancreas, skin (or other organ which can serve as a model for a distant metastasis). In one embodiment, said membrane is coated with at least one attachment molecule that supports adhesion of a plurality of living cells. In one embodiment, said first and second microchannels of said first microfluidic device comprise fluid. In one embodiment, said tumor cells are from a biopsy. In one embodiment, said tumor cells are human tumor cells. In one embodiment, said tumor cells are also in contact with at least one type of immune cell (or in close proximity). In one embodiment, said tumor cells are in contact with lymphocytes (or in close proximity). In one embodiment, said tumor cells are in contact with T cells (or in close proximity). In one embodiment, said T cells are primed T cells. In one embodiment, said tumor cells are in contact with activated dendritic cells (or in close proximity).

In yet another embodiment, the present invention contemplates a method comprising: 1) providing a) immune cells and b) a microfluidic device comprising a body having a microchannel (optionally located centrally) therein; and an at least partially porous membrane positioned within the microchannel (and optionally along a plane), the membrane configured to separate the microchannel to form a first microchannel and a second microchannel, the membrane comprising a top surface and a bottom surface, said i) top surface comprises a first layer comprising living stromal cells, a second layer positioned on top of said first layer and comprising living epithelial cells, and living tumor cells in contact with said epithelial cells (or in close proximity), said ii) bottom surface comprising living endothelial cells; and 2) introducing said immune cells into said microfluidic device under conditions such that at least a portion of said immune cells contact said tumor cells. In one embodiment, said membrane is coated with at least one attachment molecule that supports adhesion of a plurality of living cells. In one embodiment, said first and second microchannels comprise fluid. In one embodiment, said tumor cells are from a biopsy. In one embodiment, said tumor cells are human tumor cells. In one embodiment, said immune cells are introduced in step 2) in blood. In one embodiment, said immune cells comprise lymphocytes and said tumor cells are in contact with lymphocytes (or in close proximity). In one embodiment, said lymphocytes comprise T cells. In one embodiment, said T cells are primed T cells. In one embodiment, said immune cells comprise activated dendritic cells and said tumor cells are in contact with activated dendritic cells (or in close proximity).

In yet another embodiment, the present invention contemplates a method comprising: 1) providing a) a first microfluidic device comprising immune cells, said first microfluidic device in fluidic communication with b) a second microfluidic device comprising a body having a microchannel (optionally located centrally) therein; and an at least partially porous membrane positioned within the microchannel (and optionally along a plane), the membrane configured to separate the microchannel to form a first microchannel and a second microchannel, the membrane comprising a top surface and a bottom surface, said i) top surface comprises a first layer comprising living stromal cells, a second layer positioned on top of said first layer and comprising living epithelial cells, and living tumor cells in contact with said epithelial cells (or in close proximity), said ii) bottom surface comprising living endothelial cells; and 2) causing said immune cells in said first microfluidic device to move into said second microfluidic device under conditions such that at least a portion of said immune cells contact said tumor cells. In one embodiment, said immune cells are exposed to one or more cytokines thereby causing said immune cells to move into said second microfluidic device. In one embodiment, fluidic communication is achieved through a conduit selected from the group consisting of a channel, a tube, or bridge, said conduit comprising fluid. In one embodiment, said tumor cells are from a biopsy. In one embodiment, said tumor cells are human tumor cells. In one embodiment, said immune cells of step 2) are in blood. In one embodiment, said immune cells comprise lymphocytes and said tumor cells are in contact with lymphocytes (or in close proximity). In one embodiment, said lymphocytes comprise T cells. In one embodiment, said T cells are primed T cells, said priming taking place in said first microfluidic device. In one embodiment, said immune cells comprise activated dendritic cells and said tumor cells are in contact with activated dendritic cells (or in close proximity).

In still another embodiment, the present invention contemplates a method comprising: 1) providing a) a first microfluidic device comprising immune cells, said first microfluidic device in fluidic communication with b) a second microfluidic device and c) a third microfluidic device, said first microfluidic device comprising a body having a micro channel (optionally located centrally) therein; and an at least partially porous membrane positioned within the microchannel and (optionally along a plane), the membrane configured to separate the microchannel to form a first microchannel and a second microchannel, the membrane comprising a top surface and a bottom surface, said i) top surface comprises a first layer comprising living stromal cells, a second layer positioned on top of said first layer and comprising living epithelial cells, and living tumor cells in contact with said epithelial cells (or in close proximity), said ii) bottom surface comprising living endothelial cells; said third microfluidic device comprising cells of an organ selected from the group consisting of cells of liver, kidney, lung, colon, intestine, brain; and 2) causing said immune cells in said first microfluidic device to move into said second microfluidic device under conditions such that at least a portion of said immune cells contact said tumor cells. In one embodiment, said immune cells are exposed to one or more cytokines in said first microfluidic device thereby causing said immune cells to move into said second microfluidic device. In one embodiment, fluidic communication is achieved through conduits, each conduit selected from the group consisting of a channel, a tube, or bridge, said conduit comprising fluid. In one embodiment, said tumor cells are from a biopsy. In one embodiment, said tumor cells are human tumor cells. In one embodiment, said immune cells of step 2) are in blood. In one embodiment, said immune cells comprise lymphocytes and said tumor cells are in contact with lymphocytes (or in close proximity). In one embodiment, said lymphocytes comprise T cells. In one embodiment, said T cells are primed T cells, said priming taking place in said first microfluidic device. In one embodiment, said immune cells comprise activated dendritic cells and said tumor cells are in contact with activated dendritic cells (or in close proximity). In one embodiment, said third microfluidic device comprises tumor cells in contact with said cells of an organ (or in close proximity). In one embodiment, the method further comprises 3) causing said immune cells in said first microfluidic device to move into said third microfluidic device under conditions such that at least a portion of said immune cells contact said tumor cells (or are in close proximity).

In still a further embodiment, the present invention contemplates a method comprising: 1) providing a) living tumor cells and b) a microfluidic device comprising a body having a microchannel (optionally located centrally) therein; and an at least partially porous membrane positioned within the microchannel (and optionally along a plane), the membrane configured to separate the microchannel to foam a first microchannel and a second microchannel, the membrane comprising a top surface and a bottom surface, said i) top surface comprises a first layer comprising living stromal cells, a second layer positioned on top of said first layer and comprising living epithelial cells, said ii) bottom surface comprising living endothelial cells; and 2) introducing said living tumor cells into said microfluidic device under conditions such that at least a portion of said living tumor cells contact with said epithelial cells. In one embodiment, the method further comprises 3) incubating said living tumor cells in said microfluidic device, and 4) determining whether said tumor cells invade said cell layers. In one embodiment, said tumor cells are from a biopsy. In one embodiment, said tumor cells are human tumor cells.

In yet another embodiment, the present invention contemplates a microfluidic device comprising a gel and/or a membrane, said gel or membrane comprising a top surface and a bottom surface, said a) top surface comprises living epithelial cells, and living tumor cells in contact with said epithelial cells (or are in close proximity), said b) bottom surface comprising living endothelial cells. In one embodiment, said membrane is coated with at least one attachment molecule (e.g. ECM protein) that supports adhesion of a plurality of living cells. In one embodiment, the membrane separates first and second central microchannels. In one embodiment, the microfluidic device comprises i) a chamber, said chamber comprising a lumen and (optionally) projections into the lumen, said lumen comprising ii) a gel matrix (optionally anchored by said projections), said gel matrix positioned above iii) a porous membrane, said membrane positioned above iv) fluidic channels. Both the first and second central microchannels (mentioned earlier) and the fluidic channels (mentioned above) may comprise fluid. In one embodiment, said gel matrix is under a removable cover. In one embodiment, at least a portion of said gel matrix is patterned. In one embodiment, said gel matrix comprises collagen. In one embodiment, said gel matrix is between 0.2 and 6 mm in thickness.

It is not intended that the present invention be limited by the nature or source of the tumor cells. In one embodiment, said tumor cells are from a biopsy. In one embodiment, said tumor cells are mammalian tumor cells. In one embodiment, said tumor cells are human tumor cells. Additional cells can also be included. For example, in one embodiment, the top surface further comprises a first layer comprising living stromal cells, wherein said living epithelial cells comprise a second layer positioned on top of said first layer. As another example, in one embodiment, said tumor cells are also in contact with at least one type of immune cell (or in close proximity). A variety of immune cell types can be used. In one embodiment, said tumor cells are in contact with lymphocytes (or in close proximity), including but not limited to tumor cells are in contact with T cells (which can be naïve or primed T cells). In one embodiment, said tumor cells are in contact with activated dendritic cells (or in close proximity).

In yet another embodiment, the present invention contemplates a system comprising first and second microfluidic devices in fluidic communication, said a) first microfluidic device comprising a gel and/or a membrane, said gel or membrane comprising a top surface and a bottom surface, said i) top surface comprises living epithelial cells, and living tumor cells in contact with said epithelial cells (or in close proximity), said ii) bottom surface comprising living endothelial cells; said b) second microfluidic device comprising immune cells. In one embodiment, the first microfluidic device comprise a membrane, said membrane coated with at least one attachment molecule (e.g. ECM protein) that supports adhesion of a plurality of living cells. In one embodiment, the membrane separates first and second central microchannels. In one embodiment, the first microfluidic device comprises i) a chamber, said chamber comprising a lumen and (optionally) projections into the lumen, said lumen comprising ii) a gel matrix (optionally anchored by said projections), said gel matrix positioned above iii) a porous membrane, said membrane positioned above iv) fluidic channels. Both the first and second central micro channels (mentioned earlier) and the fluidic channels (mentioned above) may comprise fluid. In one embodiment, said gel matrix of said first microfluidic device is under a removable cover. In one embodiment, at least a portion of said gel matrix is patterned. In one embodiment, said gel matrix comprises collagen. In one embodiment, said gel matrix is between 0.2 and 6 mm in thickness.

Again, it is not intended that the present invention be limited by the nature or source of the tumor cells. In one embodiment, said tumor cells are from a biopsy. In one embodiment, said tumor cells are mammalian tumor cells. In one embodiment, said tumor cells are human tumor cells. Additional cells can also be included. For example, in one embodiment, the top surface further comprises a first layer comprising living stromal cells, wherein said living epithelial cells comprise a second layer positioned on top of said first layer. As another example, in one embodiment, said tumor cells are also in contact with at least one type of immune cell (or in close proximity). A variety of immune cell types can be used. In one embodiment, said tumor cells are in contact with lymphocytes (or in close proximity), including but not limited to tumor cells are in contact with T cells (which can be naïve or primed T cells. In one embodiment, said tumor cells are in contact with activated dendritic cells (or in close proximity).

In still another embodiment, the present invention contemplates a system comprising first, second and third microfluidic devices in fluidic communication with each other, said a) first microfluidic device comprising a gel and/or a membrane, the gel or membrane comprising a top surface and a bottom surface, said i) top surface comprising living epithelial cells, and living tumor cells in contact with said epithelial cells (or in close proximity), said ii) bottom surface comprising living endothelial cells; said b) second microfluidic device comprising immune cells; and said c) third microfluidic device comprising cells of an organ selected from the group consisting of cells of liver, kidney, lung, colon, intestine, and brain. In one embodiment, the first microfluidic device comprise a membrane, said membrane coated with at least one attachment molecule (e.g. ECM protein) that supports adhesion of a plurality of living cells. In one embodiment, the membrane separates first and second central microchannels. In one embodiment, the first microfluidic device comprises i) a chamber, said chamber comprising a lumen and (optionally) projections into the lumen, said lumen comprising ii) a gel matrix (optionally anchored by said projections), said gel matrix positioned above iii) a porous membrane, said membrane positioned above iv) fluidic channels. Both the first and second central micro channels (mentioned earlier) and the fluidic channels (mentioned above) may comprise fluid. In one embodiment, said gel matrix of said first microfluidic device is under a removable cover. In one embodiment, at least a portion of said gel matrix is patterned. In one embodiment, said gel matrix comprises collagen. In one embodiment, said gel matrix is between 0.2 and 6 mm in thickness.

Again, it is not intended that the present invention be limited by the nature or source of the tumor cells. In one embodiment, said tumor cells are from a biopsy. In one embodiment, said tumor cells are mammalian tumor cells. In one embodiment, said tumor cells are human tumor cells. Additional cells can also be included. For example, in one embodiment, the top surface further comprises a first layer comprising living stromal cells, wherein said living epithelial cells comprise a second layer positioned on top of said first layer. As another example, in one embodiment, said tumor cells are also in contact with at least one type of immune cell (or in close proximity). A variety of immune cell types can be used. In one embodiment, said tumor cells are in contact with lymphocytes (or in close proximity), including but not limited to tumor cells are in contact with T cells (which can be naïve or primed T cells. In one embodiment, said tumor cells are in contact with activated dendritic cells (or in close proximity).

In yet another embodiment, the present invention contemplates a method comprising: 1) providing a) immune cells and b) a microfluidic device comprising a gel and/or membrane, the gel or membrane comprising a top surface and a bottom surface, said i) top surface comprising living epithelial cells, and living tumor cells in contact with said epithelial cells (or in close proximity), said ii) bottom surface comprising living endothelial cells; and 2) introducing said immune cells into said microfluidic device under conditions such that at least a portion of said immune cells contact said tumor cells. In one embodiment, the microfluidic device comprises a membrane, said membrane coated with at least one attachment molecule (e.g. ECM protein) that supports adhesion of a plurality of living cells. In one embodiment, the membrane separates first and second central microchannels. In one embodiment, the microfluidic device comprises i) a chamber, said chamber comprising a lumen and (optionally) projections into the lumen, said lumen comprising ii) a gel matrix (optionally anchored by said projections), said gel matrix positioned above iii) a porous membrane, said membrane positioned above iv) fluidic channels. Both the first and second central microchannels (mentioned earlier) and the fluidic channels (mentioned above) may comprise fluid. In one embodiment, said gel matrix of said first microfluidic device is under a removable cover. In one embodiment, at least a portion of said gel matrix is patterned. In one embodiment, said gel matrix comprises collagen. In one embodiment, said gel matrix is between 0.2 and 6 mm in thickness.

Again, it is not intended that the present invention be limited by the nature or source of the tumor cells. In one embodiment, said tumor cells are from a biopsy. In one embodiment, said tumor cells are mammalian tumor cells. In one embodiment, said tumor cells are human tumor cells. Additional cells can also be included. For example, in one embodiment, the top surface further comprises a first layer comprising living stromal cells, wherein said living epithelial cells comprise a second layer positioned on top of said first layer. As another example, in one embodiment, said tumor cells are also in contact with at least one type of immune cell (or in close proximity). A variety of immune cell types can be used. In one embodiment, said tumor cells are in contact with lymphocytes (or in close proximity), including but not limited to tumor cells are in contact with T cells (which can be naïve or primed T cells. In one embodiment, said tumor cells are in contact with activated dendritic cells (or in close proximity).

It is not intended that the present invention be limited by the nature, type or preparation of immune cells. In one embodiment, said immune cells are introduced in step 2) of the above-described method in blood. In another embodiment, said immune cells are introduced in step 2) in culture media. In one embodiment, the culture media flows as a flow rate.

In one embodiment, the above-described method has the further step of 3) introducing one or more agents (e.g. candidate drugs, known anti-cancer drugs, known checkpoint inhibitors and candidate checkpoint inhibitors) into said microfluidic device. In one embodiment, the checkpoint inhibitor is an antibody. In one embodiment, said antibody binds the PD-1 receptor on T cells. In one embodiment, said antibody binds the PD-L1 ligand on the tumor cells. In one embodiment, the method has the further step of 4) detecting (and/or measuring) the impact of the agent on the tumor cells, e.g. detecting tumor cell death by immune cells or by the agent.

In still another embodiment, the present invention contemplates a method comprising: 1) providing a) a first microfluidic device comprising immune cells, said first microfluidic device in fluidic communication with b) a second microfluidic device comprising a gel and/or membrane, the gel membrane comprising a top surface and a bottom surface, said i) top surface comprising living epithelial cells, and living tumor cells in contact with said epithelial cells (or in close proximity), said ii) bottom surface comprising living endothelial cells; and 2) causing (at least a portion of) said immune cells in said first microfluidic device to move into said second microfluidic device under conditions such that at least a portion of said immune cells contact said tumor cells. It is not intended that the method be limited to how the immune cells are caused to move. In one embodiment, the immune cells are exposed to culture fluid at a flow rate. In one embodiment, said immune cells are exposed to one or more cytokines thereby causing said immune cells to move into said second microfluidic device. In one embodiment, fluidic communication is achieved through a conduit selected from the group consisting of a channel, a tube, or bridge, said conduit comprising fluid. In one embodiment, the second microfluidic device comprises a membrane, said membrane coated with at least one attachment molecule (e.g. ECM protein) that supports adhesion of a plurality of living cells. In one embodiment, the membrane separates first and second central microchannels. In one embodiment, the second microfluidic device comprises i) a chamber, said chamber comprising a lumen and (optionally) projections into the lumen, said lumen comprising ii) a gel matrix (optionally anchored by said projections), said gel matrix positioned above iii) a porous membrane, said membrane positioned above iv) fluidic channels. Both the first and second central microchannels (mentioned earlier) and the fluidic channels (mentioned above) may comprise fluid. In one embodiment, said gel matrix of said first microfluidic device is under a removable cover. In one embodiment, at least a portion of said gel matrix is patterned. In one embodiment, said gel matrix comprises collagen. In one embodiment, said gel matrix is between 0.2 and 6 mm in thickness.

Again, it is not intended that the present invention be limited by the nature or source of the tumor cells. In one embodiment, said tumor cells are from a biopsy. In one embodiment, said tumor cells are mammalian tumor cells. In one embodiment, said tumor cells are human tumor cells. Additional cells can also be included. For example, in one embodiment, the top surface further comprises a first layer comprising living stromal cells, wherein said living epithelial cells comprise a second layer positioned on top of said first layer. As another example, in one embodiment, said tumor cells are also in contact with at least one type of immune cell (or in close proximity). A variety of immune cell types can be used. In one embodiment, said tumor cells are in contact with lymphocytes (or in close proximity), including but not limited to tumor cells are in contact with T cells (which can be naïve or primed T cells). In one embodiment, said tumor cells are in contact with activated dendritic cells (or in close proximity).

It is not intended that the present invention be limited by the nature, type or preparation of immune cells. In one embodiment, said immune cells are in blood. In another embodiment, said immune cells are in culture media. In one embodiment, the culture media flows as a flow rate.

In one embodiment, the above-described method has the further step of 3) introducing one or more agents (e.g. candidate drugs, known anti-cancer drugs, known checkpoint inhibitors and candidate checkpoint inhibitors) into said microfluidic device. In one embodiment, the checkpoint inhibitor is an antibody. In one embodiment, said antibody binds the PD-1 receptor on T cells. In one embodiment, said antibody binds the PD-L1 ligand on the tumor cells. In one embodiment, the method has the further step of 4) detecting (and/or measuring) the impact of the agent on the tumor cells, e.g. detecting tumor cell death by immune cells or by the agent.

In still another embodiment, the present invention contemplates a method comprising: 1) providing a) a first microfluidic device comprising immune cells, said first microfluidic device in fluidic communication with b) a second microfluidic device and c) a third microfluidic device, said second microfluidic device comprising a gel and/or membrane, the gel or membrane comprising a top surface and a bottom surface, said i) top surface comprising living epithelial cells, and living tumor cells in contact with said epithelial cells (or in close proximity), said ii) bottom surface comprising living endothelial cells; said third microfluidic device comprising cells of an organ selected from the group consisting of cells of liver, kidney, lung, colon, intestine, brain; and 2) causing said immune cells in said first microfluidic device to move into said second microfluidic device under conditions such that at least a portion of said immune cells contact said tumor cells (or are in close proximity). It is not intended that the method be limited to how the immune cells are caused to move. In one embodiment, the immune cells are exposed to culture fluid at a flow rate. In one embodiment, said immune cells are exposed to one or more cytokines thereby causing said immune cells to move into said second microfluidic device. In one embodiment, fluidic communication is achieved through a conduit selected from the group consisting of a channel, a tube, or bridge, said conduit comprising fluid. In one embodiment, the second microfluidic device comprises a membrane, said membrane coated with at least one attachment molecule (e.g. ECM protein) that supports adhesion of a plurality of living cells. In one embodiment, the membrane separates first and second central microchannels. In one embodiment, the second microfluidic device comprises i) a chamber, said chamber comprising a lumen and (optionally) projections into the lumen, said lumen comprising ii) a gel matrix (optionally anchored by said projections), said gel matrix positioned above iii) a porous membrane, said membrane positioned above iv) fluidic channels. Both the first and second central microchannels (mentioned earlier) and the fluidic channels (mentioned above) may comprise fluid. In one embodiment, said gel matrix of said second microfluidic device is under a removable cover. In one embodiment, at least a portion of said gel matrix is patterned. In one embodiment, said gel matrix comprises collagen. In one embodiment, said gel matrix is between 0.2 and 6 mm in thickness.

Again, it is not intended that the present invention be limited by the nature or source of the tumor cells. In one embodiment, said tumor cells are from a biopsy. In one embodiment, said tumor cells are mammalian tumor cells. In one embodiment, said tumor cells are human tumor cells. Additional cells can also be included. For example, in one embodiment, the top surface further comprises a first layer comprising living stromal cells, wherein said living epithelial cells comprise a second layer positioned on top of said first layer. As another example, in one embodiment, said tumor cells are also in contact with at least one type of immune cell (or in close proximity). A variety of immune cell types can be used. In one embodiment, said tumor cells are in contact with lymphocytes (or in close proximity), including but not limited to tumor cells are in contact with T cells (which can be naïve or primed T cells). In one embodiment, said T cells are primed T cells, said priming taking place in said first microfluidic device. In one embodiment, said tumor cells are in contact with activated dendritic cells (or in close proximity).

It is not intended that the present invention be limited by the nature, type or preparation of immune cells. In one embodiment, said immune cells are in blood. In another embodiment, said immune cells are in culture media. In one embodiment, the culture media flows as a flow rate.

In one embodiment, the above-described method has the further step of 3) causing said immune cells in said first microfluidic device to move into said third microfluidic device under conditions such that at least a portion of said immune cells contact said tumor cells. In one embodiment, said third microfluidic device comprises tumor cells in contact with said cells of an organ (or in close proximity).

In one embodiment, the above-described method has the further step of 3) introducing one or more agents (e.g. candidate drugs, known anti-cancer drugs, known checkpoint inhibitors and candidate checkpoint inhibitors) into said microfluidic device. In one embodiment, the checkpoint inhibitor is an antibody. In one embodiment, said antibody binds the PD-1 receptor on T cells. In one embodiment, said antibody binds the PD-L1 ligand on the tumor cells. In one embodiment, the method has the further step of 4) detecting (and/or measuring) the impact of the agent on the tumor cells, e.g. detecting tumor cell death by immune cells or by the agent.

In yet another embodiment, the present invention contemplates a method comprising: 1) providing a) living tumor cells and b) a microfluidic device comprising a gel and/or membrane, the gel or membrane comprising a top surface and a bottom surface, said i) top surface comprising living epithelial cells, said ii) bottom surface comprising living endothelial cells; and 2) introducing said living tumor cells into said microfluidic device under conditions such that at least a portion of said living tumor cells contact with said epithelial cells. In one embodiment, the method has the further steps of 3) incubating said living tumor cells in said microfluidic device, and 4) determining whether said tumor cells invade said cell layers. In one embodiment, the method has the further steps of 3) introducing immune cells in said microfluidic device, and 4) determining whether said immune cells cause tumor cell death. In one embodiment, the above-described method has the further step of 3) introducing one or more agents (e.g. candidate drugs, known anti-cancer drugs, known checkpoint inhibitors and candidate checkpoint inhibitors) into said microfluidic device. In one embodiment, the checkpoint inhibitor is an antibody. In one embodiment, said antibody binds the PD-1 receptor on T cells. In one embodiment, said antibody binds the PD-L1 ligand on the tumor cells. In one embodiment, the method has the further step of 4) detecting (and/or measuring) the impact of the agent on the tumor cells, e.g. detecting tumor cell death by immune cells or by the agent.

In one embodiment, the microfluidic device comprises a membrane, said membrane coated with at least one attachment molecule (e.g. ECM protein) that supports adhesion of a plurality of living cells. In one embodiment, the membrane separates first and second central microchannels. In one embodiment, the microfluidic device comprises i) a chamber, said chamber comprising a lumen and (optionally) projections into the lumen, said lumen comprising ii) a gel matrix (optionally anchored by said projections), said gel matrix positioned above iii) a porous membrane, said membrane positioned above iv) fluidic channels. Both the first and second central microchannels (mentioned earlier) and the fluidic channels (mentioned above) may comprise fluid. In one embodiment, said gel matrix of said microfluidic device is under a removable cover. In one embodiment, at least a portion of said gel matrix is patterned. In one embodiment, said gel matrix comprises collagen. In one embodiment, said gel matrix is between 0.2 and 6 mm in thickness.

Again, it is not intended that the present invention be limited by the nature or source of the tumor cells. In one embodiment, said tumor cells are from a biopsy. In one embodiment, said tumor cells are mammalian tumor cells. In one embodiment, said tumor cells are human tumor cells. Additional cells can also be included. For example, in one embodiment, the top surface further comprises a first layer comprising living stromal cells, wherein said living epithelial cells comprise a second layer positioned on top of said first layer. As another example, in one embodiment, said tumor cells are also in contact with at least one type of immune cell (or in close proximity). A variety of immune cell types can be used. In one embodiment, said tumor cells are in contact with lymphocytes (or in close proximity), including but not limited to tumor cells are in contact with T cells (which can be naïve or primed T cells). In one embodiment, said tumor cells are in contact with activated dendritic cells (or in close proximity).

In still another embodiment, the present invention contemplates a microfluidic device comprising: a body having a first channel and a first chamber; an at least partially porous membrane positioned at an interface region between the first a channel and the first chamber, the membrane comprising a top surface and a bottom surface, said top surface facing the first chamber; living parenchymal cells disposed within the first chamber; and living tumor cells disposed within at least one of the first chamber or the first channel. In one embodiment, the first chamber comprises a second channel. In one embodiment, the first chamber comprises an open region. In one embodiment, said living parenchymal cells comprise living epithelial cells. In one embodiment, the device further comprises endothelial cells disposed within the first channel. In one embodiment, the living tumor cells are in contact with said parenchymal cells. In one embodiment, the living tumor cells are in contact with said endothelial cells. In one embodiment, said membrane is coated with at least one attachment molecule that supports adhesion of a plurality of living cells. In one embodiment, said first channel comprises fluid. In one embodiment, said tumor cells are from a biopsy. In one embodiment, said tumor cells are human tumor cells. In one embodiment, the device further comprises living stromal cells disposed within the first chamber. In one embodiment, said living stromal cells are disposed in contact with the said top surface of the said membrane. In one embodiment, said living stromal cells are disposed within a gel. In one embodiment, said epithelial cells comprise a first layer positioned on top of said living stromal cells. In one embodiment, said stromal cells were derived from (or originated from) the site of a tumor. In one embodiment, said stromal cells were derived from a site away from a tumor. In one embodiment, said stromal cells were derived from a tumor-free sample. In one embodiment, the device further comprises at least one immune cell of at least one immune cell type. In one embodiment, said at least one immune cell is in contact with said tumor cells. In one embodiment, said at least one immune cell type is lymphocytes. In one embodiment, said at least one immune cell type is T cells. In one embodiment, said T cells are primed T cells. In one embodiment, said at least one immune cell type is dendritic cells. In one embodiment, said at least one immune cell was derived from (or originates from) within a tumor. In one embodiment, said at least one immune cell was derived from the proximity of a tumor. In one embodiment, said at least one immune cell was derived away from the proximity of a tumor. In one embodiment, said at least one immune cell was derived from a tumor-free sample. In one embodiment, said at least one immune cell was derived from peripheral blood. In one embodiment, said tumor cells comprise at least one cell type corresponding to the organ type represented (i.e. not metastasized) by at least some of the said parenchymal cells. In one embodiment, said tumor cells do not correspond (e.g. metastatic tumor) to the organ type represented by said parenchymal cells.

In yet another embodiment, the present invention contemplates a system comprising first and second microfluidic devices in fluidic communication, said a) first microfluidic device comprising a body having a first channel and a first chamber; an at least partially porous membrane positioned at an interface region between the first a channel and the first chamber, the membrane comprising a top surface and a bottom surface, said top surface facing the first chamber; living parenchymal cells disposed within the first chamber; and living tumor cells disposed within at least one of the first chamber or the first channel; said b) second microfluidic device comprising immune cells. In one embodiment, said membrane is coated with at least one attachment molecule that supports adhesion of a plurality of living cells. In one embodiment, said first and second central microchannels of said first microfluidic device comprise fluid. In one embodiment, said tumor cells are from a biopsy. In one embodiment, said tumor cells are human tumor cells. In one embodiment, the top surface further comprises a first layer comprising living stromal cells, wherein said living epithelial cells comprise a second layer positioned on top of said first layer. In one embodiment, said tumor cells are also in contact with at least one type of immune cell. In one embodiment, said tumor cells are in contact with lymphocytes. In one embodiment, said tumor cells are in contact with T cells. In one embodiment, said T cells are primed T cells. In one embodiment, said tumor cells are in contact with activated dendritic cells. further comprising c) a third microfluidic device comprising cells of an organ selected from the group consisting of cells of liver, kidney, lung, colon, intestine, and brain.

In still another embodiment, the present invention contemplates a method comprising: 1) providing a) an agent and b) a microfluidic device comprising: a body having a first channel and a first chamber; an at least partially porous membrane positioned at an interface region between the first channel and the first chamber, the membrane comprising a top surface and a bottom surface, said top surface facing the first chamber; living parenchymal cells disposed within the first chamber; and living tumor cells disposed within at least one of the first chamber or the first channel; and 2) introducing said agent into said microfluidic device. In one embodiment, the first chamber comprises a second channel. In one embodiment, the first chamber comprises an open region. In one embodiment, said living parenchymal cells comprise living epithelial cells. In one embodiment, the method further comprises endothelial cells disposed within the first channel. In one embodiment, the living tumor cells are in contact with said parenchymal cells. In one embodiment, the living tumor cells are in contact with said endothelial cells. In one embodiment, said tumor cells are from a biopsy. In one embodiment, said tumor cells are human tumor cells. In one embodiment, the method further comprises living stromal cells disposed within the first chamber. In one embodiment, said living stromal cells are disposed in contact with the said top surface of said membrane. In one embodiment, said living stromal cells are disposed within a gel. In one embodiment, said epithelial cells comprise a first layer positioned on top of said living stromal cells. In one embodiment, said stromal cells were derived from the site of a tumor. In one embodiment, said stromal cells were derived from a site away from a tumor. In one embodiment, said stromal cells were derived from a tumor-free sample. In one embodiment, the method further comprises at least one immune cell of at least one immune cell type. In one embodiment, the at least one immune cell is in contact with said tumor cells. In one embodiment, said at least one immune cell type is lymphocytes. In one embodiment, said at least one immune cell type is T cells. In one embodiment, said T cells are primed T cells. In one embodiment, said at least one immune cell type is dendritic cells. In one embodiment, said at least one immune cell was derived from within a tumor. In one embodiment, said at least one immune cell was derived from the proximity of a tumor. In one embodiment, said at least one immune cell was derived away from the proximity of a tumor. In one embodiment, said at least one immune cell was derived from a tumor-free sample. In one embodiment, said at least one immune cell was derived from peripheral blood. In one embodiment, said tumor cells comprise at least one cell type corresponding to the organ type represented by at least some of the said parenchymal cells. In one embodiment, said tumor cells do not correspond to the organ type represented by said parenchymal cells. In one embodiment, agent comprises a drug. In one embodiment, said agent comprises at least one of a toxin, a pollutant, a chemical, a cosmetic. In one embodiment, said agent comprises a cell. In one embodiment, said cell is an immune cell. In one embodiment, said immune cell is a T cell. In one embodiment, said T cell is a CAR-T cell. In one embodiment, said agent comprises an immunotherapy agent. In one embodiment, said agent comprises a chemotherapy agent. In one embodiment, said agent comprises a checkpoint inhibitor. In one embodiment, said agent comprises an antibody. In one embodiment, said agent comprises at least one of anti-PD-1 or anti-PD-L1. In one embodiment, the method further comprises 3) observing a response. In one embodiment, said observing a response comprises detecting the death of at least some of said tumor cells. In one embodiment, said observing a response comprises evaluating at least one of tumor size, tumor cell number, tumor metabolic activity, and tumor growth rate. In one embodiment, said observing a response comprises evaluating at least one of non-tumor cell death and non-tumor cell growth rate.

In still another embodiment, the present invention contemplates a method comprising: 1) providing a) immune cells and b) a microfluidic device comprising a body having a first channel and a first chamber, an at least partially porous membrane positioned at an interface region between the first a channel and the first chamber, the membrane comprising a top surface and a bottom surface, said top surface facing the first chamber, living parenchymal cells disposed within the first chamber; and living tumor cells disposed within at least one of the first chamber or the first channel; and 2) introducing said immune cells into said microfluidic device. In one embodiment, said membrane is coated with at least one attachment molecule that supports adhesion of a plurality of living cells. In one embodiment, said first and second central microchannels comprise fluid. In one embodiment, said tumor cells are from a biopsy. In one embodiment, said tumor cells are human tumor cells. In one embodiment, said immune cells are introduced in step 2) in blood. In one embodiment, the top surface further comprises a first layer comprising living stromal cells, wherein said living epithelial cells comprise a second layer positioned on top of said first layer. In one embodiment, said immune cells comprise lymphocytes and said tumor cells are in contact with lymphocytes. In one embodiment, said lymphocytes comprise T cells. In one embodiment, said T cells are primed T cells. In one embodiment, said immune cells comprise activated dendritic cells and said tumor cells are in contact with dendritic cells. In one embodiment, further comprising 3) introducing a checkpoint inhibitor into said microfluidic device. In one embodiment, said checkpoint inhibitor is an antibody. In one embodiment, said antibody binds the PD-1 receptor. In one embodiment, said antibody binds the PD-L1 ligand. In one embodiment, the method further comprises 4) detecting tumor cell death.

In still another embodiment, the present invention contemplates a method comprising: 1) providing a) a first microfluidic device comprising immune cells, said first microfluidic device in fluidic communication with b) a second microfluidic device comprising a body having a first channel and a first chamber, an at least partially porous membrane positioned at an interface region between the first a channel and the first chamber, the membrane comprising a top surface and a bottom surface, said top surface facing the first chamber, living parenchymal cells disposed within the first chamber; and living tumor cells disposed within at least one of the first chamber or the first channel; and 2) causing said immune cells in said first microfluidic device to move into said second microfluidic device. In one embodiment, said immune cells are exposed to one or more cytokines thereby causing said immune cells to move into said second microfluidic device. In one embodiment, said fluidic communication is achieved at least in part through a conduit selected from the group consisting of a channel, a tube, or bridge, said conduit comprising fluid. In one embodiment, said fluidic communication is achieved at least in part through discrete fluid transfers. In one embodiment, at least some of said discrete fluidic transfer are performed by at least one of a liquid-handling robot and autosampler. In one embodiment, said tumor cells are from a biopsy. In one embodiment, said tumor cells are human tumor cells. In one embodiment, said immune cells of step 2) are in blood. In one embodiment, said immune cells comprise lymphocytes. In one embodiment, said lymphocytes comprise T cells. In one embodiment, the method further comprises 3) introducing a checkpoint inhibitor into said microfluidic device. In one embodiment, said checkpoint inhibitor is an antibody. In one embodiment, said antibody binds the PD-1 receptor. In one embodiment, said antibody binds the PD-L1 ligand. In one embodiment, the method further comprises 3) detecting tumor cell death. In one embodiment, said T cells are primed T cells, said priming taking place in said first microfluidic device. In one embodiment, said immune cells comprise activated dendritic cells and said tumor cells are in contact with activated dendritic cells. In one embodiment, the top surface further comprises a first layer comprising living stromal cells, wherein said living epithelial cells comprise a second layer positioned on top of said first layer. In one embodiment, the method further comprises providing c) a third microfluidic device in fluidic communication with at least one of the first and second microfluidic devices.

In still another embodiment, the present invention contemplates a method comprising: providing a) living tumor cells and b) a microfluidic device comprising a body having a first channel and a first chamber, an at least partially porous membrane positioned at an interface region between the first a channel and the first chamber, the membrane comprising a top surface and a bottom surface, said top surface facing the first chamber, living parenchymal cells disposed within the first chamber; and living tumor cells disposed within at least one of the first chamber or the first channel. In one embodiment, the method further comprises 3) incubating said living tumor cells in said microfluidic device, and 4) determining whether said tumor cells invade said cell layers. In one embodiment, said tumor cells are from a biopsy. In one embodiment, said tumor cells are human tumor cells. In one embodiment, the method further comprises 3) introducing immune cells into said microfluidic device. In one embodiment, the method further comprises 4) evaluating at least one of tumor growth rate, tumor size, and tumor cell death, and non-tumor cell death. In one embodiment, the method further comprises 3) introducing an agent into said microfluidic device. In one embodiment, the method further comprising 4) evaluating at least one of tumor growth rate, tumor size, tumor cell death, and non-tumor cell death. In one embodiment, said agent comprises at least one of a drug, a toxin, a chemotherapy agent, an immunoncology agent, a checkpoint inhibitor, a chemical, and a cosmetic. In one embodiment, said agent is an antibody. In one embodiment, said antibody binds the PD-1 receptor. In one embodiment, said antibody binds the PD-L1 ligand. In some embodiments, the method involves additional cells on the device, such as stromal cells and/or endothelial cells. In one embodiment, the top surface further comprises a first layer comprising living stromal cells, wherein said living epithelial cells comprise a second layer positioned on top of said first layer. In one embodiment, the tumor cells may enter stroma. In one embodiment, the method further comprises endothelial cell disposed in the device. In one embodiment, said tumor cells grow on said endothelial cells.

In still another embodiment, the present invention contemplates a microfluidic device comprising: a body having a central microchannel therein; and an at least partially porous membrane positioned within the central microchannel, the membrane configured to separate the central microchannel to form a first central microchannel and a second central microchannel, the membrane comprising a top surface and a bottom surface, said a) top surface comprises living epithelial cells, and living tumor cells in contact with said epithelial cells, said b) bottom surface comprising living endothelial cells. In one embodiment, said membrane is coated with at least one attachment molecule that supports adhesion of a plurality of living cells. In one embodiment, said first and second central microchannels comprise fluid. In one embodiment, said tumor cells are from a biopsy. In one embodiment, said tumor cells are mammalian tumor cells. In one embodiment, said tumor cells are human tumor cells. In one embodiment, the top surface further comprises a first layer comprising living stromal cells, wherein said living epithelial cells comprise a second layer positioned on top of said first layer. In one embodiment, said tumor cells are also in contact with at least one type of immune cell. In one embodiment, said tumor cells are in contact with lymphocytes. In one embodiment, said tumor cells are in contact with T cells. In one embodiment, said T cells are primed T cells. In one embodiment, said tumor cells are in contact with activated dendritic cells.

In still another embodiment, the present invention contemplates a system comprising first and second microfluidic devices in fluidic communication, said a) first microfluidic device comprising a body having a central microchannel therein; and an at least partially porous membrane positioned within the central microchannel, the membrane configured to separate the central microchannel to form a first central microchannel and a second central microchannel, the membrane comprising a top surface and a bottom surface, said i) top surface comprises living epithelial cells, and living tumor cells in contact with said epithelial cells, said ii) bottom surface comprising living endothelial cells; said b) second microfluidic device comprising immune cells. In one embodiment, said membrane is coated with at least one attachment molecule that supports adhesion of a plurality of living cells. In one embodiment, said first and second central microchannels of said first microfluidic device comprise fluid. In one embodiment, said tumor cells are from a biopsy. In one embodiment, said tumor cells are mammalian tumor cells. In one embodiment, said tumor cells are human tumor cells. In one embodiment, the top surface further comprises a first layer comprising living stromal cells, wherein said living epithelial cells comprise a second layer positioned on top of said first layer. In one embodiment, said tumor cells are also in contact with at least one type of immune cell. In one embodiment, said tumor cells are in contact with lymphocytes. In one embodiment, said tumor cells are in contact with T cells. In one embodiment, said T cells are primed T cells. In one embodiment, said tumor cells are in contact with activated dendritic cells.

In still another embodiment, the present invention contemplates a system comprising first, second and third microfluidic devices in fluidic communication, said a) first microfluidic device comprising a body having a central microchannel therein; and an at least partially porous membrane positioned within the central microchannel, the membrane configured to separate the central microchannel to form a first central microchannel and a second central microchannel, the membrane comprising a top surface and a bottom surface, said i) top surface comprising living epithelial cells, and living tumor cells in contact with said epithelial cells, said ii) bottom surface comprising living endothelial cells; said b) second microfluidic device comprising immune cells; and said c) third microfluidic device comprising cells of an organ selected from the group consisting of cells of liver, kidney, lung, colon, intestine, skin and brain. In one embodiment, said membrane is coated with at least one attachment molecule that supports adhesion of a plurality of living cells. In one embodiment, said first and second central microchannels of said first microfluidic device comprise fluid. In one embodiment, said tumor cells are from a biopsy. In one embodiment, said tumor cells are mammalian tumor cells. In one embodiment, said tumor cells are human tumor cells. the top surface further comprises a first layer comprising living stromal cells, wherein said living epithelial cells comprise a second layer positioned on top of said first layer. In one embodiment, said tumor cells are also in contact with at least one type of immune cell. In one embodiment, said tumor cells are in contact with lymphocytes. In one embodiment, said tumor cells are in contact with T cells. In one embodiment, said T cells are primed T cells. In one embodiment, said tumor cells are in contact with activated dendritic cells.

In still another embodiment, the present invention contemplates a method comprising: 1) providing a) immune cells and b) a microfluidic device comprising a body having a central microchannel therein; and an at least partially porous membrane positioned within the central microchannel, the membrane configured to separate the central microchannel to form a first central microchannel and a second central microchannel, the membrane comprising a top surface and a bottom surface, said i) top surface comprising living epithelial cells, and living tumor cells in contact with said epithelial cells, said ii) bottom surface comprising living endothelial cells; and 2) introducing said immune cells into said microfluidic device under conditions such that at least a portion of said immune cells contact said tumor cells. In one embodiment, said membrane is coated with at least one attachment molecule that supports adhesion of a plurality of living cells. In one embodiment, said first and second central microchannels comprise fluid. In one embodiment, said tumor cells are from a biopsy. In one embodiment, said tumor cells are mammalian tumor cells. In one embodiment, said tumor cells are human tumor cells. In one embodiment, said immune cells are introduced in step 2) in blood. In one embodiment, the top surface further comprises a first layer comprising living stromal cells, wherein said living epithelial cells comprise a second layer positioned on top of said first layer. In one embodiment, said immune cells comprise lymphocytes and said tumor cells are in contact with lymphocytes. In one embodiment, said lymphocytes comprise T cells. In one embodiment, said T cells are primed T cells. In one embodiment, said immune cells comprise activated dendritic cells and said tumor cells are in contact with activated dendritic cells. In one embodiment, the method further comprises 3) introducing a checkpoint inhibitor into said microfluidic device. In one embodiment, said checkpoint inhibitor is an antibody. In one embodiment, said antibody binds the PD-1 receptor on T cells. In one embodiment, said antibody binds the PD-L1 ligand on the tumor cells. In one embodiment, further comprising 4) detecting tumor cell death.

In still another embodiment, the present invention contemplates a method comprising: 1) providing a) a first microfluidic device comprising immune cells, said first microfluidic device in fluidic communication with b) a second microfluidic device comprising a body having a central microchannel therein; and an at least partially porous membrane positioned within the central microchannel, the membrane configured to separate the central microchannel to form a first central microchannel and a second central microchannel, the membrane comprising a top surface and a bottom surface, said i) top surface comprising living epithelial cells, and living tumor cells in contact with said epithelial cells, said ii) bottom surface comprising living endothelial cells; and 2) causing said immune cells in said first microfluidic device to move into said second microfluidic device under conditions such that at least a portion of said immune cells contact said tumor cells. In one embodiment, said immune cells are exposed to one or more cytokines thereby causing said immune cells to move into said second microfluidic device. In one embodiment, fluidic communication is achieved through a conduit selected from the group consisting of a channel, a tube, or bridge, said conduit comprising fluid. In one embodiment, said tumor cells are from a biopsy. In one embodiment, said tumor cells are mammalian tumor cells. In one embodiment, said tumor cells are human tumor cells. In one embodiment, said immune cells of step 2) are in blood. In one embodiment, said immune cells comprise lymphocytes and said tumor cells are in contact with lymphocytes. In one embodiment, said lymphocytes comprise T cells. In one embodiment, the method further comprises 3) introducing a checkpoint inhibitor into said microfluidic device. In one embodiment, said checkpoint inhibitor is an antibody. In one embodiment, said antibody binds the PD-1 receptor on said T cells. In one embodiment, said antibody binds the PD-L1 ligand on the tumor cells. In one embodiment, the method further comprises 4) detecting tumor cell death. In one embodiment, said T cells are primed T cells, said priming taking place in said first microfluidic device. In one embodiment, said immune cells comprise activated dendritic cells and said tumor cells are in contact with activated dendritic cells. In one embodiment, the top surface further comprises a first layer comprising living stromal cells, wherein said living epithelial cells comprise a second layer positioned on top of said first layer.

In still another embodiment, the present invention contemplates a method comprising: 1) providing a) a first microfluidic device comprising immune cells, said first microfluidic device in fluidic communication with b) a second microfluidic device and c) a third microfluidic device, said second microfluidic device comprising a body having a central microchannel therein; and an at least partially porous membrane positioned within the central microchannel, the membrane configured to separate the central microchannel to form a first central microchannel and a second central microchannel, the membrane comprising a top surface and a bottom surface, said i) top surface comprising living epithelial cells, and living tumor cells in contact with said epithelial cells, said ii) bottom surface comprising living endothelial cells; said third microfluidic device comprising cells of an organ selected from the group consisting of cells of liver, kidney, lung, colon, intestine, skin and brain; and 2) causing said immune cells in said first microfluidic device to move into said second microfluidic device under conditions such that at least a portion of said immune cells contact said tumor cells. In one embodiment, said immune cells are exposed to one or more cytokines in said first microfluidic device thereby causing said immune cells to move into said second microfluidic device. In one embodiment, fluidic communication is achieved through conduits, each conduit selected from the group consisting of a channel, a tube, or bridge, said conduit comprising fluid. In one embodiment, said tumor cells are from a biopsy. In one embodiment, said tumor cells are mammalian tumor cells. In one embodiment, said tumor cells are human tumor cells. In one embodiment, said immune cells of step 2) are in blood. In one embodiment, said immune cells comprise lymphocytes and said tumor cells are in contact with lymphocytes. In one embodiment, said lymphocytes comprise T cells. In one embodiment, said T cells are primed T cells, said priming taking place in said first microfluidic device. In one embodiment, said immune cells comprise activated dendritic cells and said tumor cells are in contact with activated dendritic cells. In one embodiment, said third microfluidic device comprises tumor cells in contact with said cells of an organ. In one embodiment, the method further comprises 3) causing said immune cells in said first microfluidic device to move into said third microfluidic device under conditions such that at least a portion of said immune cells contact said tumor cells. In one embodiment, the top surface further comprises a first layer comprising living stromal cells, wherein said living epithelial cells comprise a second layer positioned on top of said first layer.

In yet another embodiment, the present invention contemplates a method comprising: 1) providing a) living tumor cells and b) a microfluidic device comprising a body having a central microchannel therein; and an at least partially porous membrane positioned within the central microchannel, the membrane configured to separate the central microchannel to form a first central micro channel and a second central microchannel, the membrane comprising a top surface and a bottom surface, said i) top surface comprising living epithelial cells, said ii) bottom surface comprising living endothelial cells; and 2) introducing said living tumor cells into said microfluidic device under conditions such that at least a portion of said living tumor cells contact with said epithelial cells. In one embodiment, the method further comprises 3) incubating said living tumor cells in said microfluidic device, and 4) determining whether said tumor cells invade said cell layers. In one embodiment, said tumor cells are from a biopsy. In one embodiment, said tumor cells are mammalian tumor cells. In one embodiment, said tumor cells are human tumor cells. In one embodiment, the method further comprises 3) introducing immune cells in said microfluidic device, and 4) determining whether said immune cells cause tumor cell death. In one embodiment, the method further comprises 5) introducing a checkpoint inhibitor in said microfluidic device, and 6) determining whether said checkpoint inhibitor causes tumor cell death. In one embodiment, said checkpoint inhibitor is an antibody. In one embodiment, said antibody binds the PD-1 receptor on said T cells. In one embodiment, said antibody binds the PD-L1 ligand on the tumor cells. In one embodiment, the top surface further comprises a first layer comprising living stromal cells, wherein said living epithelial cells comprise a second layer positioned on top of said first layer.

In still another embodiment, the present invention contemplates a microfluidic device lacking tumor cells, comprising: a body having a gel or an at least partially porous membrane, the gel or membrane comprising a top surface and a bottom surface, said a) top surface comprises living epithelial cells but lacking tumor cells, said b) bottom surface comprising living endothelial cells but lacking tumor cells, wherein said top surface, bottom surface or both surfaces of said membrane or gel comprise at least one attachment molecule that supports adhesion of a plurality of living cells, wherein said at least one attachment molecule is derived from a tumor site of a patient. In one embodiment, said at least one attachment molecule is an extracellular matrix protein. In one embodiment, the method further comprises immune cells. In one embodiment, said immune cells are derived from a tumor site of a patient.

In still another embodiment, the present invention contemplates a method comprising: 1) providing a) immune cells derived from a tumor site of a patient, said immune cells lacking contaminating tumor cells; and b) a microfluidic device lacking tumor cells and comprising a gel or an at least partially porous membrane, said membrane or gel comprising a top surface and a bottom surface, said i) top surface comprising living epithelial cells, said ii) bottom surface comprising living endothelial cells; and 2) introducing said immune cells into said microfluidic device under conditions such that at least a portion of said immune cells contact said epithelial cells, said endothelial cells or both. In one embodiment, said membrane or gel comprises at least one attachment molecule that supports adhesion of a plurality of living cells. In one embodiment, said at least one attachment molecule is derived from a tumor site of a patient. In one embodiment, said at least one attachment molecule is an extracellular matrix protein.

BRIEF DESCRIPTION OF THE DRAWINGS

FIG. 2A: Shows an exemplary schematic illustration of embodiments of human and mouse Cancer-on-Chip Provides a Mechanistic Insight and a Bridge for Translation of treatments to humans. FIG. 2B: shows an exemplary colorized scanning electron micrograph of a tumor (purple) with attached immune cells (green).

FIG. 5B: The gas mixture changes the overall gas concentration in the system by controlling the gas concentration in media, ranging from 50-100% of the chosen gas, for one e.g. CO2.

FIG. 6A: Shows two examples of gradients that are formed by changing the input media gas concentration. Upper example shows media with low oxygen concentration limited to the upper part of the top channel while the lower example shows media with low oxygen concentration in the lower part of the top channel and in the bottom channel (see an exemplary gas key to the right). FIG. 6B: Show exemplary schematic illustrations of several embodiments for providing Hypoxia-on-Chip containing a tumor with three types of O2 concentrations, from left to right, high concentration, low concentration below, in the lower channel and in the lower part of the tumor, and in the right schematic a low gas environment for the entire tumor.

FIG. 7A: HuVEC-GFP forming tubular network around Collagen I Spheres. FIG. 7B: A higher power magnification of an area of A (10×) showing Collagen I spheres (blue arrows) and red arrows pointing to network formation.

FIG. 8A: HuVEC-GFP forming tubular network around Collagen I Spheres. FIG. 8B: A higher power magnification of the red outlined box area of A showing network formation.

FIG. 11A: Shows an exemplary schematic illustration of a circular format for a microfluidic channel, e.g. a bottom spiraled endothelial channel. FIG. 11B: Shows an exemplary schematic illustration of parts of a microfluidic chip (16) including a lower circular format for a circular microfluidic channel, a membrane, and an upper part of a chip. FIG. 11C: Shows an exemplary schematic illustration of an assembled microfluidic chip (16) showing a cross section of optional vacuum channels in the upper part of the chip.

FIG. 12A: Shows an exemplary schematic illustration of a circular format (geometry) for a microfluidic chip. FIG. 12B: Shows exemplary photographs of a side view (upper) and top view (lower) circular chip. FIG. 12C: Shows an exemplary schematic illustration of a rectangular format (geometry) for a microfluidic chip. FIG. 12D: Shows exemplary photograph of a top view of a rectangular chip.

FIG. 13A: An exemplary schematic illustration of one embodiment for Cancer-On-Chip. FIG. 13B: An exemplary photograph of Cancer-On-Chip shown in FIG. 13A. FIG. 13C: An exemplary photograph of Cancer-On-Chip shown in FIG. 13A attached to microfluidic connections.

FIG. 14A: An exemplary fluorescent micrograph showing cancer cells with MiTF positive-cells (green), nuclei (blue). In this view, cells express different levels of MiTF where in some cell clusters many cells are expressing high levels of MiTF (i.e. many light blue/green cells). FIG. 14B: An exemplary fluorescent micrograph showing cancer cells where in this view, few cells express MiTF (few light blue/green cells). FIG. 14C: An exemplary fluorescent micrograph showing exemplary heterogeneity of tumor cells. Cancer cells with MiTF positive-cells (green), nuclei (blue) where co-localized (combined channels) show light blue double stained nuclei of cancer cells.

FIG. 15A: Shows an exemplary micrograph of melanoma cells staining with the Melanoma Cocktail (green) and nuclei (blue) at 11 days post seeding of the tumor in the Cancer-On-Chip. FIG. 15B: Shows an exemplary micrograph of melanoma cells staining with a negative control using secondary antibodies but not the primary antibodies in the Melanoma Cocktail. Nuclei are shown in blue.

FIG. 16A: Shows an exemplary micrograph of a stained section where cells stained positive for Melanoma markers (green). FIG. 16B: Shows an exemplary higher power magnified micrograph of the area outlined in box 1 in FIG. 15A. FIG. 16C: Shows an exemplary higher power magnified micrograph of the area outlined in box 2 in FIG. 15A.

DEFINITIONS

Figure 1:
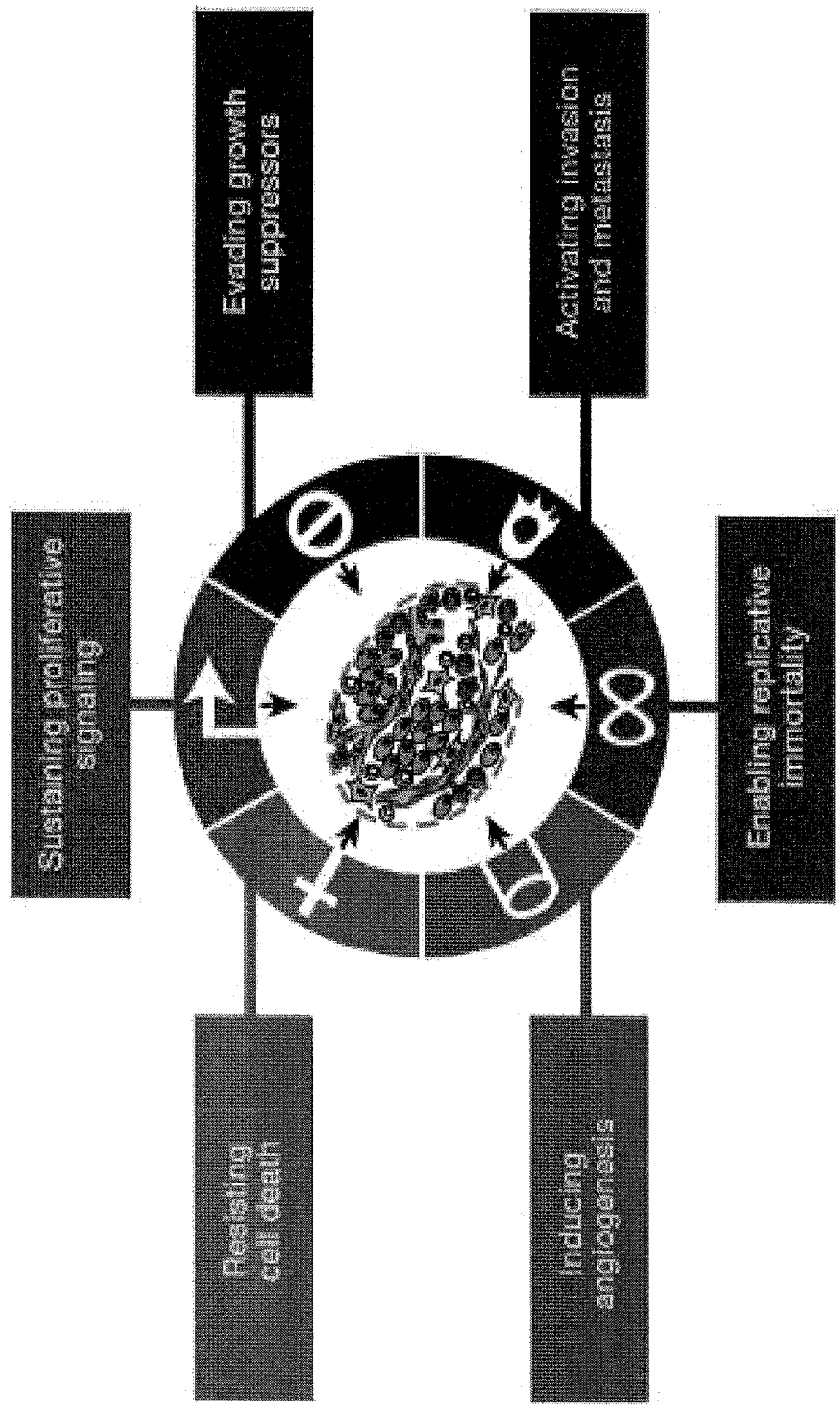
FIG. 1: Shows an exemplary schematic illustration describing embodiments of hallmarks of cancer and tumor development.

Aspects described herein stem from, at least in part, design of devices that allow for a controlled and physiologically realistic co-culture of tumor cells with normal cells, whether together in one chamber of the microfluidic device or separated by a membrane (or a combination of both). In one embodiment, the chambers of the microfluidic device are aligned (e.g., vertically) with each other with one or more membranes separating tumor cells from other non-cancerous cells ("cancer chip"). The cancer chip devices have been developed and optimized based on the basic design of an organ-on-a-chip as described in the U.S. Pat. No. 8,647,861, and the International Patent App. No. PCT/US2014/071611, the contents of each of which are incorporated herein by reference in their entireties.

Tumor cells are contemplated to be placed in microfluidic devices or chips. As used herein, malignant neoplasia are referred to as "cancer" and characterized by tumor cells which typically will ultimately metastasize into distinct organs or tissues. Malignant neoplasia include solid and hematological tumors. "Solid tumors" are exemplified by tumors of the breast, bladder, bone, brain, central and peripheral nervous system, cervix, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, sarcoma, skin (e.g. melanoma), small intestine, stomach (or gastric cancer), soft tissue, testis, ureter, vagina and vulva. Malignant neoplasias include inherited cancers exemplified by Retinoblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies (e.g. Kaposi's sarcoma).

Agents are contemplated for testing on the cancer chip. A variety of classes of agents are contemplated, including but are not limited to (i) kinase inhibitors such as e.g. Glivec, ZD-1839/Iressa, Bay43-9006, SU11248 or OSI-774/Tarceva; (ii) proteasome inhibitors such as PS-341; (iii) histone deacetylase inhibitors like SAHA, PXD101, MS275, MGCD0103, Depsipeptide/FK228, NVP-LBH589, Valproic acid (VPA) and butyrates; (iv) heat shock protein inhibitors like 17-allylaminogeldanamycin (17-MG); (v) vascular targeting agents (VAT) and anti-angiogenic drugs like the VEGF antibody Avastin or the KDR tyrosine kinase inhibitor PTK787/ZK222584; (vi) monoclonal antibodies such as Herceptin or MabThera/Rituxan or C225/Erbitux as well as mutants and conjugates of monoclonal antibodies and antibody fragments; (vii) oligonucleotide based therapeutics like G-3139/Genasense; (viii) protease inhibitors (ix) hormonal therapeutics such as anti-estrogens (e.g. Tamoxifen), anti-androgens (e.g. Flutamide or Casodex), LHRH analogs (e.g. Leuprolide, Goserelin or Triptorelin) and aromatase inhibitors. In one embodiment, the PHSCN peptide is contemplated, in the form of Ac-PHSCN-NH$_2$ where all the amino acids are L-isomers or where one or more amino acids are D-isomers as described in U.S. Pat. No. 8,940,701, hereby incorporated by reference.

In some embodiments, tumor cells are in contact with stromal cells (for example, lamina propria-derived cells). As used herein, the term "stromal" refer to connective tissue cells including but not limited to multipotent stromal cells (MSCs), e.g. Bone marrow derived mesenchymal stem cells, fibroblasts, myofibroblasts, mural cells (pericytes) of the vasculature, etc. Such cells may be found in or near sites of inflammation, such as in or near the lamina propria in vivo, e.g. mucosa, submucosa, etc. Stromal cells are anything that isn't parenchymal cells; lamina propria is a specific type of stroma. In some embodiments, stromal cells are contemplated for use in microfluidic devices of the present inventions. In some embodiments, "stromal cells" are contemplated for use after isolation from lamina propria-derived cells. In some embodiments, stromal cells are contemplated for use derived from regions that do not include lamina propria. In some embodiments, stromal cells are contemplated for use that are a mixture of LP-derived and non-LP-derived cells, e.g. when biopsy tissue used for isolating cells includes both mucosa and submucosal cells. In some embodiments, stromal cells are isolated from healthy and diseased individuals, and/or from different sites within the same individual. For example, stromal cells may be from the site of a tumor vs. from a healthy looking site.

In some embodiments, tumor cells are in contact with lamina propria-derived cells (or in close proximity). As used herein, the terms "lamina propria-derived cells" and "LP-derived cells" refers to cells used in the context of specific tissues (e.g. mucosal tissues), including but not limited to stromal cells, fibroblasts, and resident immune cells. In one embodiment, LP-derived cells are isolated from specific tissues (e.g. mucosal tissues). LP-derived cells are not limited to mucosal tissues, as they may be isolated from tissues extending into mucosal areas, for example, cells in stromal areas. LP-derived cells may be used directly after isolation or undergo culture to expand cell numbers prior to use. LP-derived cells may undergo isolation techniques before or after culturing or freezing. In other embodiments, LP-derived cells may be cryopreserved (frozen) prior to use.

As used herein, the phrases "linked," "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit).

"Channels" are pathways (whether straight, curved, single, multiple, in a network, etc.) through a medium (e.g., silicon, plastic, etc.) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents.

"Microchannels" are channels with dimensions less than 1 millimeter and greater than 1 micron. Additionally, the term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

DESCRIPTION OF THE INVENTION

The invention generally relates to a microfluidic platforms or "chips" for testing and understanding cancer, and, more specifically, for understanding the factors that contribute to cancer invading tissues and causing metastases. Tumor cells are grown on microfluidic devices with other non-cancerous tissues under conditions that simulate tumor invasion. The interaction with immune cells can be tested to inhibit this activity by linking a cancer chip to a lymph chip.

Hallmarks of cancer and tumor development: Cancer cells are abnormal compared to healthy normal cells in the body. Cancer cells have numerous characteristics, e.g. uncontrolled cell cycles, which allow them to live, replicate (grow), form tumors and/or spread throughout the body. Such growth typically results in severe illness and death unless the cancer is self-limiting (e.g. stops growing) and/or the immune system is able to control or irradicate these abnormal cells. See, schematic illustration of cancer cell characteristics in FIG. 1, Douglas Hanahan, Robert A. Weinberg, *Cancer Cell* 2011.

Several examples of conditions that affect cancer cell/tumor growth and cancer microenvironments include but are not limited to adjacent cells, e.g. a stromal component, an endothelial component, etc., and other forces, such as physical and mechanical, e.g. oxygen availability, etc.

I. Cancer-On-Chip

Figure 2:
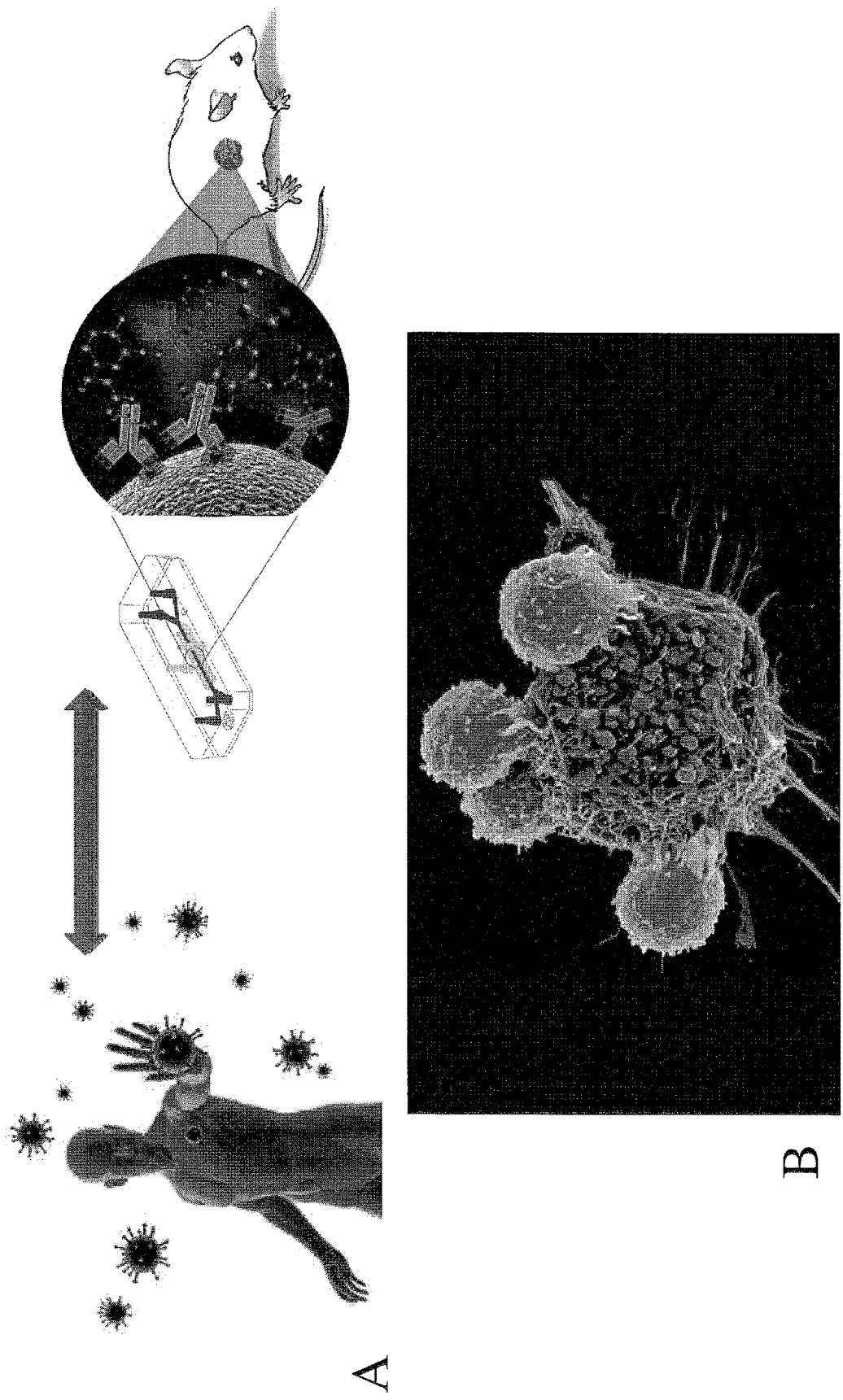
FIG. 2: Shows an exemplary schematic illustration of translational aspects and a micrograph of a cancer cell with attached immune cells.

As described herein, a Cancer-on-chip (Cancer-chip also Tumor-On-Chip or Tumor-chip) provides a mechanistic insight and a bridge for translation of in vitro experiments to humans. In one embodiment, it provides a means for translation of human in vitro experiments to humans. In another embodiment, it provides a means for translation of mouse experiments to humans. See, schematic illustration of embodiments in FIG. 2.

In one embodiment, a Cancer-on-Chip is a human Cancer-on-Chip. However, it is not meant to limit the Cancer-on-Chip to human cells. In one embodiment, a Cancer-on-Chip is a mouse Cancer-on-Chip. In one embodiment, a Cancer-on-Chip is a rat Cancer-on-Chip. In one embodiment, a Cancer-on-Chip is a dog Cancer-on-Chip. Thus, a Cancer-on-Chip may comprise any mammalian species. Further, in some embodiments, a mouse Cancer-on-Chip is contemplated to be developed using cells from transgenic/humanized mouse models. In some embodiments, a comparison of an animal Cancer-on-Chip model to human Cancer-on-Chip models are made for determining applicability of certain animal to human translations.

A. Tumor Microenvironment: Cells, Tumors, Extracellular Matrix (ECM), Stroma and Immune Cells.

Figure 3:
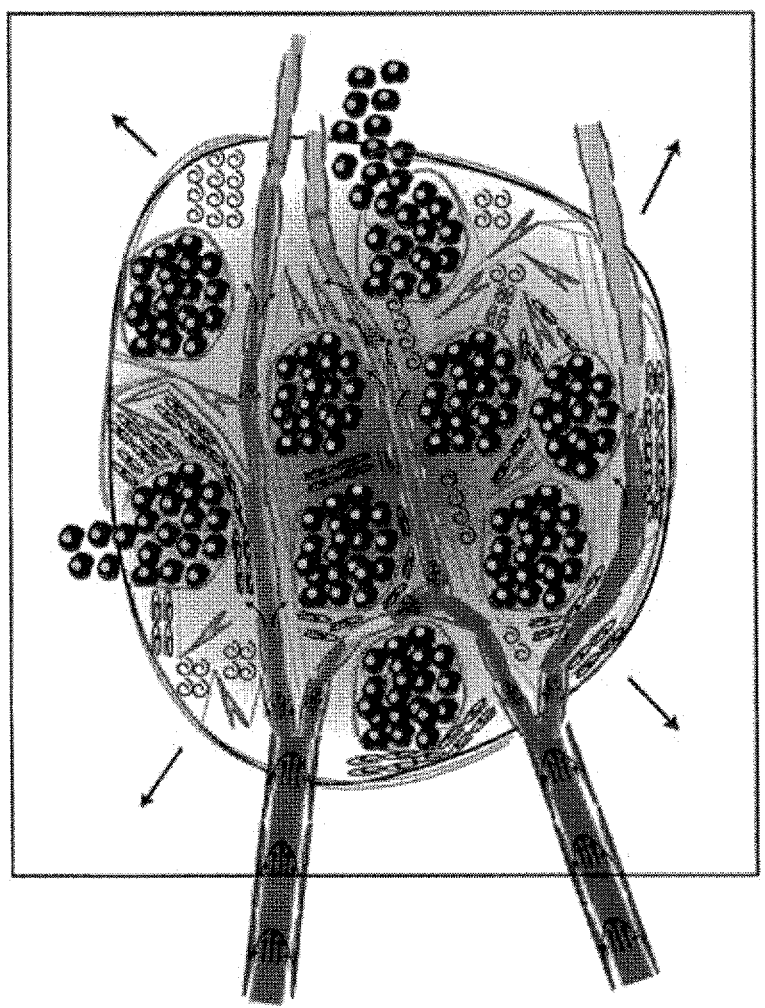
FIG. 3: Shows an exemplary schematic illustration describing embodiments of tumor growth. Tumors generate physical forces during growth and progression: including but not limited to blood and lymphatic flow; mechanical stress (IHP, hypoxia); and decreased perfusion and hypoxia suppress the immune response (pro-tumorigenic TAMs).

When a cancer cell forms a tumor, the tumor often provides a microenvironment both surrounding, on or near the inside surface and further inside the tumor. These microenvironments may be very different which is in part why these tumors are often difficult to study in vitro. Microenvironments are influenced by several components, including the cancer cells (which may have different types, e.g. nonmetastatic, premetastatic, metastatic, etc, and/or different levels of maturation, and other cell types that may be part of or surround the tumor, such as stromal cells, endothelial cells, etc., Further, the cells present make extracellular matrix, including but not limited to collagen, various types of hyaluronan, etc. Hyaluronic acid (HA; conjugate base hyaluronate), also called hyaluronan, refers to an anionic, nonsulfated glycosaminoglycan. See, for one embodiment of exemplary components, FIG. 3, Jain R K *Cancer Cell* 2014.

An artificial Biochemical Microenvironment of Cancer-On-chip provides greater control of soluble factors required for cell function and survival through a recreation of the biochemical microenvironment within the Chips; Enables recreation of spatiotemporal gradients of soluble factors that allow cells to thrive in vivo; etc. The Fluidic nature of the Chips allows the epithelial and endothelial channels to remain fluidic independent (laminar flow), allowing different mechanical forces precisely controlled for each tissue, as well as, independent biochemical signaling, and different use of cell culture medium or blood components in each channel. Continuous flowing cell culture media, blood substitute or blood components bring in fresh nutrients, soluble factors, and dissolved gases, while washing away waste products; Can connect different Organ-Chips allowing biochemical communication and signaling between different Organ-Chips in a physiological manner; where Conventional cell culture and other 3D in vitro systems such as organoids are static systems that fail to recapitulate in vivo dynamics and appropriate biochemical microenvironments. Thus, Cancer-In-Chips allow assessing developing tumors within the chip by several endpoints over the culture period: e.gs. growth and apoptosis rate of the cells will be monitored over time; Effluent will be collected to assess concentration of both dead and live cells; chips are amenable to real time microscopy, as well as IHC and H&E staining; secreted biomarker relevant to the cell model will be assessed by the best available method for each factor tested. Biomarkers that can be monitored in the clinical setting will be prioritized; In addition, cells will be collected and processed for RNA seq and epigenetic profiling (also to confirm the resemblance to the tumor of origin); Transcriptomic and metabolomics analyses will be performed to further characterize the tumor grown on chip. This characterization will be conducted in basal state and will be repeated as additional cellular components are added in the chip and comparisons between the different stages of development. An additional advantage of using Cancer-on-chip is that space constraints in the Chip provide an additional potential advantage of the Chips, in that the space limitations create a microenvironment similar to the confined, capsule-like structure, usually tumors grow in.

Figure 4:
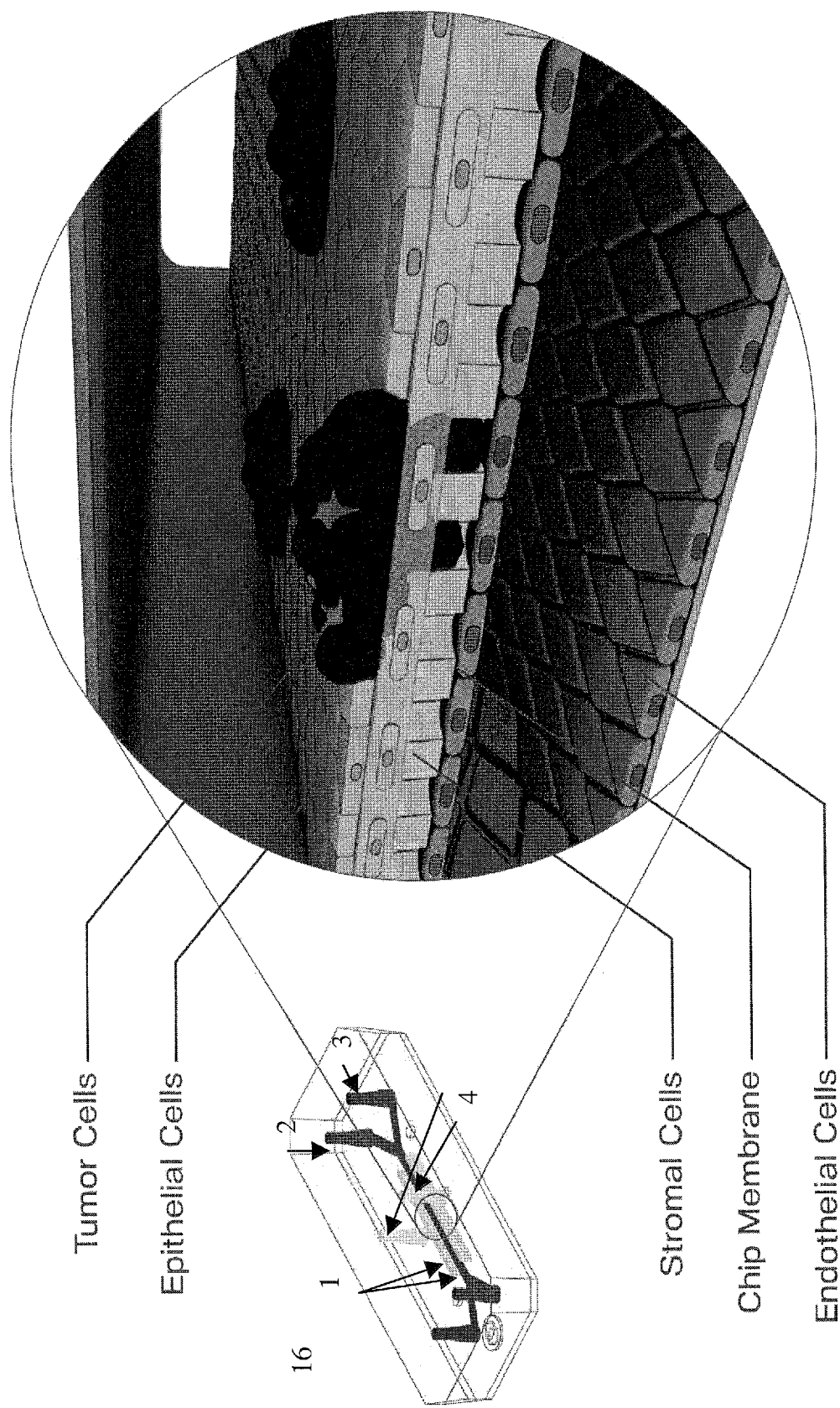
FIG. 4: Shows an exemplary schematic illustration of one embodiment for providing a Tumor-On-Chip (Tumor-Chip) and one embodiment for incorporation of a tumor microenvironment. On the left, a schematic illustration shows one embodiment of a microfluidic Tumor-On-Chip (16), having two microfluidic channels (1), with an upper channel port (2) and lower channel port (3), with optionally used vacuum chambers (4). On the right, a schematic illustration shows one embodiment of a microfluidic Tumor-On-Chip with four cell types, in the upper channel, tumor cells and epithelial cells on top of a stromal cell layer separated by a chip membrane from the lower channel with endothelial cells.
Figure 5:
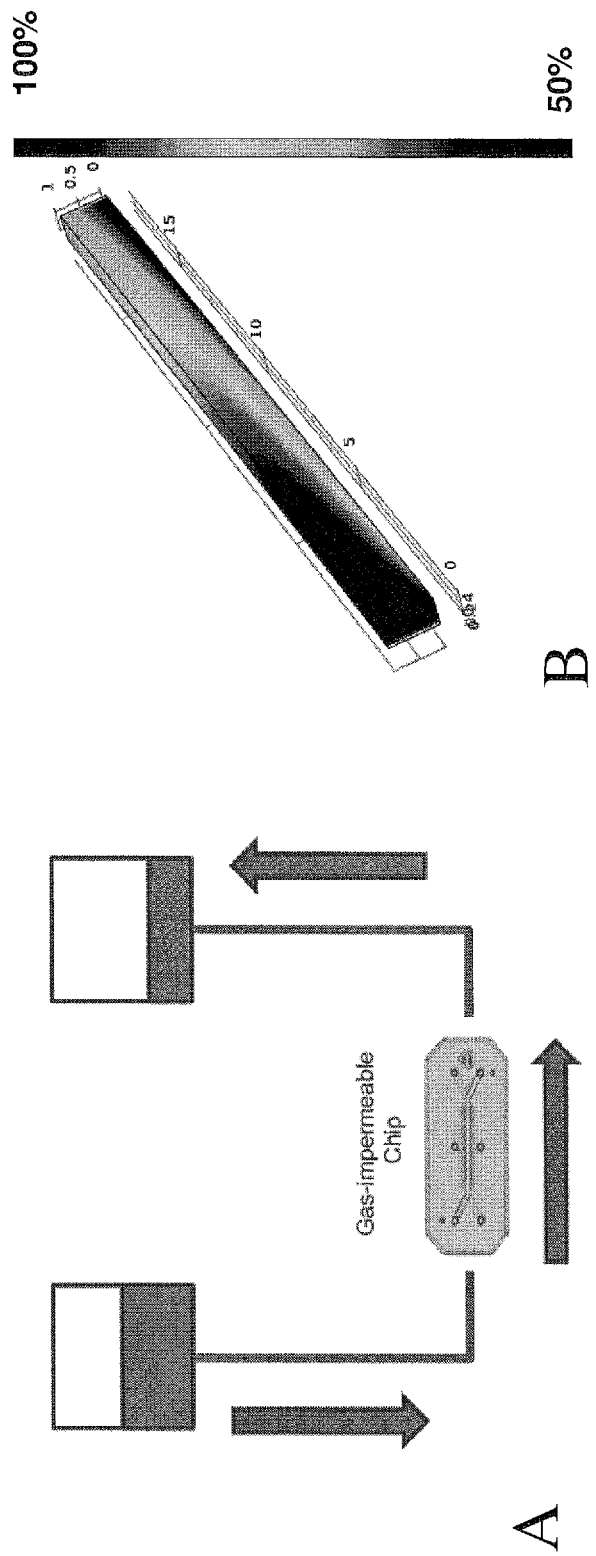
FIG. 5: Shows an exemplary schematic illustration of one embodiment for providing Hypoxia-on-Chip. In the upper left chamber of FIG. 5A: Control media gas concentration by bubbling a specific gas mixture through the chip into the receiving chamber in the upper right.
Figure 6:
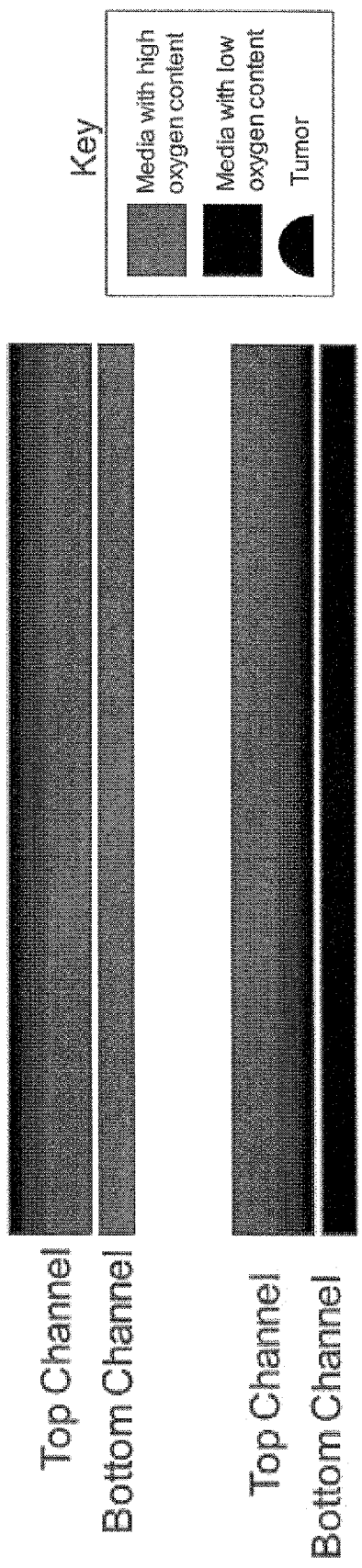
FIG. 6: Shows an exemplary schematic illustration of several embodiments for providing Hypoxia-on-Chip which provides numerous options for Oxygen Gradients-on-Chip.
Figure 6:
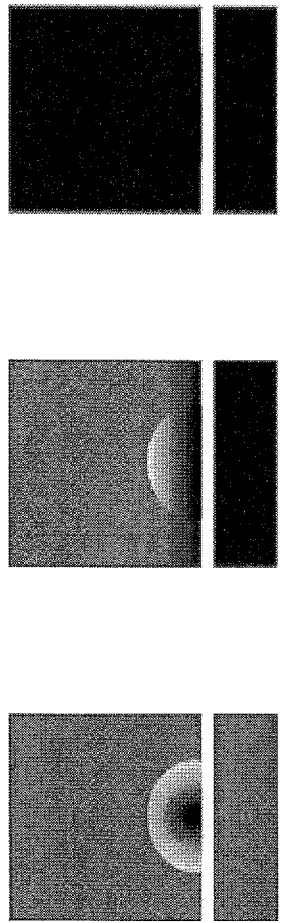
Figure 7:
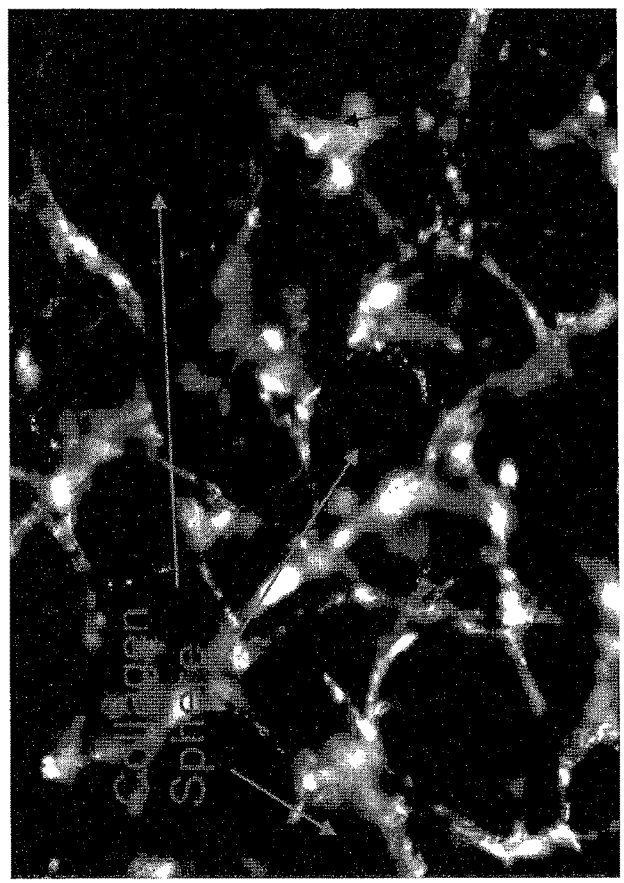
FIG. 7: Shows exemplary micrographs of a forming tubular network around Collagen I Spheres.
Figure 7:
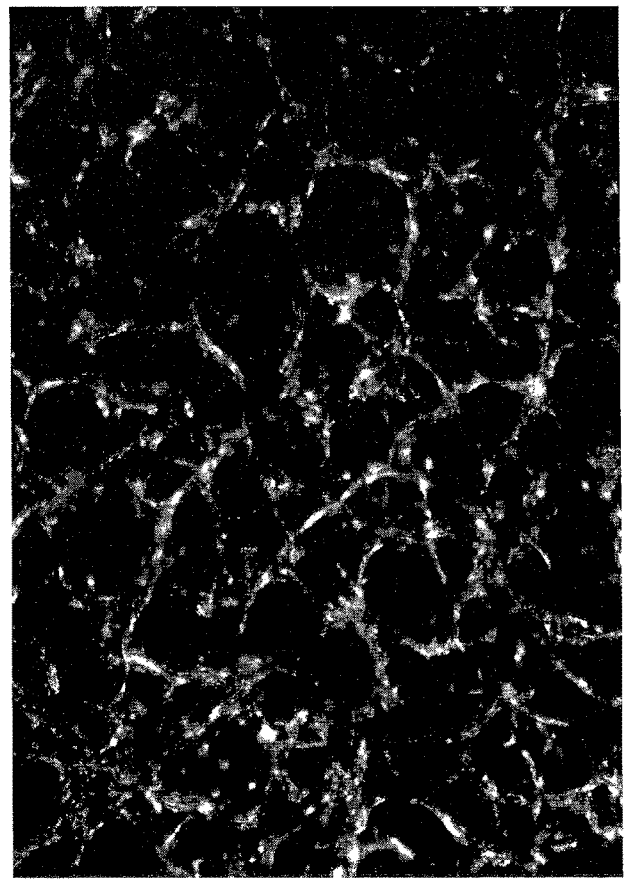
Figure 8:
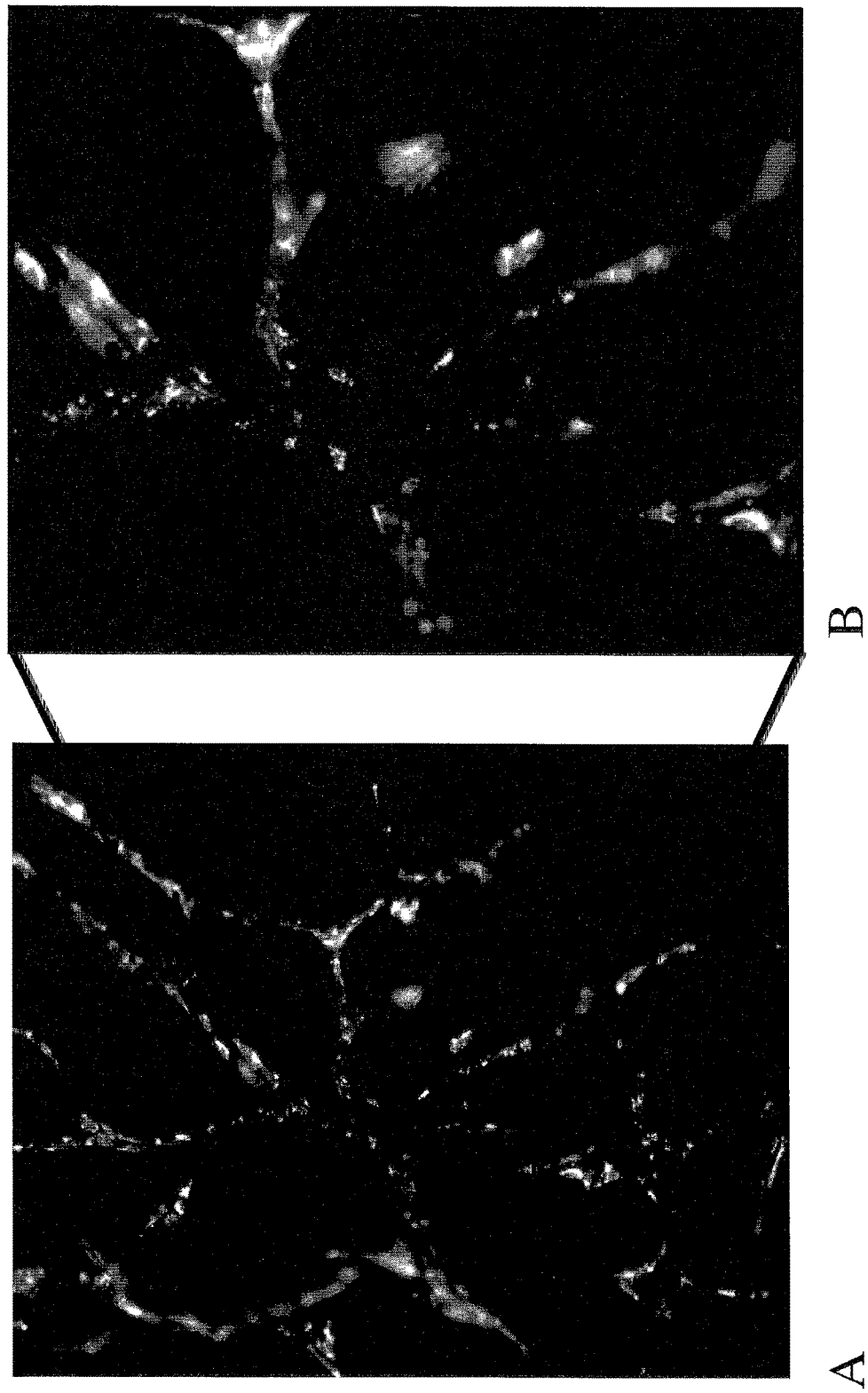
FIG. 8: Shows exemplary micrographs of a forming tubular network around Collagen I Spheres at high magnification.
Figure 9:
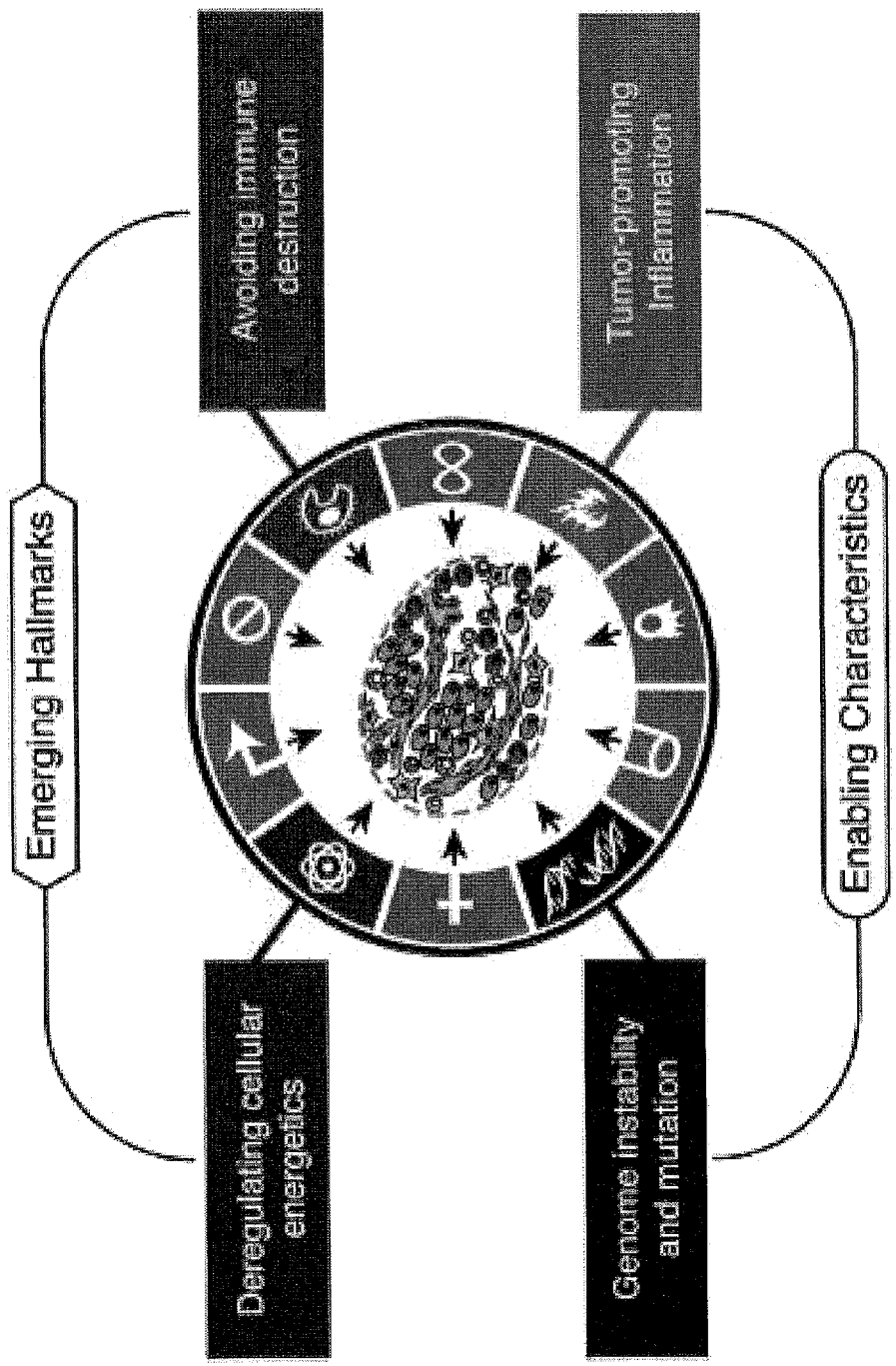
FIG. 9: Shows an exemplary schematic illustration of several embodiments of emerging Hallmarks and enabling characteristics of Cancer.
Figure 10:
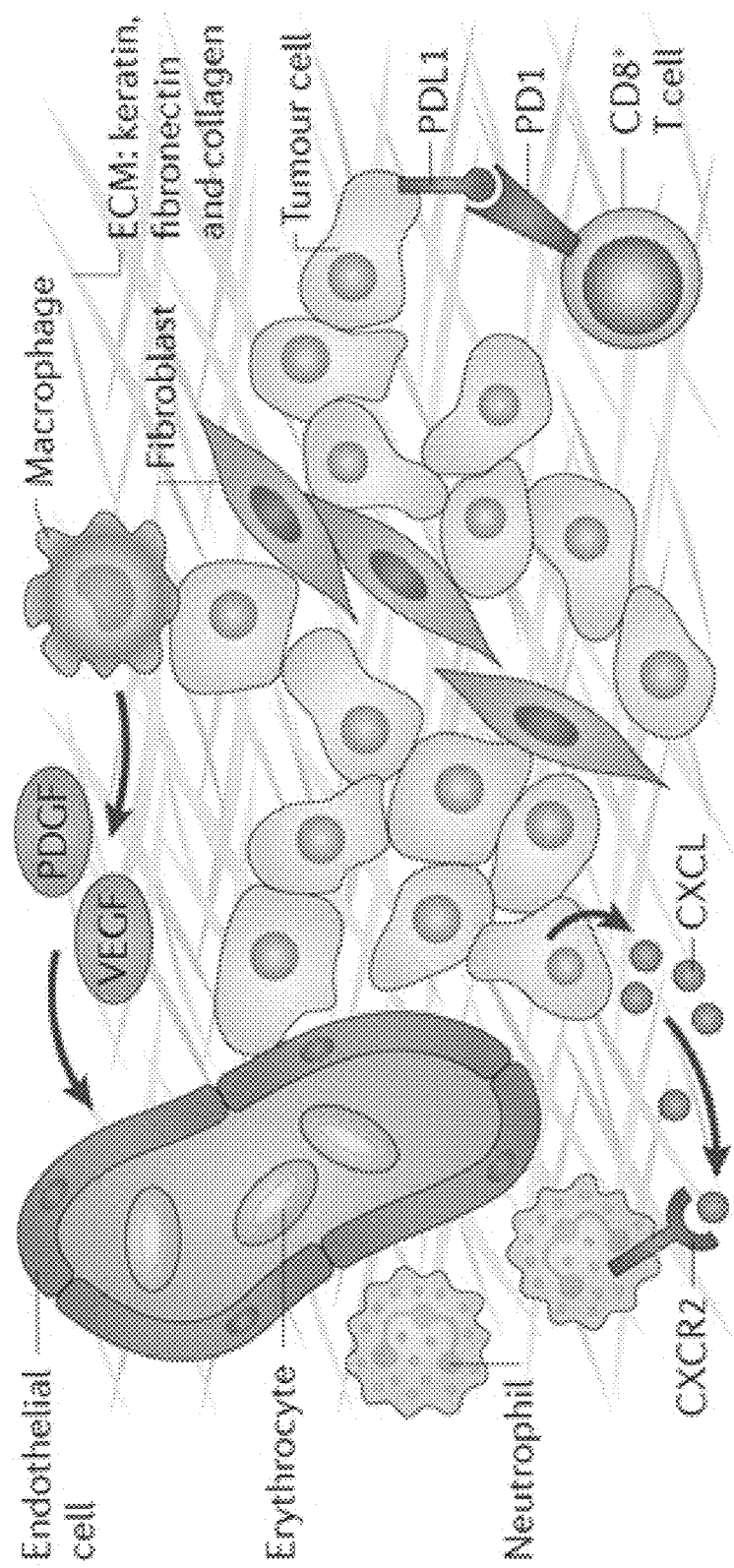
FIG. 10: Shows an exemplary schematic illustration of one embodiment of a cancer microenvironment, as one example, the lung cancer microenvironment including but not limited to cells, cell receptors, signaling molecules, etc. found in a cancer microenvironment.

In one embodiment, a Cancer-on-chip provides a co-culture for tumor growth in a tumor microenvironment comprising multiple cellular, and related, components, for example, Tumor (cancer) cells, an epithelial compartment, a stomal component, an endothelial compartment; see, for one embodiment, FIG. 4. Therefore, in one embodiment, a Cancer-on-chip provides a co-culture for testing tumor invasion of the surrounding tissues, i.e. the epithelial, stroma, endothelial, etc., additionally including exemplary environmental parameters that modulate cancer cells and tumors include ECM and oxygen concentration, described below.

Methods of application of Cancer-on-chips are contemplated for studying the tumor biology, microenvironment, immune system interactions, testing of efficacy and safety of potential therapeutics, elucidation of mechanisms of action, identification of biomarkers, system biology approaches, perturbations to microenvironment in cancer biology (e.g. presence of oncogenic factors in culture system). More specifically, pharmacology agents may be tested in these various contemplated environments for identifying agents for blocking uncontrolled growth, metastasis and invasion of other cell layers, tissues, etc.

1. Cancer Cell Sources

In some embodiments, examples of cells for use on chips are obtained from standard cell lines, primary tumor cells, primary tumor derived microbiopsies, etc. Cancer cells may be human cells, mouse cells, or cancer cells of other mammalian species. As one exemplary method for seeding and using cancer cells, melanoma cells (e.g. well characterized) may be used in order to determine optical fluidic culture conditions.

In one embodiment, human tumor cell lines for use in Cancer chips are derived from tumors with immunogenic ability, such as the melanoma (A375) and lung cancer (A549) lines.

In one embodiment, cell line seeded Cancer-On-chip will parallel Cancer-On-chip seeded with cultures of primary tumor cells. Primary tumor cells will be derived from freshly processed tumors/biopsy samples. Primary tumor cells may be derived, (e.g. isolated) from specific organs systems as well as patient specific cells, including but not limited to healthy cells, cancer cells and tumor cells. In some embodiments, cancer cells isolated from an organ or tissue are not the same type of cancer cells. For example, some lung cancer patients have small cell lung cancer while other patients have non-small cell lung cancer cells. Both types of cancer cells may find use in embodiments described herein for a lung Cancer-Cell-On-Chip. Moreover, tumor cells employed may not need to originate from the same organ type as other cells in the Organ-Chip. For example, pancreatic cancer cells may be used in a Liver-Chip to emulate a metastatic pancreatic cancer that has metastasized to the liver.

2. Endothelial Cells

In some embodiments, endothelial cells will be incorporated into Cancer-On-Chips for monitoring the interaction between tumor cells and endothelial cells, in particular for identifying factors leading to angiogenesis, and testing agents to inhibit such blood vessel formation, in addition to the formation of tumor vasculature, autophagy, etc.

In fact, incorporating endothelial cells in the lower (vascular) channel has a positive impact on long-term tissue viability in general. Further, endothelialized chips have a closer resemblance to phenotypic and functional indices of the organ of origin of cells for seeding Cancer-On-Chips.

Thus, in some embodiments, interactions with endothelial cells are provided. For one example, microvascular endothelial lung cells would be co-cultured with lung cancer cells and tumors. In some embodiments, interactions with endothelial cells extend the longevity of the healthy lung cells.

3. Healthy and Disease-Associated Materials

In some embodiments, the tumor microenvironment is explored by using materials (ECM, cells etc.) found in or around the tumor (i.e. disease-associated materials)—with or without the tumor cells themselves—in the microfluidic devices described herein. In other embodiments, materials (ECM, cells etc.) are used from healthy sources (healthy patients) or sites distant from the tumor site (cancer patients)—with or without the tumor cells themselves—in the microfluidic devices described herein. In some embodiments, disease-associated materials are compared with healthy materials in the microfluidic devices describe herein.

Some embodiments include using human cells and extracellar material, such as ECM, derived from each of these types of tissues. In particular, cells and/or at least one component isolated areas of tissue adjacent to tumor areas and at sites of cancer cell or tumor growth, including but not limited to types of cancer described herein.

As another example, lung is a frequent site of metastasis from extrapulmonary neoplasms. Bacterial infection-induced metastasis-conducive environments in the lung and cigarette smoke-induced inflammation are both associated with pulmonary metastasis from breast cancer. Further, such inflammation leads to the recruitment of bone marrow-derived neutrophils enhancing metastatic outgrowth, e.g. Rayes, et al., "Inflammation promotes metastasis through neutrophil protease-mediated degradation of Tsp-1." Proc Natl Acad Sci USA. 112(52): 16000-16005 (2015).

The following describes disease-associated materials contemplated for modeling and testing using a microfluidic device of the present inventions.

4. Extracellular Matrix (ECM) in Cancer-On-Chips

The ECM configuration, and specific composition, effects establishment of cancer cells and behavior of a developing tumor. Bhat and Bissell, "Of plasticity and specificity: dialectics of the micro- and macro-environment and the organ phenotype." Wiley Interdiscip Rev Membr Transp Signal. 3(2):147-163, 2014. Published online 2013. Thus, ECM for use in Cancer-on-chips may be isolated from or near tumors in vivo. On the other hand, healthy ECM is contemplated for use as well, i.e. not associated with cancer cell growth, etc., may be an isolated component of ECM, may be a commercial source, etc.

In some embodiments, the central flexible, porous, membrane that divides the central channel of the chip into two compartments (epithelial and endothelial—vascular channels) is covered (coated) with an ECM. In some embodiments, the membrane is coated with extracellular matrix proteins native to the specific organ or disease state. In some embodiments, the ECM promotes cell attachment and in vivo relevant organization of ECM and cell shape. In some embodiments, the cells under the in vivo relevant conditions recreated in the Chips also produce and modulate their own ECM, e.g. effecting progression of disease and microenvironment changes. In some embodiments, the ECM-cell interactions may effect cancer cell architecture, cell-cell communication, gene expression and differentiation. In part because ECM interactions and resulting cell-cell communication in other in vitro systems such as organoids lack in vivo relevance, in some embodiments, the ECM interactions and resulting cell-cell communication in Cancer-on-chips is contemplated to provide in vivo relevance.

In some embodiments, composition and stiffness of ECM is manipulated for identifying negative or positive effects on cancer cell/tumor growth. In some embodiments, determine ECM changes over co-culture time. In some embodiments, manipulate, e.g. overexpress/siRNA integrins or other factors.

As one specific example, the present invention in one embodiment contemplates utilizing the basement membrane (BM) in breast tissue—with or without the actual cancer tissue on the microfluidic devices described herein. The basement membrane in breast tissue is a specialized form of ECM linking epithelial and connective tissues, with adjacent stroma that traps an abundance of soluble factors constituting the microenvironment of the breast epithelium. More specifically, transmembrane integrins at the basal side of cells, having apical and basal polarity, serve as anchorage points and receptors for BM components. They trigger intracellular signaling and participate in the perception of the cells' microenvironment. They cooperate with growth factor receptors to control essential cellular processes such as survival, proliferation, and differentiation. Among the cell—BM contacts, basal polarity is specifically determined by the interaction between laminin-332 and α6/β4 integrin dimers that form hemidesmosomes. Lateral cell—cell contacts are mediated by apical tight junctions, adherens junctions, and in some instances desmosomes. The tight seal generated by tight junctions prevents milk leakage in-between cells during lactation. The apical junctional complex formed by tight and adherens junctions also organizes the cytoskeleton and associated signaling pathways, which ultimately impinges on nuclear functions. Thus, the basoapical polarity axis permits unidirectional secretion of milk components in the lumen, as well as structured integration of hormonal and mechanical signals exerted by the microenvironment. Vidi, et al., "Three-Dimensional Culture of Human Breast Epithelial Cells: The How and the Why." Methods Mol Biol. 945:193-219, 2013.

5. Lamina Propria and Resident Immune Cells

Resident immune cells (B cells, T cells, dendritic cells, macrophages, and innate lymphoid cells) may be isolated from cancer patients including from inflamed and non-inflamed regions of patient tissue. In one embodiment, LP derived resident immune cells may be isolated from sites of cancer/tumor cell growth. In one embodiment, LP derived resident immune cells may be isolated away from sites of cancer/tumor cell growth. As one example, lamina propria-derived resident immune cells are used in a Cancer-On-Chip as described herein. In one embodiment, tumor-associated immune cells are be isolated and included in the Cancer-on-Chip. In one embodiment, tissue-specific resident immune cells (e.g. Kupffer cells, Langerhans cells) are isolated and included in the Cancer-on-Chip.

In one embodiment, the present invention contemplates incorporating lamina propria-derived cells (such as resident immune cells, e.g. leukocytes, (i.e. white blood cells), mononuclear cells, resident fibroblasts, etc.) in the chip embodiments described herein. Thus, in one embodiment, LPDCs are incorporated into an embodiment of the Cancer-On-Chip. This can be done in a variety of combinations. In one embodiment, the LPDCs, stromal cells, and/or resident immune cells are deposited underneath epithelial cells and on top of an extracellular matrix (ECM) composition coated membrane (e.g. with a gel overlay or simply underneath the epithelial cells, i.e. without a gel overlay). In one embodiment, the LPDCs, stromal cells, and/or resident immune cells are further overlaid with a layer of ECM, i.e. ECM overlay, before depositing the epithelial layer. In one embodiment, however, the LPDCs, stromal cells, and/or resident immune cells are overlaid with an actual gel. In one embodiment, the LPDCs, stromal cells, and/or resident immune cells are deposited within a gel layer. The same or similar approaches can be used to incorporate other tissue-specific, stromal or resident cells (whether immune cells, fibroblasts, mixtures, etc.). In some embodiments, the LPDCs, stromal cells, and/or resident immune cells are deposited within the endothelial channel, whether above, below co-mixed, or instead of with endothelial cells.

The lamina propria-derived cells or stromal cells can be used for different degrees of purification or cell isolation: used wholesale, used with the cells isolated from ECM components, and isolated for specific cell types. Thus, in one embodiment, a full milieu of cell types was isolated and used in microfluidic devices described herein. An example of a full milieu of cell types used as a lamina propria-derived cell population, include but are not limited to stromal cells, fibroblasts, and resident immune cells. Examples of stromal cells include but are not limited to connective tissue cells, e.g. fibroblasts, myofibroblasts, etc., located in the mucosa, submucosa, etc. In fact, cells comprising LP-derived cells may not be limited to the mucosa. In some embodiments, Examples of resident immune cells including but are not limited to innate immune cells such as natural killer cells, γδ+ T cell receptor cells, adaptive immune cells, such as mononuclear cells, including monocytes, macrophages, basal cells, eosinophils, plasma cells, T cells, such as CD8+ CD4+, double positive, and dendritic cells, immature through mature, are found here. As another example, purified/isolated LP-derived cell populations were used in microfluidic devices described herein. In some embodiments LP-derived cells may be used directly after isolation. In some embodiments, LP-derived cells are expanded in cultures before adding to a microfluidic chip of the present inventions.

Thus, in other embodiments, other types of purifications or isolations are possible, including cells extracted from or isolated from lamina propria (as lamina propria derived cells, or LPDCs). In a preferred embodiment, resident immune cells are extracted and purified. In one embodiment, lymphoid follicles are not included. In one embodiment, lymphoid follicles are included. In one embodiment, Payers patches are not included. In one embodiment, Payers patches are included. Such that the presence of a lymphoid follicle or Payers patch in tissue used for isolation or extraction of cells may be determined by observation of the lamia propria tissue by optical microscopy prior to removal of cells. In one embodiment, capillary endothelial cells are extracted and purified.

In one embodiment stromal tissue is used for isolation of stromal cells, LP derived cells, etc.

Other embodiments contemplated for mimicking disease is by manipulating differentiation and/or activation stages of T cells. Thus, in yet another embodiment, pre-differentiated T-cells are added to a chip of the present inventions. In one embodiment, the present invention contemplates the use of published protocols to differentiate naive T-cells from peripheral blood mononuclear cells (PBMCs) isolated from blood samples towards a Th9 T-helper cell fate comprising the use of TGFb and IL4.

5. Multicellular Cytoarchitecture: Interactions with Stroma Cells/Stroma and Endothelial Cells/Vascularization.

In one embodiment, a Cancer-on-chip includes incorporation of stromal component. Thus, in one embodiment, a Cancer-on-chip provides a co-culture for determining responses of stromal cells to tumor cells. In one embodiment, a Cancer-on-chip provides a co-culture for determining effects of activated (tumor-derived) fibroblasts on tumor cell biology. In further embodiments, a Cancer-on-chip provides a co-culture for evaluating the activation of the stroma, interaction with tumor cells, and changes in the phenotype of tumor cells, following interaction with stroma, and effects on the vascular system such as changes in permeability, neovascularization and metabolic function.

A stromal component may be incorporated into the Tumor-Chip by adding normal fibroblasts, tumor fibroblasts, etc. In some embodiments, both fibroblast types will be tested with the same tumor cells for comparing results.

In particular, growth of tumor cells will be tested on top of stromal cells incorporated in a 3D-collagen gel or in separate channels where the stromal cells will be "housed" with the endothelial cells (as below), or with the stromal cells placed between the endothelial and the upper channel (tumor cells site). Characterization of growth parameters will be characterized, including by Imaging studies with specific antibodies for confirming the identity, morphological characteristics and properties obtained due to the co-culture in the Chip, e.g. identifying different cell types incorporated in the tumor-stroma Chips. Biochemical assays will assess secreting factors profiles and, transcriptomic analyses. The latter will be done to compare tumor cells transcriptomics with or without stromal cells in the Chip.

In one embodiment, a Cancer-on-chip includes a vasculature component. A vascular component of our Chip design offers distinct advantages, including the ability to better recreate a tumor microenvironment and/or tissue-tissue interactions (e.g. epithelial and vascular, tumor and vascular). In addition, having the vascular component allows us to bring in circulating immune cells and the system further supports immune cell recruitment (see Science 2010 Lung-on-Chip publication). Endothelial tissue added in the lower channel of the Chip can support flow from an independent (and thus of different composition, if needed) medium source. In one embedment, the two fluidic channels in the Chip have independent flow and are controlled independently. In one embedment, endothelial cells may be used to determine neutrophil recruitment to areas of cancer cell/tumor growth. The inclusion of a vascular component also seems to improve the longevity and functional phenotype of non-tumor elements of Organ-Chips.

Cancer-on-Chips may have both a tissue and a vascular component in the two separate channels, i.e. stromal cells in the upper channel and endothelial cells in the lower channel. The vascular component of our Chip design offers distinct advantages, including the ability to better recreate a tumor microenvironment, tissue-tissue interactions (e.g. epithelial and vascular, tumor and vascular). In addition, having the vascular component allows bringing in circulating immune cells and the system further supports immune cell recruitment (see Science 2010 Lung-on-Chip publication).

Conventional cell culture and other 3D in vitro systems such as organoids lack appropriate tissue-tissue interface and appropriate multicellular cytoarchitecture. Thus, Cancer-on-chips are designed for providng appropriate tissue-tissue interface and appropriate multicellular cytoarchitecture. Thus, in one embodiment, a Cancer-on-chip includes a Tissue-Tissue Interface and Multicellular Cytoarchitecture.

In some embodiments, through microengineering techniques we can direct the proper orientation of cells and their interactions with neighboring cells to recreate the in vivo situation. In some embodiments, Cancer-on-chips are designed to allow cells to reestablish essential tissue-tissue interfaces found in organs. In some embodiments, recreate multicellular architecture by adding more cell types to increase complexity of the tissue within the Chips, e.g. one embodiment of a Cancer-on-chip contains 4 different cell types (epithelial cells, liver sinusoidal endothelial cells, Kupffer cells (resident immune cells), and stellate cells (stromal cells).

In some embodiments, the present invention contemplates comparing regular fibroblast vs tumor fibroblasts, and adding myofibroblasts. In some embodiments, the present invention contemplates determining the effects of tumor on stromal differentiation (prognosis link). In some embodiments, modulate components to study effect on tumor growth.

In some embodiments, the present invention contemplates adding pericytes to Cancer Chip. In some embodiments, incorporate vascularization of the 3D tumor. In some embodiments, the present invention contemplates providing changes in the microenvironment by inducing barrier perturbation (vascular leakage). In some embodiments, the present invention contemplates determining the effects of barrier perturbation on growth and metastasis of cancer cells. In some embodiments, the present invention contemplates determining the ability of tumor cells to migrate into vasculature. In some embodiments, the present invention contemplates determining the effects of +/− endothelial cells, allowing a mechanistic understanding of the vascular component.

B. Tumor Microenvironment-Tumor Growth: Physical Forces.

Tumors may generate physical forces during growth and progression, for nonlimiting examples, blood and lymphatic flow, mechanical stress (e.g. intermittent hydrostatic pressure (IHP), hypoxia, etc.). The term "hypoxia" as used herein refers to a deficiency in oxygen. Thus, in some embodiments, elements of a Hypoxia-on-Chip are used in combination with a Tumor chip.

In some embodiments, label cells to follow growth and migration through imaging. In some embodiments, change oxygen levels, e.g. induce hypoxia conditions. In some embodiments, change mechanical pressures. See sections below describing these conditions in more detail.

1. Oxygen Concentration and Hypoxic Environment: Hypoxia-On-Chip

Tumors thrive in the hypoxic environment created as they expand in size. One main area of focus will be to recreate relevant hypoxic conditions within Cancer Chips and engineer a control that allows dynamic modulation of the oxygen concentration of the tumor microenvironment, in part, to study the impact of oxygen concentration on tumor growth within the Chip. Tumor development will be tested in normoxic and hypoxic conditions that will allow modulation of oxygen concentrations under controlled and regulated conditions.

In some embodiments, change the overall gas concentration in the system by controlling the gas concentration in media. In some embodiments, generate oxygen gradients on chip from cellular consumption of oxygen. In some embodiments, change the magnitude of the oxygen gradient by varying input oxygen concentration. In some embodiments, change the slope of the oxygen gradient by varying the input flow rate. In some embodiments, set oxygen concentration (mol/m^3) due to hepatocyte oxygen consumption in Tall Channel at a flow of 250 uL/hr.

Thus, in some embodiments, changing oxygen levels induces hypoxia for effecting tumor growth, invasion and migration. In some embodiments, reduced oxygen or hypoxia at or near the tumor may be generated by perfusion with fluid with reduced oxygen (or dissolved oxygen) concentration. In some embodiments, such reduced oxygen or hypoxia may be attained by disposing the Cancer-on-Chip or a portion thereof into a reduced oxygen environment (e.g. an hypoxic chamber).

2. Mechanical Forces

Mechanotransduction of mechanical forces in cells are determinants of cellular function, cell signaling, and gene expression and implicated in developmental biology. For examples, Cells in vivo experience mechanical forces via various mechanisms e.g. Expansion of lungs during breathing; Flow of air over cilia of epithelial cells in the airway; Flow of blood creating shear stress forces on vascular endothelium that can also impact epithelial cell function; Peristalsis in the intestine, etc. Further, mechanotransduction effects cell function and disease development including inflammation and immune response. Mechanical forces and mechanotransduction are not considered in other in vitro models including organoid models.

Thus, embodiments of Cancer chips may include mechanical forces, such as flow rates that generate physiological shear stress forces, or stretching of the chip.

a. Hydrostatic Pressure: Interstitial Fluid Pressure (IFP)

Solid tumors may have a raised interstitial fluid pressure (IFP) due, in part, to high vessel permeability, low lymphatic drainage, poor perfusion, and high cell density around the blood vessels.

Decreased perfusion and hypoxia suppress the immune response, and encourage pro-tumorigenic tumor-associated macrophages (TAMs)).

Some embodiments are contemplated for using human and mouse systems, for use separately and together for humanized systems.

In some embodiments, the effect of IFP is emulated by applying a fluid pressure the Cancer-on-Chip. For example, pressure may be applied through one of more fluidic channels that the Cancer-on-Chip comprises. Such pressure can be generated by means including by not limited to hydrostatic head, piston pressure, pneumatic actuation (e.g. of liquids), and a combination thereof. In other embodiments, IFP is emulated by the direct application of mechanical force to the site of interest (e.g. the tumor and/or its environment). For example, this can be accomplished through the direct action of a piston. In some embodiments, the IFP is modulated through the duration of the experiment. For example, it may be increased over time to mimic a growing tumor, or it may be varied cyclically.

b. Additional Mechanical Forces

In some embodiments, mechanical forces may include: shear stress, compressive forces, tensional forces, cell traction forces, cell pre-stress, etc.

II. Cancer-On-Chip with Immune Cells.

Immune cells are key mediators of inflammation and play important roles in diseases states such as cancer. Fluidic nature of the system allows immune cells to be introduced into the system in a dynamic manner, e.g. flow neutrophils or macrophages into the Chip, flow in immune cells from other organ systems, and introduce resident immune cells into the tissue within the Chip. Ability to study complex interactions between blood components. Conventional cell culture and other 3D in vitro systems such as organoids lack fluidic/dynamic nature and ability to flow in immune cells from other organ systems or to study hemodynarnics in vitro.

Thus, in some embodiments, immune cells are incorporated into the Tumor-Chip by flowing immune cells such through the Chip to successfully recapitulate this aspect of the tumor-immune cell interactions. The interaction of immune cells with tumor cells and endothelial cells will be assessed in real-time, e.g. real-time evaluation of chemotactic activity, including diapedesis to the epithelial layer. The goal on this step is to confirm that we can observe in the Chip the demonstrated, positive and negative interactions, of tumor cells with specific immune types, such as the CD8+ T cells, NK cells, Treg and myeloid suppressor cells. The major challenge here will be procurement of the cells and quality of the immune cells as well as obtaining matched cells from same donors for the different tissue within the chip. Exemplary steps for developing a Tumor-Chip include, but are not limited to, design, engineer, optimize, and characterize; mouse tissue used in chips (e.g. proof of concept: poc) and human chips, including but not limited to adding or developing myeloid suppressors.

A. Cancer-On-Chip with Blood Immune Cells and Blood Components

Given the role of recruitment of circulating immune cell and inflammatory responses in disease etiology, it is desired that these components be integrated into engineered in vitro disease models, an achievement that is now possible using microengineered and fluidic-based Cancer-on-Chip systems.

The interaction between cancer cells/tumors and circulating peripheral white blood cells, and other blood components, influences cancer cell and tumor viability, along with metastasis.

Thus, in one embodiment, incorporate immune cells into the Tumor-Chip by flowing immune cells such as PBMCS through the Chip to successfully recapitulate this aspect of the tumor-immune cell interactions.

The interaction of immune cells with tumor cells and endothelial cells will be assessed in real-time. The goal on this step is to confirm that we can observe in the Chip the demonstrated, positive and negative interactions, of tumor cells with specific immune types, such as the CD8+ T cells, NK (Natural Killer) cells, Treg and myeloid suppressor cells. The major challenge here will be procurement of the cells and quality of the immune cells as well as obtaining matched cells from same donors for the different tissue within the chip.

In one embodiment, observation of in vivo relevant dynamic interactions between tumor cells and cells is contemplated to determine the specific impact of the endothelium on this interaction over time. Therefore, this artificial system will allow one to address questions such as the order of events in the interaction of tumor and endothelial cells as well as gain mechanistic understanding. The in vivo models are not always helpful in elucidating such mechanisms as they provide a whole animal view, rather than cellular resolution view. In one embodiment, a comparison of these microfluidic chip based in vitro studies to in vivo studies is contemplated.

1. Immune Cells

In further embodiments, an immune component is incorporated. Supply of specific human immune cells may be from peripheral blood cells of a patient, healthy, precancerous or diagnosed with cancer, with or without undergoing treatment. In one embodiment, in vitro studies incorporating immune cells are engineered to be translated into in vivo studies.

Immune interactions may be local (by adding cells to chips). Thus, in one embodiment, at least one type of immune cell is added to a Cancer-In-Chip. In one embodiment, incorporation of monocytes in the Cancer-on-Chip is contemplated, in addition to different cell types, e.g. epithelial, endothelial, stromal and resident immune cells, in addition to cancer cells or tumors.

2. Tumor-Infiltrating Lymphocytes (TILs)

In yet another embodiment, Tumor-infiltrating lymphocytes (TILs) are added to a Cancer-In-Chip. In some embodiments, TILs may be isolated from tumors for adding to chips. In some embodiments, TILs may be derived from infiltrating immune cells added to chips, as described herein.

In one embodiment, compartmentalize areas containing at least one type of immune cell is provided within the chip. Thus, in one embodiment, an isolated lymph node, e.g. isolated from a subject, e.g. healthy, patient, cadaver, etc., may be added to a Cancer-In-Chip. Thus, in one embodiment, T cells are introduced into Cancer chips. In one embodiment, antigen-presenting cells are introduced into Cancer chips.

Thus, in one embodiment, gradually build the chip's complexity in part by adding different types of immune cells.

Selection of T cells and myeloid suppressor cells for adding to these cultures, address potential adverse immunological reactions due to lack of histocompatibility. Thus in some embodiments, immune cells are autologous to cancer cells. In some embodiments, immune cells are engineered to reduce immune reactions due to MHC mismatch. In some embodiments, cancer cells are naturally or engineered to reduce MHC mismatch immune stimulation.

III. Additional Chips for Linking with Cancer-On-Chip

The ability to link multiple Organs-on-Chips (via exposure of effluent or direct linking of multiple tissues) would also enable the study of dynamic interactions between different organs systems that are known to be essential in tumor biology. Therefore, in combination with a Tumor-on-Chip, immune system chips may be fluidically linked for imitating an immune system, including the emulation of Lymph node or Thymus-on-Chip, and the Bone Marrow. An advantage is that the architecture of these organs is well characterized to guide the engineering to the incorporation of the essential components in an orderly manner, i.e. one at a time incorporation into the Cancer chip system. The caveat is that they are constitutively active organs, with a range of dynamic regulatory functions, and their functions are finely modulated by a number of stimuli.

Further, embodiments are contemplated to gradually build the system's complexity, in part, by linking different types of chips comprising specific cell types, such as epithelial cells, immune system cells, etc. for modeling specific cell-cell interactions and/or interactions of cancer cells/tumor with dynamic systems, such as Lymph node-chips, Bone marrow-chips, etc. Thus, in yet other embodiments, systems on separate chips are linked with Cancer-on-Chip, e.g. stromal-chip, endothelial-chip, epithelial-chip, immune-system chip, etc.

In one embodiment, an immune cell may be added to a Cancer-On-chip by a systemic simulation (i.e. linking chips, e.g. Lymph node chip) together with a Cancer-In-Chip. Thus, in one embodiment, a Cancer-on-chip provides a co-culture system for tumor interactions with the lymphatic system.

Further, embodiments are contemplated to gradually build the system's complexity, in part, by linking different types of chips comprising immune system cells. In yet further embodiments, immune system chips, e.g. Lymph Node-Chip, Bone-Marrow-Chip, Thymus-Chip, DC-Chip, etc. are linked with Cancer-on-Chip. Therefore we propose to develop the Tumor-on-Chip with an immune system simulation, including the emulation of Lymph node Thymus-on-Chip, and Bone Marrow-on-Chip, described below.

The ability to link multiple Organs-on-Chips (via exposure of downstream effluent or by direct circular linking of multiple tissues) would also enable the study of dynamic interactions between different organs systems and Cancer-on-Chip that are known to be components in tumor biology.

The interaction between tumor and lymph nodes or bone marrow will be achieved by linking the Tumor-Chip with an Immune System-Chip, such as lymph node or bone marrow. Thus communication will be established via engineered gradients of media containing chemokines and/or other tumor chemotactic factors that will be recirculating to reveal successful functional interaction between the two, to be assessed by relevant markers and cell changes characterization. We anticipate that successful linkage should be able to resemble lymphatic drainage of the tumor to a tissue, and then expand the linkage to include additional, distant organs, normal stromal, normal endothelial cells, etc.

After linking, immune chips, additional studies are contemplated to explore functionality for a number of processes requiring immune system and tumor interactions such as: Tumor-associated inflammation; effect of stroma and/or tumor cells in mobilization of immune cells by the respective organs and the subsequent efficacy of immunotherapy (in an effort to simulate early and late effects in the course of tumor expansion) to control the metastatic capacity of the original tumor, etc.

A. Lymph Node-Chip

In some embodiments, a lymph node-chip is linked to a Tumor-Chip. Exemplary steps for developing a lymph node-chip include, but are not limited to, design, engineer, optimize, and characterize; mouse tissue used in chips (e.g. proof of concept: poc) and human chips. Thus, in one embodiment, a system is provided for tumor-immune system interactions by linking a Cancer-on-Chip to a Lymph Node-Chip. Such a chip is contemplated to have Lymph Node-relevant architecture, in- and out-flow, etc., for simulation of draining lymph node function.

A Lymph Node-Chip is designed to recapitulate the entry of antigen presenting cells (APCs) in the lymph node, the contact between APCs and T cells residing in the lymph node and the traveling of T cells to (and/or from) the tumor. APCs may need pre-activation (in addition to activation via tumor cells contact). In one embodiment, a gradient of CCL19, CCL21 is created inside the lymph node chip to recapitulate the in vivo microenvironment.

As one example of an embodiment to provide effects of CTLs on cancer cells, cytotoxic cells will be dyed with a cell dye to be distinct and followed by microscopy. In one embedment, a CTL will be exposed to the primed DC and then will be circulated in the system through a cancer chips's vascular system. CD8+ T cells may be prohibited from entering the tumor, e.g. stacked in the stroma, a response that could be modified by specific immunotherapies. Such that, such a chip might recapitulated tumor "non immune-permissive" environment, in part, to proceed with testing of therapeutic approaches. Our goal is that antigen-presenting cells (dendritic) perfused in the tumor, will be interacting with T cells in the lymph node-on-chip. Next, T cells "educated" by DCs through an engineered closed circuit will be driven to the tumor, via development of chemokine gradients or similar approaches, to assess their interaction (or not) with the tumor. As expected by the in vivo conditions, the CD8+ T cells should be prohibited from entering the tumor and should be stacked in the stroma, or if entered in the tumor will show no cytotoxic activity (exhausted T cells), a response that could be modified by specific checkpoint inhibitors. Recruitment of the educated T cells to the tumor site will be driven by engineered fluidic pressure differences, and if needed by developed chemokine gradients.

In one embodiment, migration/attraction of activated T cells from the lymph node chip back to the tumor chip is observed. In one embodiment, flow is used for migration. In one embodiment, antigen (Ag) presentation to T cells suffices to attract immune cells to the tumor site. In one embodiment, a tumor chip gradient of chemoattractants (e.g. chemokine) is established when Ag presentation to T cells does not suffice to attract immune cells to the tumor site.

B. Lymph Node-Chip and Circulation/Metastasis.

The interaction between tumor and lymph nodes or bone marrow will be achieved by linking the Tumor-Chip with an Immune System-Chip, such as lymph node or bone marrow. Thus communication will be established via engineered gradients of media containing chemokines and/or other tumor chemotactic factors that will be recirculating to reveal successful functional interaction between the two, to be assessed by relevant markers and cell changes characterization. We anticipate that successful linkage should be able to resemble lymphatic drainage of the tumor to a tissue, and it is possible we will then expand the linkage to include additional, distant organs or just normal stromal or endothelial cells.

As one example, lung cancer is modeled in relation to draining lymph nodes. Thus, in one embodiment, a normal Lung-Chip is linked to a Lymph Node-Chip interconnected with a Melanoma Chip to provide a system for melanoma metastasis to lung tissue.

C. Bone Marrow-Chip

A Bone Marrow-Chip is provided as a source for immune cells that will be attracted by—and recruited to—the Tumor-Chip through fluidic communications. Thus, immune cells are incorporated into the Tumor-Chip by flowing immune cells originated from the Bone Marrow-Chip to recapitulate this aspect of the tumor biology. In one embodiment, a Bone Marrow-Chip is a microengineered model that replicates native niche and key immunological function of human bone marrow in vivo. In one embodiment, a Bone Marrow-Chip is a mouse Bone Marrow-Chip. In one embodiment, a Bone Marrow-Chip is a human Bone Marrow-Chip.

In one embodiment, a Bone Marrow-Chip in fluidic communication with a Cancer chip recapitulates tumor-mediated signals to the bone marrow to trigger proliferation of relevant progenitors and induce mobilization of myeloid cells that populate the tumor itself. IN one embodiment, this platform enables maintenance of the physiological bone marrow microenvironment and production of genetically altered neutrophils in vitro from retroviral-transduced hematopoietic stem cells, an extremely difficult task. Furthermore, this in vitro system makes it possible to retain the microvasculature within the marrow and to simulate mobilization and recruitment of neutrophils using chemokines and colony-stimulating factors.

A prototype system will be constructed by incorporating human bone marrow obtained surgically from thoracectomy into a perfusable Chip that contains a vascularized three-dimensional tissue culture scaffold. The design of this model will enable spontaneous anastomosis of the microvasculature in the marrow with a network of microengineered blood vessels, making it possible to generate and precisely control vascular perfusion of the bone marrow. Once this culture is established, human hematopoietic stem cells will be introduced into the engineered tissue and induced to differentiate into the myeloid lineage. Functional validation of this model will be initially achieved by measuring mobilization of neutrophils in response to colony-stimulating factors such as G-CSF or CXC chemokines such as IL-8. The model will be applied to the Cancer-Chip using effluent form the tumor chip to mobilize myeloid suppressor cells and monocytes and measure their ability to get incorporated within the Tumor-on-Chip. Actual linking between the different chips will be done as outlined herein.

D. Linking Immune System-On-Chips: Draining Lymph Node-On-Chip and/or Bone Marrow-On-Chip (and or Other Immune-Chips) with Cancer-On-Chip.

In one embodiment, a Draining Lymph Node-Chip and/or Bone Marrow-Chip is fluidically linked with a Cancer-On-Chip, in part, for demonstrating recruitment of bone marrow cells by the Cancer-On-Chip. In one embodiment, a rodent Bone-marrow-on-Chip is used in combination with a human cancer chip. In one embodiment, a rodent Bone-marrow-on-Chip will facilitate translation to human Bone Marrow-on-Chip model.

In one embodiment, a Draining Lymph Node-Chip and/or Bone Marrow-Chip in combination with a Cancer-On-Chip recapitulate the in vivo process where immune cells are recruited from and/or educated in the above organs before reaching the tumor site. In one embodiment, linking Lymph node- to the Cancer-On-Chip is to recapitulate the full process including antigen presentation, T-cell education and recruitment. Similarly, linking of Bone marrow to the Cancer-On-Chip is done to recreate the environment promoting proliferation, differentiation and recruitment to the tumor of myeloid-derived cells.

In one embodiment, a Thymus-on-Chip is linked to a Cancer-On-Chip. In one embodiment, in vivo relevant DC-tumor cell interactions are contemplated, in part for proceeding with the incorporation of lymphocytes and experimentation with immunotherapies. In one embodiment, tumor dendritic cells (DC) are added in order to assess their priming by exposure to tumor antigens.

Interaction of the Immune System with the Cancer-On-Chip, e.g. for modeling immunocyte migration in the tumor; Perfuse dendritic cells (DC) into the tumor in order to prime them with tumor-specific antigens and expose a separately maintained culture of fluorescently labeled cytotoxic cells to the primed DC to assess their interaction. These cytotoxic cells will then be perfused into the chip through the "vascular" channel to assess the existence of an in vivo relevant "immune privileged" environment near the tumor. These developments will enable development of a model for the recruitment of immune cells by the tumor.

E. Interaction of Dendritic Cells with the Cancer-On-Chip

The goal is to obtain the in vivo relevant DC-tumor cell interaction, required for proceeding with the incorporation of lymphocytes and experimentation with immunotherapies. As our strategy includes gradual development of the tumor immune environment first we will flow through the tumor dendritic cells (DC) in order to assess their priming by exposure to tumor antigens. This is a critical step, as it will help to confirm recapitulation of functional interactions critical in vivo. The POC in mouse Tumor-Chip in this step may help in the engineering and fine tuning of the system, to proceed with the human cells and provides the in vivo correlation.

IV. Examples of Cancer-On-Chip Embodiments for, e.g., Identification of Targets for Testing Cancer Therapeutics, Cancer Prevention, or Metastasis Prevention A. Tumor-Introduction Cancer-On-Chip In some embodiments, a Cancer-On-Chip is a Tumor-Introduction Cancer-On-Chip. A Tumor-Introduction Cancer-On-Chip refers to chips initially having no tumor cells, and either cells or microenvironment elements from a) a non-cancer microenvironment (e.g. normal healthy cells, or cells away from the site of a tumor), b) the site of a tumor (or in close proximity), or c) an environment with a predisposition or risk factor for cancer (e.g. derived from a patient with known susceptibility alleles). Such cells or microenvironment elements may include epithelial cells, stromal cells, immune cells, connective tissues, ECM, soluble factors, lamina propria derived cells (LPDC), etc. In one aspect of the invention, a tumor-generating process is enacted on the Tumor-Introduction Cancer-on-Chip. For example, tumor cells may be introduced into the Cancer-on-Chip's parenchymal compartment (e.g. by flowing in tumor cells), tumor cells may be introduced into the Cancer-on-Chip's vascular compartment (this may serve as a model of metastasis), by the application of radiation, and/or by the introduction of a carcinogenic agent. The Tumor-Introduction Cancer-on-Chip can be used, for example, to help determine whether an agent (e.g. a pharmaceutical compound) may protect from tumor introduction or whether any of the Cancer-on-Chip's elements are protective or act as risk factors, and if so, by what mechanisms. In such embodiments, the Cancer-on-Chip may provide utility in identifying the significance of different elements of the cancer microenvironment or patient background. For example, in one embodiment, we disclose a method wherein two or more Cancer-on-Chips are compared, wherein two or more of the Cancer-on-Chips differ in the origin of one or more of its components (e.g. particular cells, ECM, soluble factors or other components originate from the site of a tumor vs. away from it, or from an at-risk patient vs. a normal-risk patient, etc.)

B. Sick and at-Risk Cancer-On-Chip

In contrast to the Tumor-Introduction Cancer-On-Chip, in some embodiments, a Cancer-On-Chip is a Sick Cancer-On-Chip. A Sick Cancer-On-Chip refers to a chip containing pre-cancerous cells or cancerous cells. In some embodiments of the Sick Cancer-on-Chip, which we Willi the At-Risk Sick Cancer-on-Chip may comprise cells and/or components isolated from a cancerous microenvironment, such as epithelial cells, endothelial cells, stromal cells, stroma, immune cells, tissues, ECM (e.g. complete or an isolated component), soluble factors, lamina propria derived cells (LPDC), etc., derived from subjects with risk factors for the type of cancer for use in the chip, cells derived from subjects known to have risk factors for any type of cancer, cells derived from subjects known to have or under treatment for cancer or under treatment for another disease where a side effect is the development of cancer cells or be in remission from cancer, e.g. cells or cells derived from subjects known susceptibility alleles for the type of cancer for use in the chip, etc. In other words, a At-Risk Sick Cancer-On-Chip refers to chips where at least one of the components are known to have genetic or physiological association with cancer arising from at least one sick component on a Sick Cancer-On-Chip. In some embodiments, such a Sick Cancer-On-Chip with at least one sick component is used to determine stages of cancer development in response to endogenous factors. In some embodiments, such a Sick Cancer-On-Chip with at least one sick component is used to determine stages of cancer development in response to simulated exogenous agents, including, for example, drugs, chemotherapy, suspected or known carcinogens, immunotherapy, or antibodies added to or flowed through the Sick Cancer-On-Chip.

C. Metastatic System Comprising Multiple Cancer-On-Chips

Certain types of cancers are associated with metastasis to other organs where secondary cancer/tumors grow. As on example, common sites of metastases for lung cancer are other parts of the lung, adrenal gland, bones, brain and liver. Thus, in one embodiment, a Cancer-on-Chip comprises tumor cells from one organ-type disposed within or introduced to an Organ-Chip of a different organ-type.

In another embodiment, a Cancer-On-Chip effluent (outflow) is fluidically linked (i.e. in fluidic communication) with another Cancer-On-Chip. As one example, a first Cancer-On-Chip is fluidically linked with a second Organ-Chip, with the second Organ-Chip representing the same organ-type as the first Cancer-on-Chip. Such embodiment can be used, for example, for identifying factors and/or testing factors or testing anti-metastatic agents on cancer cell metastasis from one tissue site (e.g. microenvironment) to another tissue site (e.g. microenvironment) within the same tissue or organ.

As another example, a first Cancer-On-Chip effluent (outflow) is fluidically linked (in fluidic communication) with a second Organ-Chip, with the second Organ-Chip representing a different organ-type than the first Cancer-on-Chip. Such embodiment can be used, for example, for identifying factors and/or testing factors or testing antimetastatic agents on metastasis from one type of tissue or organ to another tissue or organ. Thus, in some embodiments, the first Cancer-On-Chip is a Lung Cancer-On-Chip while the second chip may be any one or more of, merely for non-limiting examples, an Adrenal gland-On-Chip, Bone Marrow-On-Chip, Brain-On-Chip and liver-On-Chip.

As one example, colon cancer is associated with metastatic secondary liver cancer. Thus, in one embodiment, a colon Cancer-On-Chip effluent (outflow) is fluidically linked to a liver-On-Chip. As another example, colon cancer is associated with metastatic secondary lung cancer.

Thus, in one embodiment, a colon Cancer-On-Chip effluent (outflow) is fluidically linked to a Lung-On-Chip. As yet another example, pancreatic cancer is associated with metastatic secondary liver cancer. Thus, in one embodiment, a pancreatic Cancer-On-Chip effluent (outflow) is fluidically linked to a Liver-On-Chip.

In some embodiments, various organ chip devices described in the International Patent Application Nos. PCT/US2009/050830; PCT/US2012/026934; PCT/US2012/068725; PCT/US2012/068766; PCT/US2014/071611; and PCT/US2014/071570, the contents of each of which are incorporated herein by reference in their entireties, can be modified to form the devices described herein. For example, the organ chip devices described in those patent applications can be modified in accordance with the devices described herein.

In yet further embodiments, a Sick Cancer-On-Chip is fluidically linked to (in fluidic communication with) a Tumor-Introduction Cancer-On-Chip, wherein cancer cells for seeding a Tumor-Introduction Cancer-On-Chip derive from metastatic cells, e.g. cells actively detaching from a Sick Cancer-On-Chip flowing to a Tumor-Introduction Cancer-On-Chip or shed from a tumor growing in a Sick Cancer-On-Chip. As one example, fluid flowing through microfluidic connections to a Sick Cancer-On-Chip flows into to a Tumor-Introduction Cancer-On-Chip. In some embodiments, microfluidic connections may be coated with a material so that flowing cells do not stick to or become attached to internal surfaces of the fluidic connections. In some embodiments, microfluidic connections may be coated with a material so that metastatic cells may migrate by crawling along internal surfaces of the fluidic connections into the next chip.

In some embodiments, one or more of the fluidic connection between the aforementioned microfluidic devices (e.g. first Cancer-on-Chip and second Organ-Chip) may comprise tube, channels or bridges. In other embodiments, the said one or more fluidic connections may comprise discrete fluid transfers. Such discrete transfers may be enacted manually or by means or a liquid-handling robot or autosampler.

V. Testing Immunotherapeutics in the Tumor and Immune System-Chips

In one contemplated embodiment, demonstration that Chips can recapitulate response and effects on the tumor tissue and immune system to known therapeutics, such as check-point inhibitors currently in clinical use. Thus, the Cancer-on-Chips technology can serve as a platform for testing of novel therapeutics with the ability to predict efficacy, toxicities, and mechanism of action in an in vivo relevant, dynamic human cells environment. Further, use the Cancer-on-Chips systems to support a system biology approach to discover new potential targets and biomarkers for therapeutic development.

As one example, Human B7 homolog 1 (B7-H1), also called programmed cell death 1 ligand 1 (PDCD1L1) and programmed death ligand 1 (PD-L1), is a member of the growing B7 family of immune proteins that are understood to provide signals for both stimulating and inhibiting T cell activation. Without being bound by theory, PD-L1 binds to PD-1, which is expressed on the surface of activated T cells. The formation of a PD-1 receptor/PD-L1 ligand complex transmits an inhibitory signal which reduces the proliferation of T cells. These ligands are regarded as endogenous "checkpoints" for the immune system that allow for termination of an immune response after antigen activation (e.g. from an infection).

There is strong evidence that many tumors utilize these immune checkpoint molecules to evade immune destruction. Tumors have been shown to express PD-L1 as a soluble factor and/or on their surface. These observations have resulted in intensive efforts to develop immunotherapeutic approaches for cancer, including immune-checkpoint-pathway inhibitors such as human antibodies. In one embodiment, these checkpoint inhibitors are introduced into the microfluidic device comprising cancer cells (Cancer-on-chip) and the results are detected and measured.

The formation of a PD-1 receptor/PD-L1 ligand complex can be blocked by an antibody to either ligand. Thus, for cancer, one might block the PD-1 receptor on T cells, or one might block the PD-L1 ligand in solution or on the tumor cell. While one might think targeting either ligand generates comparable results, the clinical trial data (discussed below) shows some differences.

These ligands are not the only checkpoint molecules. CTLA-4 is another such immune molecule. As discussed below, BMS has commercialized an anti-CTLA-4 antibody (ipilimumab) for the treatment of patients with advanced melanoma.

In some contemplated embodiments, use Cancer-on-Chips technology to answer specific questions including determining the relevance of pathways/targets elucidated in mice, in humans, mechanism of action, and elucidating of novel mechanisms for drug targeting and immunotherapeutic development. Some examples of questions we could address would include: Address the potential impact of specific immunotherapy strategies on immune cells chemotaxis and tumor invasion and the corresponding changes in tumor biology; Study the effect of immunotherapy on tumor angiogenic activity; Study the effects of novel check-point inhibitors and relevant biologics and/or small molecules targeting the immune/tumor cells interaction;

Employ patient-specific tumor cells and reconstitute the whole cancer-on-chip with patient-specific cells, which may be primary cells and/or iPS-derived cells, including but not limited to endothelial, fibroblasts and/or immune cells. iPS cells that are differentiated to cell such as neurons, endothelial cells, hepatocytes, lung and gut epithelial cells may be used in Cancer-on-Chips; contribution of microbiome in tumor expansion or regression, as a prototype for studying microbiome-primary human tissue symbiosis and functional interaction; and efficacy of immune cells to attack the metastatic tumor, such as for example via interconnected Gut-on-Chips and Hepatoma Chips In some embodiments, the present invention contemplates using Cancer-on-Chips technology to trace the metastatic potential of tumors. Through effluent transfer we could explore the potential for circulating tumor cells to develop new cancer lesions in distant organs. Potential studies could then include: Manipulation of the Chip microenvironment to test impact of these changes on metastatic potential of the tumor. This could also be applied to patient-specific chips for precision medicine applications. Current microfluidic-based approaches for studying circulating tumor cells are too simplistic and therefore do not have the required biological complexity that Organ Cancer-on-Chips provide. Cancer-on-Chips could provide a useful tool to understand the mechanisms for lack of efficacy of many oncology drugs, uncovered often only in phase 2 clinical trials, as well as, address recent safety concerns such as with CAR T cell therapy, or other modified, engineered or activated immune cells used for immunotherapies.

Although in recent clinical trials, CAR T cell therapy has dramatically improved the outcomes of blood cancer patients with advanced, otherwise untreatable, forms of leukemia and lymphoma, the full potential of CARs for treating solid tumors has not been reached and many challenges remain. Having more predictive, human relevant systems to study human tumor biology, species difference in tumor biology between mice and humans, as well as the interactions of the human immune system with the tumor would advance our knowledge and help to provide the most robust and precise preclinical platforms for drug discovery for this devastating disease and enable the advancement of immunotherapies.

VI. Endpoints and Analysis Using the Chips

In some contemplated embodiments, Cancer-on-Chips may be evaluated by assays, including but not limited to: RNA and micro RNA profiling; Biochemical assays; Clinical chemistry panels; Metabolomic analysis; Proetomic analysis; Epigenomic profiling; Biomarkers; Imaging and histology; ELISAs; electrochemical sensing; mass spectrometry; and Flow cytometry.

VII. Potential Applications of Cancer-On-Chips

In some contemplated embodiments, Cancer-on-Chips may be used for Maintenance of long-term viability and function (weeks/months); High-resolution, real-time imaging; In vitro analysis of biochemical, genetic, and metabolic activities; Ability to step-wise recreate tissue complexity in vitro (introduction of multiple cell types into the system in relevant architecture); Engineering provides fine control over the microenvironment including mechanical forces and ECM; Able to study real-time complex cellular interactions not possible in animal models; Fluidic nature of the system allows linking and interactions between different organs systems (e.g. Lymph node-on-Chip and Tumor-on-Chip) not possible with other in vitro systems; Flow in the system allows analysis of recruitment of circulating immune cells that is central to the etiology of many diseases and toxicities; Flow creates a dynamic system with fresh nutrients that recapitulate circulation. The dynamic nature of systems provides an opportunity for improved pharmacokinetic/pharmacodynamic predictions; Enable mechanism of action studies in physiologically relevant system, e.g. for further understanding of mechanistic interaction between immune and tumor cells in a human relevant system, that will more accurately translate to the clinic; Can complement existing animal models and provide mechanistic insight and a bridge between existing animal models and translation to humans; Enable a systems biology approach for example to identify new potential targets for therapeutic development or biomarker identification. E.g. may uncover the order that specific interactions and pathways need to be targeted for the elimination of the tumor, as well as highlight the most critical nodes in this process. Enable discovery of novel targets for cancer immunotherapies; Enable identification off target effect and potential safety liabilities; Identification of novel biomarkers for assessment of clinical efficacy of cancer immunotherapies; Facilitate progress in personalized/precision medicine, with the potential to in the future use the Organs-on-Chips in a diagnostic application. This strategy may provide a unique approach to assess personalized immunotherapy and precision medicine in oncology, major goal of the field, as an effective anti-tumor therapeutic strategy; The power of the data obtained from these models can also be increase by combining with other efforts such humanized animal models, clinical trial data GWAS studies, single cells analysis; The Cancer-on-Chips have the potential to contribute to the extensive efforts to improve understanding of cancer biology and immune system interactions by providing a platform to test tumor and patient-specific therapeutic modalities and improve translation of animal data to the clinic.

Advantages of using Cancer-on-Chips, in additional to the high level of biological function and complexity achieved, is that an entire system that will include the Cancer-on-Chips coupled with the appropriate instrumentation and software, a Human Cancer Emulation System.

This will enable the end users in the future to easily employ the technology in their labs without any prior engineering expertise, prior experience handling Cancer-on-Chips, or specific know how.

DETAILED DESCRIPTION OF THE INVENTION

A Cancer-On-Chip (16) is composed of a clear, flexible polymer about the size of a USB memory stick, containing hollow fluidic channels (1) lined by living cells (see FIG. 4). These Cancer-On-Chips fully recreate the complex, dynamic state in which a living cancer cell interacts with and functions within a real human organ: including but not limited to having substrate (extracellular matrix), tissue-tissue interface and relevant epithelial, endothelial interactions, mechanical forces, immune cells and blood components, and biochemical surroundings. The fluidic nature of the system allows not only the recreation of mechanical forces applied by normal flow of blood in the body (sheer stress) known to be critical for both endothelial and epithelial cell function as well as other mechanical forces such as that cells experience in the body from say stretching of alveolar lung tissue as we breath. There is significant literature that demonstrates the importance of mechanical forces and mechanostransduction in biology and disease development—from determining cell shape and cell-cell interaction, changing gene expression profiles, to playing pivotal role in development biology and disease pathophysiology. The ability to recapitulate in vivo relevant mechanical forces in vitro is a feature that is missing from other in vitro systems and a clear advantage of our approach—specifically in studying tumor microenvironment. The fluidic nature of the system further allows the emulation of the dynamic environment that exists in tissues and organs and it further provides the ability to link different Cancer-On-Chips together to emulate the organ-to-organ interactions occurring in vivo providing a window into the physiology and improved mechanistic insight into human diseases and drug responses.

The microchannel(s) in the microfluidic devices can be substantially linear or they can be non-linear. In some embodiments, the channels are not limited to straight or linear channels and can comprise curved, angled, or otherwise non-linear channels. It is to be further understood that a first portion of a channel can be straight, and a second portion of the same channel can be curved, angled, or otherwise non-linear. Without wishing to be bound by a theory, a non-linear channel can increase the ratio of culture area to device area, thereby providing a larger surface area for cells to grow. This can also allow for a higher amount or density of cells in the channel. In some embodiments, the device can comprise an inlet channel connecting an inlet fluid port to the first chamber. The inlet channels and inlet ports can be used to introduce cells, agents (e.g., but not limited to, stimulants, drug candidate, particulates), airflow, and/or cell culture media into the first chamber.

I. A Membrane Located in Between the First Structure and Second Structure.

In one embodiment, the membrane is oriented along a plane between the first chamber and the second chamber. It should be noted that although one membrane is typically used, more than one membrane can be configured in devices which comprise more than two chambers.

The membrane separating the first chamber and the second chamber in the devices described herein can be porous (e.g., permeable or selectively permeable), non-porous (e.g., non-permeable), rigid, flexible, elastic or any combinations thereof. Accordingly, the membrane can have a porosity of about 0% to about 99%. As used herein, the term "porosity" is a measure of total void space (e.g., through-holes, openings, interstitial spaces, and/or hollow conduits) in a material, and is a fraction of volume of total voids over the total volume, as a percentage between 0 and 100% (or between 0 and 1). A membrane with substantially zero porosity is non-porous or non-permeable.

As used interchangeably herein, the terms "non-porous" and "non-permeable" refer to a material that does not allow any molecule or substance to pass through.

In some embodiments, the membrane can be porous and thus allow molecules, cells, particulates, chemicals and/or media to migrate or transfer between the first chamber and the second chamber via the membrane from the first chamber to the second chamber or vice versa.

As used herein, the term "porous" generally refers to a material that is permeable or selectively permeable. The term "permeable" as used herein means a material that permits passage of a fluid (e.g., liquid or gas), a molecule, a whole living cell and/or at least a portion of a whole living cell, e.g., for formation of cell-cell contacts. The term "selectively permeable" as used herein refers to a material that permits passage of one or more target group or species, but act as a barrier to non-target groups or species. For example, a selectively-permeable membrane can allow passage of a fluid (e.g., liquid and/or gas), nutrients, wastes, cytokines, and/or chemokines from one side of the membrane to another side of the membrane, but does not allow whole living cells to pass through. In some embodiments, a selectively-permeable membrane can allow certain cell types to pass through but not other cell types.

In some embodiments, a membrane can be a hydrogel or a gel comprising an extracellular matrix polymer, and/or a biopolymer or biocompatible material. In some embodiments, the hydrogel or gel can be embedded with a conduit network, e.g., to promote fluid and/or molecule transport. See, e.g., Wu et al. (2011) "Omnidirectional Printing of 3D Microvascular Networks." Advanced Materials 23: H178-H183; and Wu et al. (2010) "Direct-write assembly of biomimetic microvascular networks for efficient fluid transport." Soft Matter 6: 739-742, for example methods of introducing a conduit network into a gel material.

In some embodiments, a porous membrane can be a solid biocompatible material or polymer that is inherently permeable to at least one matter/species (e.g., gas molecules) and/or permits formation of cell-cell contacts. In some embodiments, through-holes or apertures can be introduced into the solid biocompatible material or polymer, e.g., to enhance fluid/molecule transport and/or cell migration. In one embodiment, through-holes or apertures can be cut or etched through the solid biocompatible material such that the through-holes or apertures extend vertically and/or laterally between the two surfaces of the membrane. It should also be noted that the pores can additionally or alternatively incorporate slits or other shaped apertures along at least a portion of the membrane which allow cells, particulates, chemicals and/or fluids to pass through the membrane from one section of the central channel to the other.

In some embodiments, pillars can be used instead of (or together with) a membrane. The spacing and dimensions of the pillars can be adjusted to permit or block the passage of cells.

In some embodiments, the membrane can be coated with substances such as various cell adhesion promoting substances or ECM proteins, such as fibronectin, laminin, various collagen types, glycoproteins, vitronectin, elastins, fibrin, proteoglycans, heparin sulfate, chondroitin sulfate, keratin sulfate, hyaluronic acid, fibroin, chitosan, or any combinations thereof. In some embodiments, one or more cell adhesion molecules can be coated on one surface of the membrane 208 whereas another cell adhesion molecule can be applied to the opposing surface of the membrane 208, or both surfaces can be coated with the same cell adhesion molecules. In some embodiments, the ECMs, which can be ECMs produced by cells, such as primary cells or embryonic stem cells, and other compositions of matter are produced in a serum-free environment.

In an embodiment, one can coat the membrane with a cell adhesion factor and/or a positively-charged molecule that are bound to the membrane to improve cell attachment and stabilize cell growth. The positively charged molecule can be selected from the group consisting of polylysine, chitosan, poly(ethyleneimine) or acrylics polymerized from acrylamide or methacrylamide and incorporating positively-charged groups in the form of primary, secondary or tertiary amines, or quaternary salts. The cell adhesion factor can be added to the membrane and is fibronectin, laminin, various collagen types, glycoproteins, vitronectin, elastins, fibrin, proteoglycans, heparin sulfate, chondroitin sulfate, keratin sulfate, hyaluronic acid, tenascin, antibodies, aptamers, or fragments or analogs having a cell binding domain thereof. The positively-charged molecule and/or the cell adhesion factor can be covalently bound to the membrane. In another embodiment, the positively-charged molecule and/or the cell adhesion factor are covalently bound to one another and either the positively-charged molecule or the cell adhesion factor is covalently bound to the membrane. Also, the positively-charged molecule or the cell adhesion factor or both can be provided in the form of a stable coating non-covalently bound to the membrane.

In some embodiments, cells are cultured on and/or under the membrane under flow conditions. In some embodiments, there is a steady-state perfusion of the cells. In other embodiments described herein, the devices can comprise a flowing culture medium in the first chamber and/or the second chamber, wherein the flowing culture medium generates a shear stress. Based on the viscosity of the culture medium and/or dimensions of the chambers, one of skill in the art can determine appropriate flow rates of culture medium through the chambers to achieve desired shear stress. In some embodiments, the flow rate of the culture medium through the first chamber can range from about 5 µL/hr to about 50 µL/hr. In some embodiments, the flow rate of the culture medium through the second chamber can range from about 15 µL/hr to about 150 µL/hr.

Thus, in one embodiment, fluidic shear forces are generated. In some embodiments, the first chamber, the second chamber or both may comprise or be in communication with one or more fluidic channels. Such channels may allow, for example, the perfusion, the delivery or removal of reagents, and/or the collection of samples from one or both of the chambers. Such channels may provide independent fluidic access to each chamber, and correspondingly, to either side of the membrane.

II. Optional Mechanical Actuation and Vacuum Channels

In some embodiments, the microfluidic devices comprises a means for creating mechanical actuation. Such mechanical actuation has been demonstrated to enact a biological effect, which may improve the emulation of the in vivo environment (REF: original Lung-on-a-Chip paper). Several designs for the mechanical actuation of Organ-Chips are disclosed in REF (HU4868). In some embodiments, fluidic channels in devices of the present inventions are optionally flanked by two vacuum channels that allow the pneumatically actuated stretching forces mimicking intestinal peristalsis. In some embodiments, stretching forces are for stretching an epithelial layer. In one embodiment, mechanical forces are generated.

III. Optional Gels

In some embodiments, the microfluidic device comprises a gel. Such a gel may provide an additional culture compartment, which may be used, for example, for culturing cells embed within the gel. Moreover, the gel may be invaded, reshaped, or remodeled by cells, thereby allowing the microfluidic to emulate various phenomena that occur in vivo.

III. Open Top Microfluidic Cancer-On-Chips.

Figure 11:
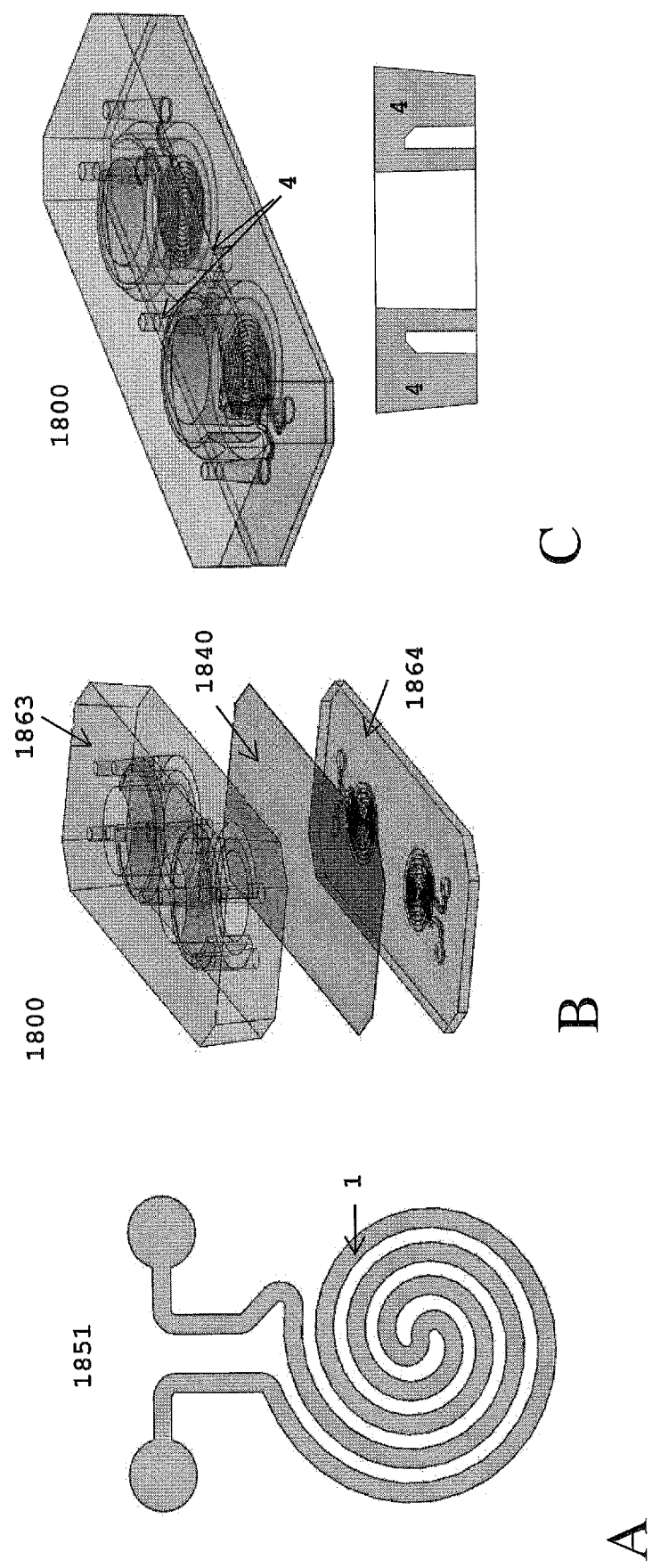
FIG. 11: Shows an exemplary schematic illustration of an open-top stretchable chip design as one embodiment of a chip used for Cancer-On-Chip.
Figure 12:
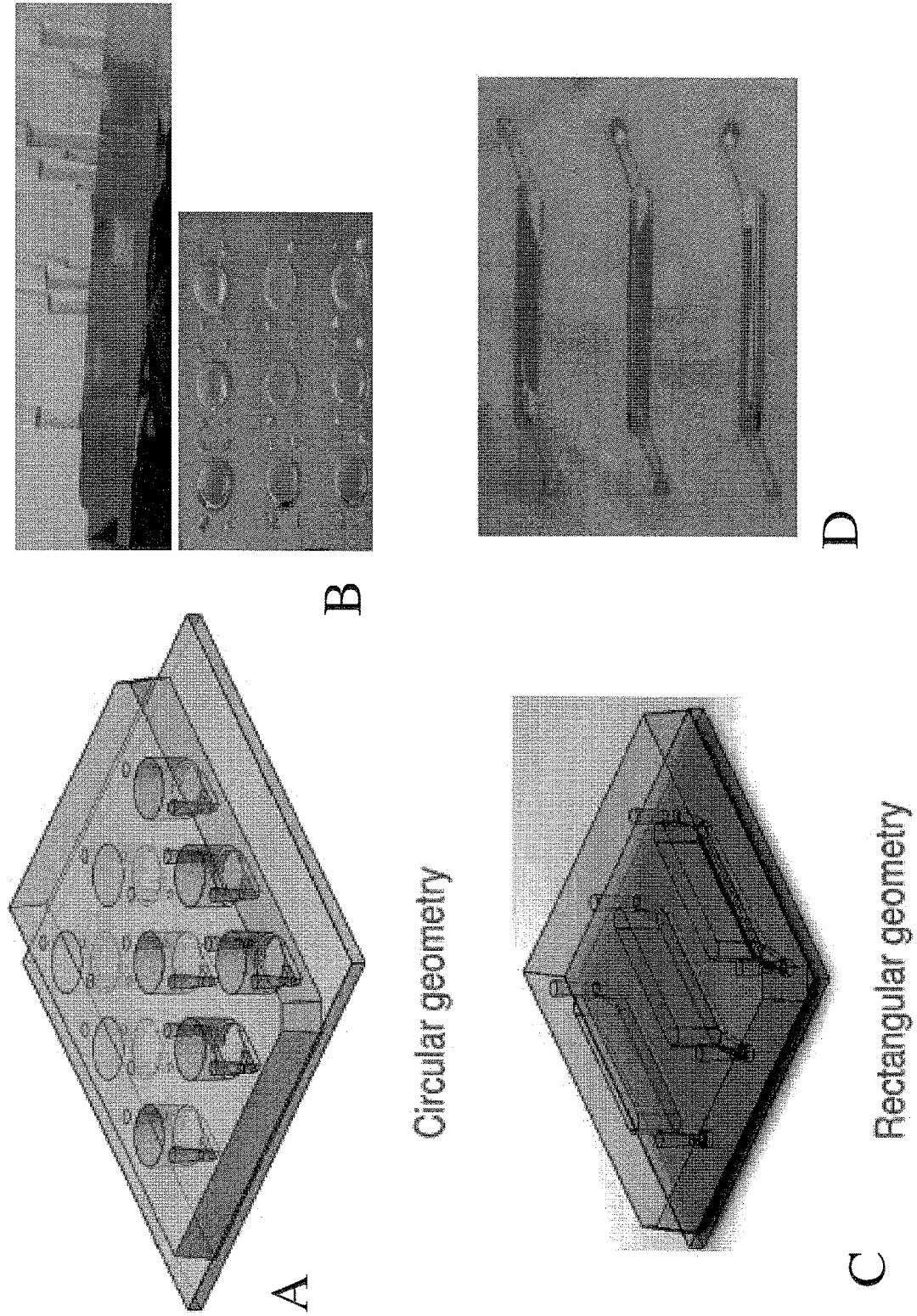
FIG. 12: Shows exemplary schematic illustrations of additional types of chips that may be used for a Cancer-On-Chip, in part depending upon the type of cancer/tumor.
Figure 13:
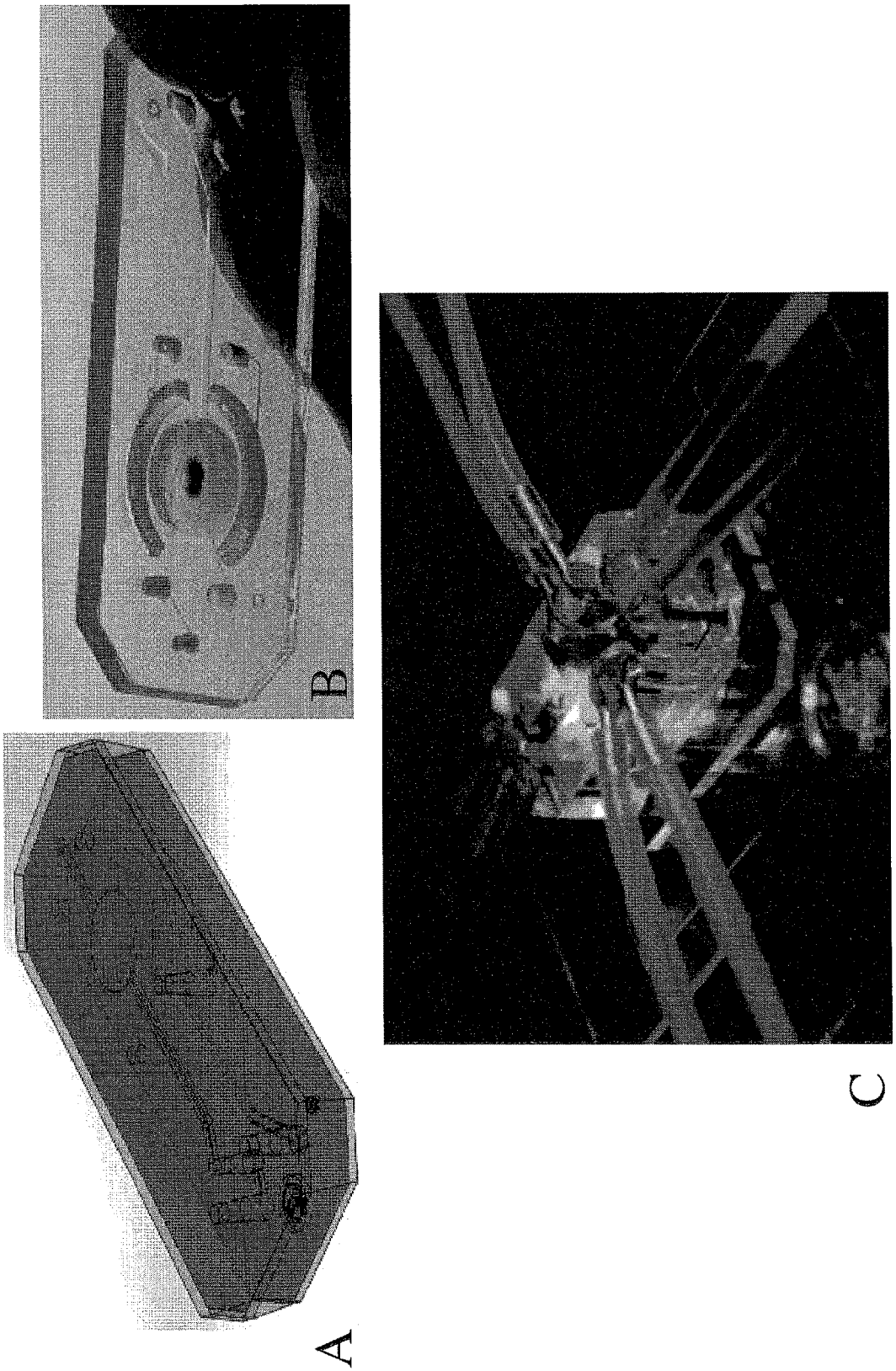
FIG. 13: Shows an exemplary schematic illustration and photographs of one embodiment of a Skon-chip for culturing cancer cells as a Cancer-On-Chip, e.g. metastatic melanoma.
Figure 14:
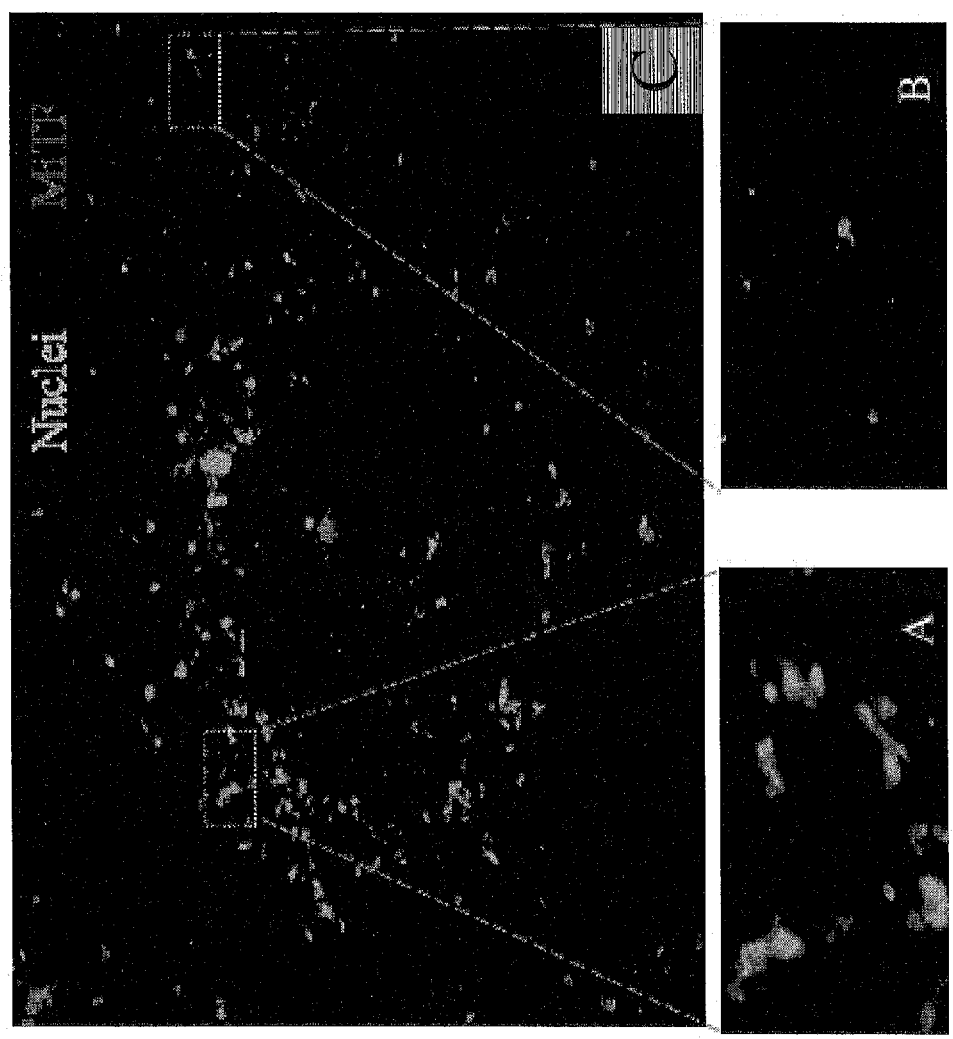
FIG. 14: Shows exemplary fluorescent micrographs of cancer cells growing within a 3D environment, e.g. metastatic melanoma, immunostained for MiTF (microphthalmia-associated transcription factor) positive-cells (green) and nuclei shown in blue (DAPI staining).
Figure 15:
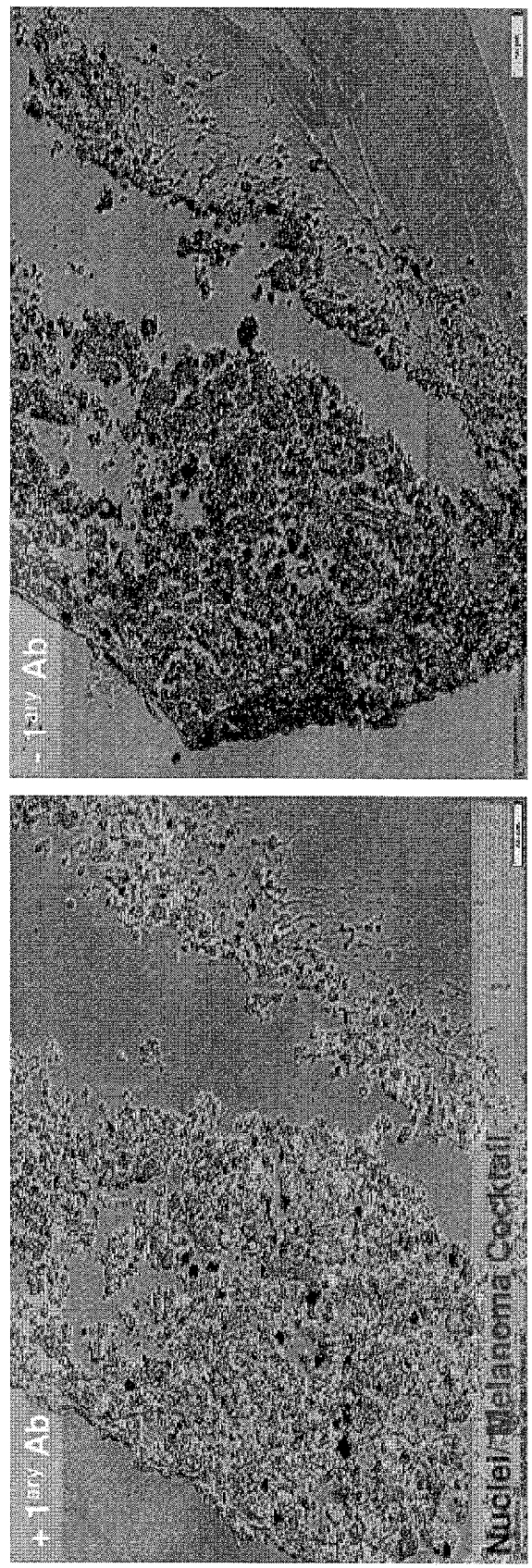
FIG. 15: Shows exemplary micrographs of stained tissue sections showing melanoma positive staining in cells cultured in cancer-on-chip. A melanoma Cocktail stain, i.e. HMB-45/Mart-1/Tyrosinase, refers to a mouse monoclonal antibody mixture (cocktail) used in routine clinical practice for the qualitative identification of human melanoma and melanoma metastatic cells. For reference, HMB-45 antibody reacts with a neuraminidase sensitive oligosaccharide side chain of a glycoconjugate. Mart-1 refers to Melan-A: a melanoma antigen recognized by T cells. Tyrosinase refers to an oxidase enzyme (protein) which catalyzes reactions producing black/brown pigment within melanosomes.
Figure 16:
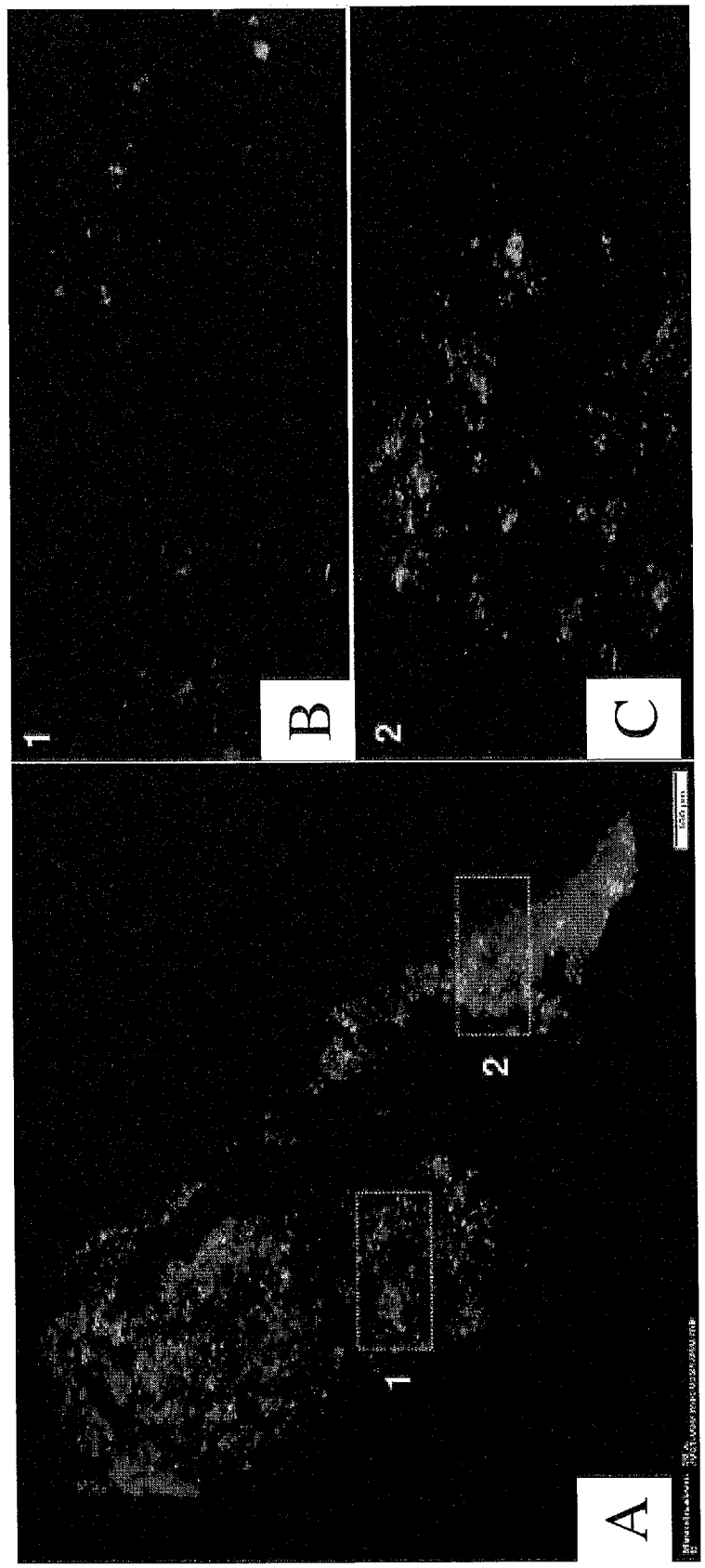
FIG. 16: Shows exemplary micrographs of Melanoma Cocktail stained tissue sections showing melanoma positive cells cultured in cancer-on-chip. Melanoma Cocktail [HMB-45/Mart-1/Tyrosinase] is used in routine clinical practice for identification of Melanoma and Melanoma Metastases. Melanoma-on-Chip fixed, sectioned and stained with the Melanoma Cocktail, 11 days post seeding.
Figure 17:
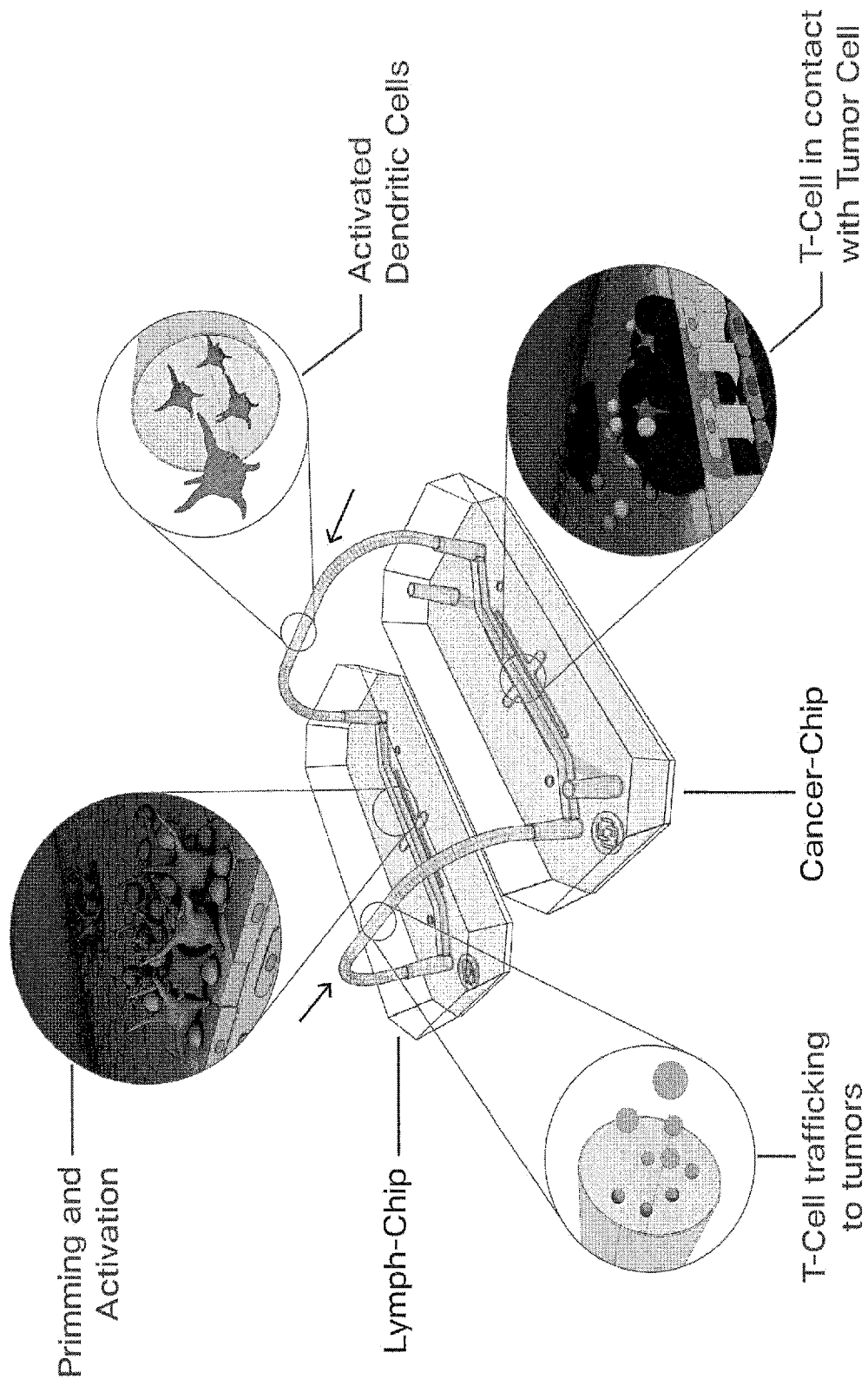
FIG. 17: Shows an exemplary schematic illustration of a Cancer-Chip (Cancer-On-Chip) linked to a downstream (i.e. fluid receiving) Lymph Chip (Lymph Node-on-chip) that in turn has an upstream (i.e. fluid emitting) connection to the Cancer-Chip (i.e. circular fluidic flow/connection). Illustrations show examples of migratory immune cells.
Figure 18:
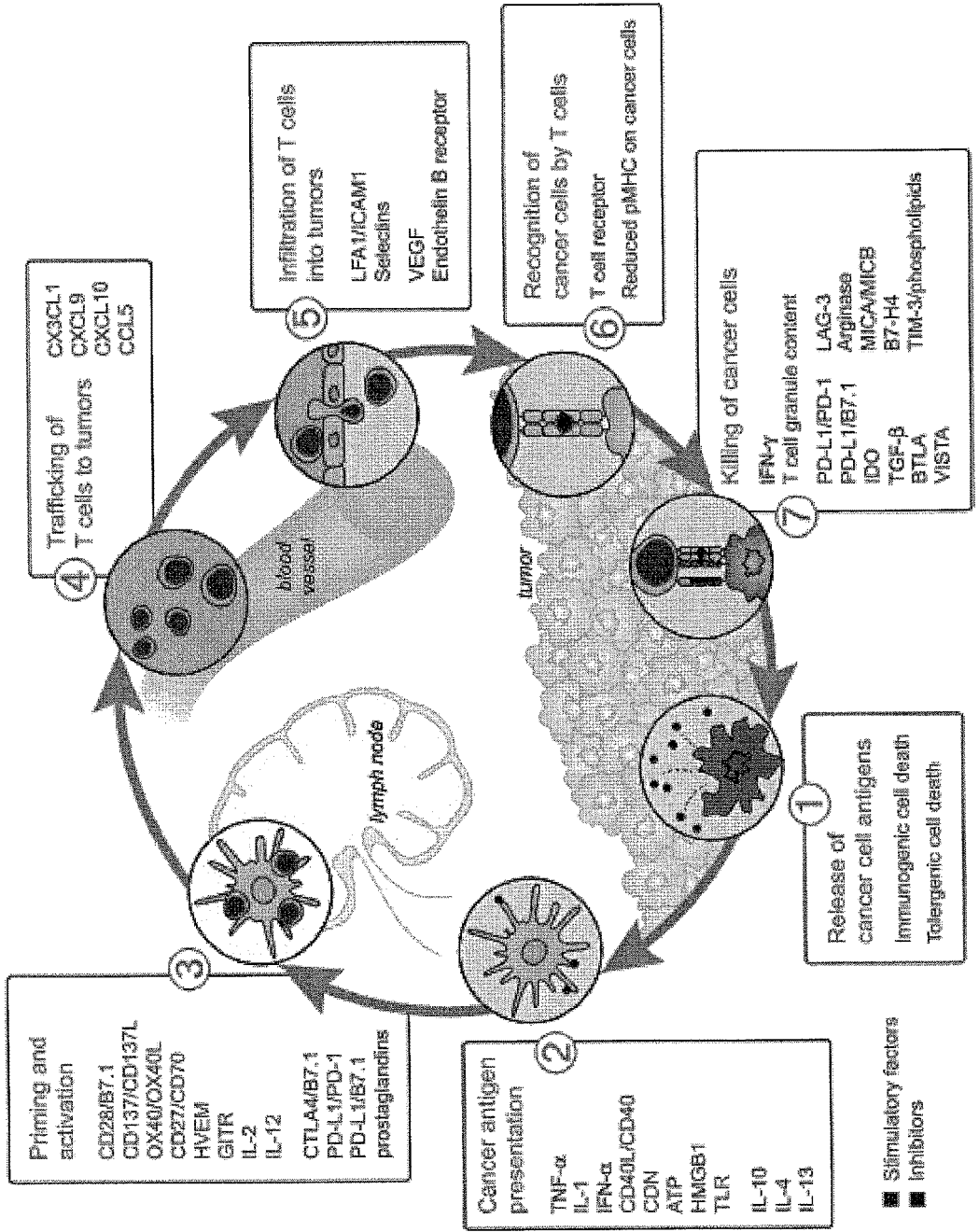
FIG. 18: Shows an exemplary schematic illustration of numerous stimulatory and inhibitory factors in the cancer-immunity cycle. Chen and Mellman Immunity Rev. 2013.
Figure 19:
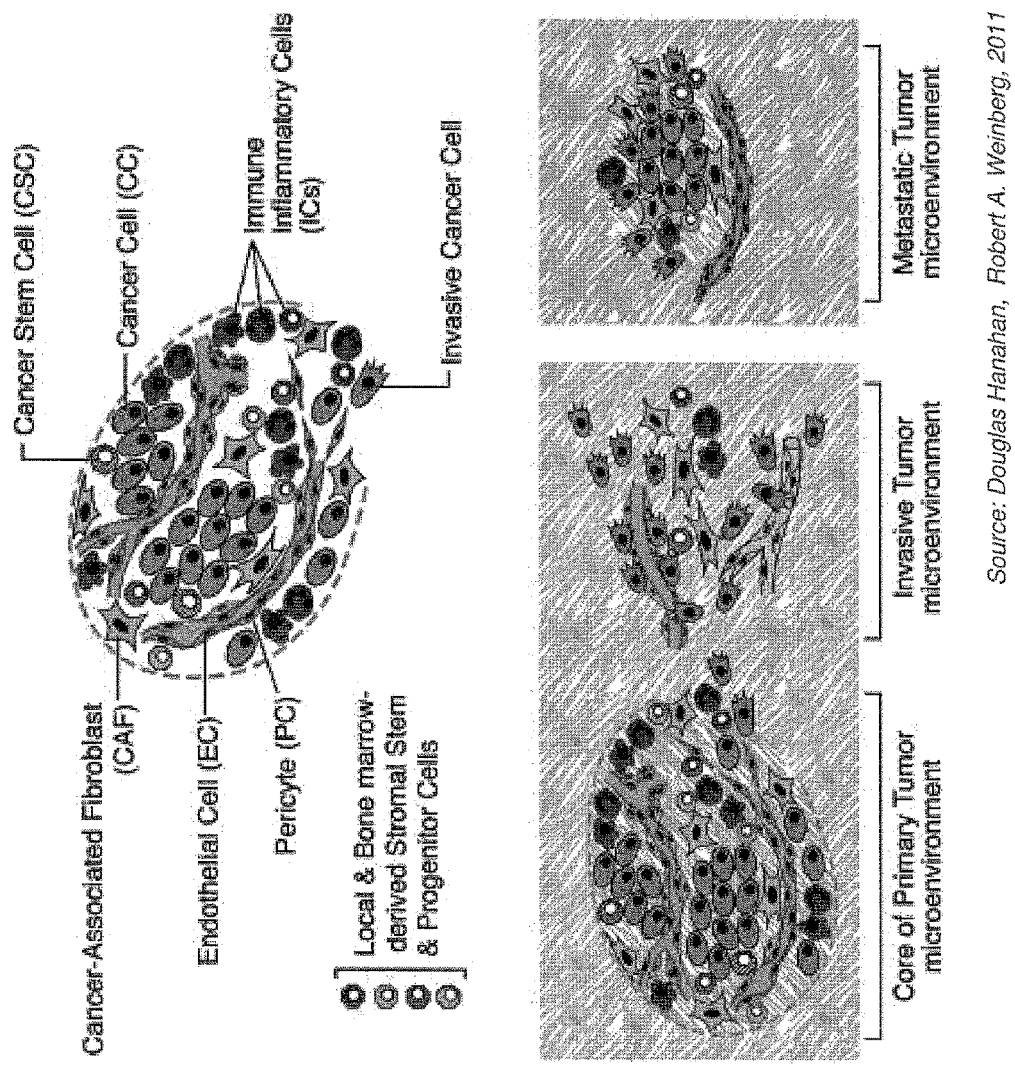
FIG. 19: Shows exemplary schematic illustrations of embodiments for components of a Microenvironment for Invasive Tumors. Douglas Hanahan, Robert A. Weinberg, 2011.
Figure 20:
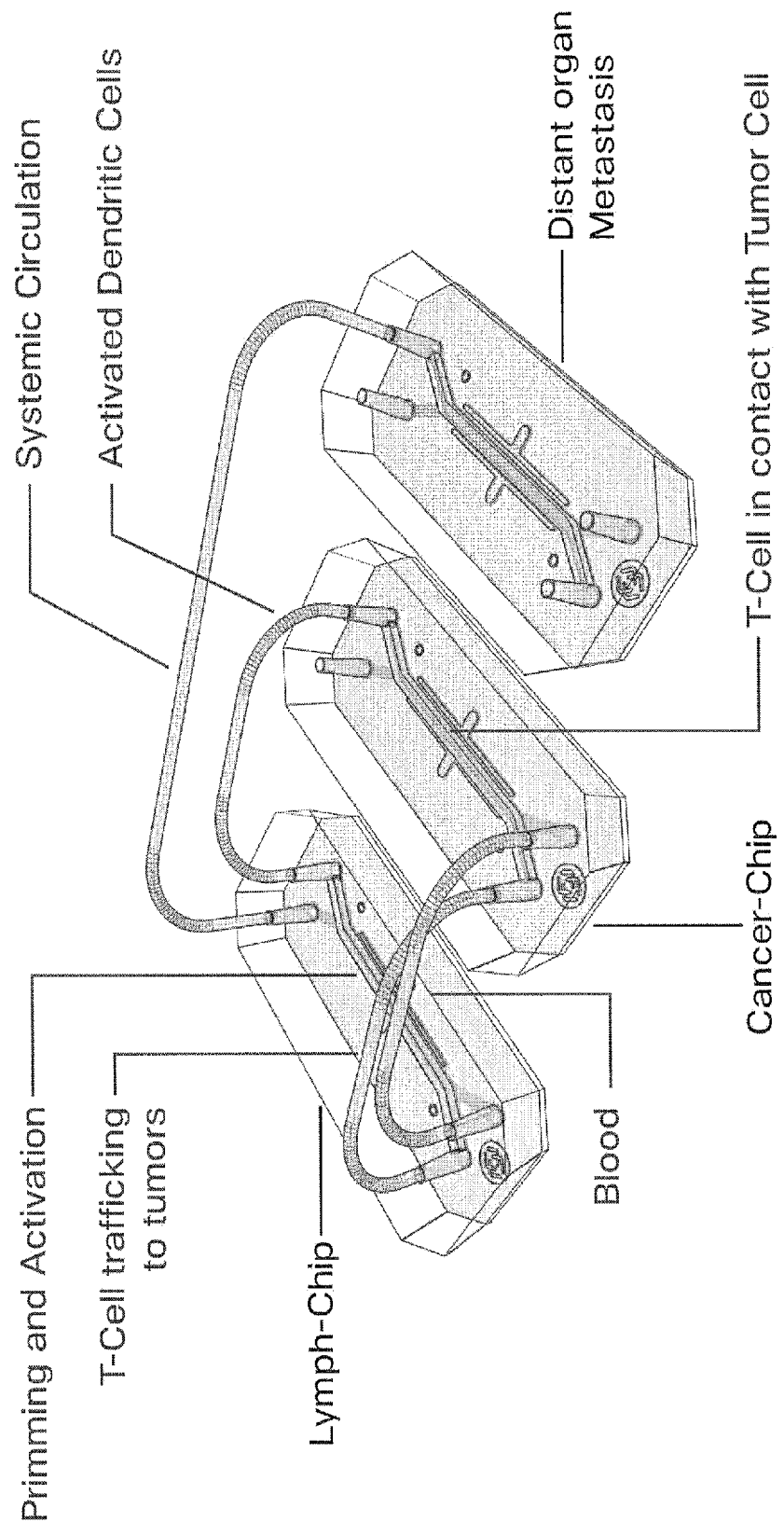
FIG. 20: Shows an exemplary schematic illustration of a Cancer-Chip (Cancer-On-Chip) linked to a Lymph Chip (Lymph Node-on-chip) as shown in FIG. 17, with at least one additional Organ-chip fluidically attached to the Lymph Chip for providing a Metastasis-Chip (System). In one embodiment, there is an incorporation of a vascular Component the Lymph Chip.
Figure 21:
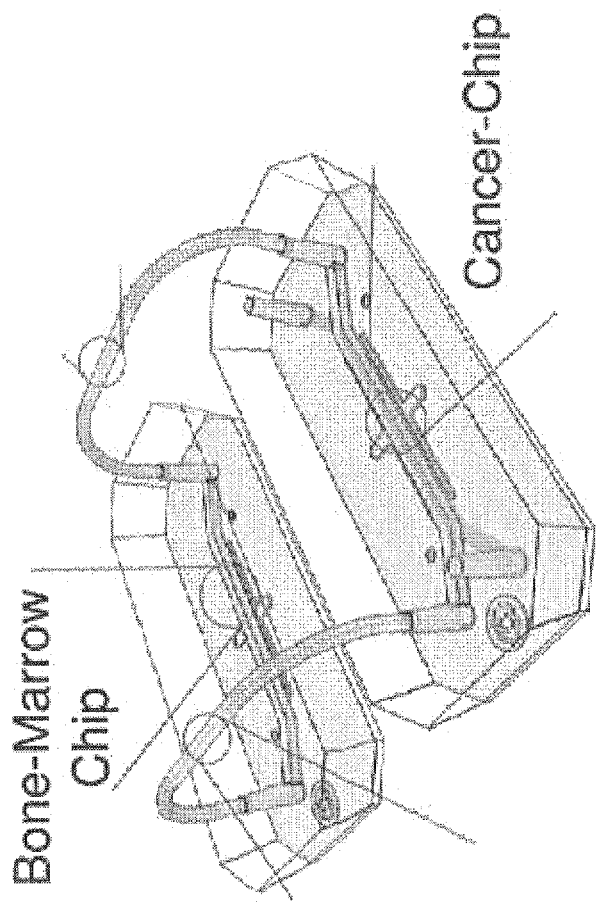
FIG. 21: Shows an exemplary schematic illustration of a Cancer-Chip (Cancer-On-Chip) fluidically linked to a Bone-Marrow Chip (Bone-Marrow-on-chip).

The present disclosure relates to Cancer-On-Chips, such as fluidic devices comprising one or more cells types for the simulation one or more of the function of bodily components, e.g. normal cells, cancer cells, cells derived from a tissue area, cells derived from blood, cells derived from an organ at risk of developing cancer, or a component of a microenvironment derived from an area where cancer cells arose but without cancer cells, etc. Accordingly, the present disclosure additionally describes open-top Cancer-On-Chips, see, e.g. schematic in FIGS. 4, 11-12. FIG. 11 shows an exemplary exploded view of one embodiment of an open-top chip device 1800, wherein a membrane 1840 resides between the bottom surface of the first chamber 1863 and the second chamber 1864 and the at least two spiral microchannels 1851. Open top microfluidic chips include but are not limited to chips having removable covers, such as removable plastic covers, paraffin covers, tape covers, etc.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components Therefore, the present disclosure relates to fluidic systems that include a fluidic device, such as a microfluidic device with an opening that provides direct access to device regions or components (e.g. access to the gel region, access to one or more cellular components, etc.). Although the present disclosure provides an embodiment wherein the opening is at the top of the device (referred to herein with the term "open top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.).

While detailed discussion of the "open top" embodiment is provided herein, those of ordinary skill in the art will appreciate that many aspects of the "open top" embodiment apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more gel layers for simulating the application of topical treatments on the cells, tissues, or organs, or (ii) the addition of chemical or biological components such as the seeding of additional cell types for simulated tissue and organ systems. The present disclosure further relates to improvement in fluidic system(s) that improve the delivery of aerosols to simulated tissue and organ systems, such as simulated gastrointestinal tissues.

The present invention contemplates a variety of uses for these open top microfluidic devices and methods described herein. In one embodiment, the present invention contemplates a method of topically testing an agent (whether a drug, gas, or other substance) comprising 1) providing a) an agent and b) microfluidic device comprising i) a chamber, said chamber comprising a lumen and projections into the lumen, said lumen comprising ii) a gel matrix anchored by said projections and comprising cells (e.g. tumor cells) in, on or under said gel matrix, said gel matrix positioned above iii) a porous membrane and under iv) a removable cover, said membrane in contact with v) fluidic channels; 2) removing said removable cover; and 3) topically contacting said cells in, on or under said gel matrix with said agent. In one embodiment, said agent is in an aerosol. In one embodiment, agent is in a liquid, gas, gel, semi-solid, solid, or particulate form. These uses may apply to the open top microfluidic chips described below and herein.

A. Open Top Microfluidic Chips without Gels.

In one embodiment, open top Cancer-On-Chips do not contain gels, either as a bulk gel or a gel layer. Thus, the present invention also contemplates, in one embodiment, a layered structure comprising i) fluidic channels covered by ii) a porous membrane, said membrane comprising iii) a layer or collection of cells (e.g. tumor cells) and said membrane positioned below said cells. In one embodiment, there is a removable cover over the cells.

Additional embodiments are described herein that may be incorporated into open top chips without gels.

B. Open Top Microfluidic Chips with Gels.

Furthermore, the present disclosure contemplates improvements to fluidic systems that include a fluidic device, such as a microfluidic device with an open-top region that reduces the impact of stress that can cause the delamination of tissue or related component(s) (e.g., such as a gel layer). Thus, in a preferred embodiment, the open-top microfluidic device comprises a gel matrix. In one embodiment, the open-top microfluidic device does not contain a bulk gel.

The present invention also contemplates, in one embodiment, a layered structure comprising i) fluidic channels covered by ii) a porous membrane, said membrane comprising iii) a layer or collection of cells (e.g. tumor cells) and said membrane positioned below iv) a gel matrix. In one embodiment, there is a removable cover over the gel matrix (and/or cells). It is not intended that the present invention be limited to embodiments with only one gel or gel layer. In one embodiment, the layered structure further comprises a second gel matrix (e.g. positioned under said membrane). The gel(s) or coatings can be patterned or not patterned. Moreover, when patterned, the pattern need not extend to the entire surface. For example, in one embodiment, at least a portion of said gel matrix is patterned. It is not intended that the present invention be limited by the nature or components of the gel matrix or gel coating. In one embodiment, gel matrix comprises collagen. A variety of thickness is contemplated. In one embodiment of the layered structure, said gel matrix is between 0.2 and 6 mm in thickness.

In yet another embodiment, the present invention contemplates a microfluidic device comprising i) a chamber, said chamber comprising a lumen and projections in the lumen, said lumen comprising ii) a gel matrix anchored by said projections, said gel matrix positioned above iii) a porous membrane, said membrane in contact with iv) fluidic channels. In one embodiment, said membrane comprises cells (e.g. tumor cells). The projections serve as anchors for the gel. The projections, in one embodiment, project outward from the sidewalls. The projections, in another embodiment, project upward. The projects, in another embodiment, project downward. The projections can take a number of forms (e.g. a T structure, a Y structure, a structure with straight or curving edges, etc.). In some embodiments, there are two or more projections; in other embodiments, there are four or more projections to anchor the gel matrix. In one embodiment, the membrane is above said fluidic channels.

In other embodiments, open top microfluidic chips comprise partial lumens as described herein for closed top chips. Thus, in some embodiments, open top microfluidic chips comprise lumens formed by viscous fingering described herein for closed top chips.

Lumen gel structures may be used in several types of embodiments for open top microfluidic chips, e.g. epithelial cells can be attached to outside of the gel, or within the gel. In some embodiments, ECM components may be added within the gel, or below the gel. In some embodiments, LPDCs may be added within the gel, or below the gel. In some embodiments, stomal cells are added within the gel. In some embodiments, stomal cells are attached to the side of the gel opposite from the lumen. In some embodiments, endothelial cells are located below the gel on the side opposite the lumen. In some embodiments, endothelial cells may be present within the gel. Additional embodiments are described herein that may be incorporated into open top chips with gels.

The present invention contemplates combining features from different embodiments. The present invention contemplates removing features from the above-indicated embodiments. For a non-limiting example, co-cultures of cancer cells with epithelial cells, endothelial cells and stromal cells may have a feature removed. For example, subsets of cells isolated from infiltrates of cancer cells, such as TILs, may be removed from the configuration in order to identify cells or components, contributing to specific disease phenotypes. For another non-limiting example, stromal cells may be removed from the configuration in order to identify components contributing to specific disease phenotypes. The present invention contemplates adding features to the configuration in order to identify cells initiating a specific cancer phenotype, e.g. adding diseased LP-derived cells, e.g. isolated from areas of tumor growth, to microfluidic devices containing precancerous or healthy cells. The present invention contemplates substituting features in the above-indicated embodiments. For a non-limiting example, ECM from commercial sources may be substituted with ECM isolated from humans.

IV. Exemplary Devices for Simulating a Function of a Tissue.

Some embodiments described herein relate to devices for simulating a function of a tissue, in particular a gastrointestinal tissue. In one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer.

V. ECM Coating.

To determine optimum conditions for cell attachment, the surface-treated material (e.g., APTES-treated or plasma-treated PDMS) can be coated with an ECM coating of different extracellular matrix molecules at varying concentrations (based on the resulting cell morphology and attachment).

VI. ECM Overlay.

The ECM overlay is typically a "molecular coating," meaning that it is done at a concentration that does not create a bulk gel. In some embodiments, an ECM overlay is used. In some embodiments, an ECM overlay is left in place throughout the co-culturing. In some embodiments, an ECM overlay is removed, e.g. when before seeding additional cells into a microfluidic device. In some embodiments, the ECM layer is provided by the cells seeded into the microfluidic device.

Although cells described for use in a Cancer-On-Chip make their own ECM, it is contemplated that ECM in predisease and diseased states may may be found in areas around sites of cancer cell growth. Further, the protein microenvironment provided by ECM also affects cells. Thus it is contemplated that tissue-derived ECM may carry over a disease state. Therefore, in addition to the ECM described herein, ECM used in microfluidic devises of the present inventions may be derived from or associated with areas in and around sites of cancer cells. In one embodiment, a device comprising tissue-derived ECM may be used as described herein, to identity contributions to healthy or disease states affected by native ECM.

For example, ECM may be isolated from biopsies of healthy, non-disease and disease areas as tissue-derived ECM. Isolates for use may include cells within or attached or further processed to remove embedded cells for use in the absence of the cells.

Additional examples of ECM materials include but are not limited to Matrigel®, Cultrex®, ECM harvested from humans, etc.

Matrigel® is a trade name for a solubilized basement membrane preparation extracted from the Engelbreth-Holm-Swann (EHS) mouse sarcoma, a tumor rich in such ECM proteins as laminin (a major component), collagen IV, heparin sulfate proteoglycans, entactin/nidogen, and a number of growth factors as produced and marketed by Corning Life Sciences. Matrigel® gels to form a reconstituted basement membrane. Versions of Matrigel® include BD Matrigel® (Basement Membrane) Matrix, offered as Standard, Growth Factor Reduced, Growth Factor Reduced-High Concentration (HC) and Growth Factor Reduced-Phenol Red-Free formulations, BD Matrigel® hESC-qualified Matrix, by BD Biosciences.

Trevigen, Inc. markets other ECM versions of BME harvested as a soluble form of basement membrane purified from Engelbreth-Holm-Swarm (EHS) tumor cells under the trade name Cultrex® Basement Membrane Extract (BME). Cultrex® extract gels at 37° C. to form a reconstituted basement membrane. The major components of Cultrex® BME include laminin, collagen IV, entactin, and heparin sulfate proteoglycan. Several forms Cultrex® are offered by Trevigen as: Cultrex® Reduced Growth Factor Basement Membrane Extract, Type R1. Type R1 matrix provides a proprietary formulation that has higher tensile strength when compared to other Cultrex® products, i.e. Cultrex® BME, Cultrex® BME Type 2 and Cultrex® BME Type 3. Type R1 has a higher concentration of entactin, one of the BME components that connects laminins and collagens reinforcing the hydrogel structure. Cultrex® BME Type R1 has been specifically designed to culture tissue organoids. BME type R1 supports culture of human gastric or small intestine organoids. In a Tube formation assay—BME type R1 promotes formation of capillary-like structures by human (HBMVEC; HUVEC); Barker, et al., Lgr5+ve Stem Cells Drive Self-Renewal in the Stomach and Build Long-Lived Gastric Units In Vitro. Cell Stem Cell, 2010. 6(1): p. 25-36; Sato, T., et al., Single Lgr5 stem cells build crypt-villus structures in vitro without a mesenchymal niche. Nature, 2009. 459(7244): p. 262-26; Sato, T. and H. Clevers, Growing Self-Organizing Mini-Guts from a Single Intestinal Stem Cell: Mechanism and Applications. Science, 2013. 340 (6137): p. 1190-1194; Jung, P., et al., Isolation and in vitro expansion of human colonic stem cells. Nat Med, 2011. 17(10): p. 1225-7.). Under a Cultrex® Organoid Qualified BME, Type 2 designation, several formulations of Cultrex® BME are described for organoid culture including Cultrex® Basement Membrane Extract, Type 2, PathClear® (provided as part of a protocol for subculturing normal human gastric organoids which was derived from the submerged method as described in Barker, et al., Lgr5+ve Stem Cells Drive Self-Renewal in the Stomach and Build Long-Lived Gastric Units In Vitro. Cell Stem Cell, 2010. 6(1): p. 25-36)) and Cultrex® Reduced Growth Factor Basement Membrane Extract, Type 2, PathClear® (Human Colorectal Cancer (CRC) organoids grown from single cells on Cultrex® BME Type 2 Reduced Growth Factor). Additional products that might find use include but are not limited to Cultrex® 3-D Culture Matrix® Reduced Growth Factor Basement Membrane Extract, PathClear® (allowing for the formation of acinar and other hollow unnamed structures in vitro); Cultrex® Basement Membrane Extract, PathClear®; Cultrex® Stem Cell Qualified Reduced Growth Factor Basement Membrane Extract, PathClear®; Cultrex® Basement Membrane Extract, Type 3, PathClear®. The PathClear® designation means that in addition to standard sterility, endotoxin and MAP testing, the basement membrane extract is tested by PCR and is clear of 31 pathogens and viruses, including lactate dehydrogenase elevating virus (LDEV). Cultrex® BME Type 2 provides a formulation with a higher in tensile strength when compared to the original BME, while Cultrex® BME Type 3 is physiologically aligned with the in vivo solid tumors environment and is recommended for xenografts and other in vivo applications.

EXPERIMENTAL

The following is a summary of contemplated experimental strategy. With the experimental strategy as delineated herein, we aim to develop in a stepwise approach a number of distinct although interlocking platforms to study human cancer as delineated below. Proof of concept in all of the following steps will be provided by identical experiments in chips populated with cells from transgenic/humanized mouse models amenable to purification and real-time tracing of all the relevant cells to be used, together with well-characterized tumor cells.

Example 1

Tumor Development and Expansion within the Normal Tissue

Seeding Cancer-On-Chips with cells derived from fresh human tumor specimens demonstrating grow in the Chip and providing a population composition representative of the original tumor, i.e. confirm we do not select from the more aggressive or the more differentiated cell type. Endothelial cells will be incorporated, the interaction between tumor cells and endothelial cells will be characterized and angiogenesis will be monitored. In this experiment, compounds targeting the cell cycle or specific cell functions such as autophagy, as well as tumor vasculature and angiogenesis could be tested for determining whether known anticancer agents have similar effects in Cancer-On-Chips, in addition to testing compounds as potential therapeutics.

Example 2

Tumor Invading in the Surrounding Tissues, i.e. the Stroma and the Supporting Endothelial and Lymphatic System In this example, the response of stroma to tumor cells and the effects of activated (tumor-derived) fibroblasts on tumor cells biology are shown. Activation of stroma, interaction with tumor cells, and changes in the phenotype of tumor cells following interaction with stroma, effects on the vascular systems such as changes in permeability, neovascularization, metabolic function will be evaluated.

Example 3

Incorporation of the Immune System in the Tumor and Stroma-On-Chip

In this example, antigen priming and/or immune cell migration will be studied in relation to cancer cell/tumor growth. In one embodiment, dendritic cells (DC) are fluidically circulated through the tumor compartment in order to prime them to tumor antigens. In one embodiment, resident immune cells are included to study their role in cancer development. In one embodiment, a separately maintained culture of cytotoxic cells dyed with a cell dye to be distinct and traceable by microscopy, will be exposed to the primed DC to assess the physiologically relevant interaction and then will be flown (fluidically circulated) in the system through the vascular system to assess the existence of an in vivo relevant "immune privileged" environment. In one embodiment, a model for recruitment of immune cells by the tumor will be evaluated where either immune cells have migrated within the tumor to become a critical component of the immunosuppressive properties of the tumor, such as myeloid suppressor cells (MSC), or surround the tumor, or are excluded from entry (such as CD8+ T cytotoxic cells). In one embodiment, immune cells that move away will be collected with the effluent from the Cancer-In-Chip.

Example 4

Tumor and Stroma and Immune System-On-Chip

In this example, Mesenchymal stem cells (MSCs) will be studied in relation to cancer cell/tumor growth. In one embodiment, recruited MSCs, originating from Bone marrow-Chip, i.e. a microengineered model that replicates native niche and key immunological function of mammalian, e.g. human bone marrow in vivo, will be studied in relation to cancer cell/tumor growth.

This Bone marrow-Chip in communication with a Cancer-On-Chip will be constructed by incorporating human bone marrow obtained surgically from thoracectomy into a perfusable microfluidic device that contains a vascularized three-dimensional tissue culture scaffold. The design of this model will enable spontaneous anastomosis of the microvasculature in the marrow with a network of microengineered blood vessels, making it possible to generate and precisely control vascular perfusion of the bone marrow. Once this culture is established, human hematopoietic stem cells will be introduced into the engineered tissue and induced to differentiate into the myeloid lineage. Functional validation of this model will be achieved by measuring mobilization of neutrophils in response to colony-stimulating factors such as G-CSF or CXC chemokines such as IL-8.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method comprising:
   1) providing
      a) a microfluidic device comprising:
         a body having a first channel and a first chamber, an at least partially porous membrane positioned at an interface region between the first channel and the first chamber, the membrane comprising a top surface and a bottom surface, said top surface facing the first chamber;
         living epithelial cells disposed within the first chamber as a layer of cells; and
         living tumor cells in contact with said living epithelial cells, said tumor cells originating from a biopsy, and disposed within at least one of the first chamber or the first channel; and
   2) testing said epithelial cell layer for invasion by said tumor cells.

2. The method of claim 1, wherein the first chamber comprises a second channel.

3. The method of claim 1, wherein the first chamber comprises an open region.

4. The method of claim 1, wherein said tumor cells comprise melanoma cells.

5. The method of claim 1, wherein the method further comprises endothelial cells disposed within the first channel.

6. A method comprising:
   1) providing
      a) a microfluidic device comprising a body having a first chamber, an at least partially porous membrane comprising a top surface and a bottom surface, said top surface facing the first chamber;
      b) living epithelial cells disposed within the first chamber as a layer of cells; and
      c) living tumor cells in contact with said living epithelial cells, and disposed within said first chamber; and
   2) testing said epithelial cell layer for invasion by said tumor cells.

7. The method of claim 6, wherein said tumor cells comprise melanoma cells.

* * * * *